(12) United States Patent
Okada et al.

(10) Patent No.: US 8,063,245 B2
(45) Date of Patent: Nov. 22, 2011

(54) PHOSPHAZENE COMPOUND, PHOTOSENSITIVE RESIN COMPOSITION AND USE THEREOF

(75) Inventors: Koji Okada, Settsu (JP); Toshio Yamanaka, Settsu (JP)

(73) Assignee: Kaneka Corporation, Osaka (JP)

( * ) Notice: Subject to any disclaimer, the term of this patent is extended or adjusted under 35 U.S.C. 154(b) by 815 days.

(21) Appl. No.: 10/559,737

(22) PCT Filed: Jun. 3, 2004

(86) PCT No.: PCT/JP2004/007719
§ 371 (c)(1),
(2), (4) Date: Dec. 5, 2005

(87) PCT Pub. No.: WO2005/019231
PCT Pub. Date: Mar. 3, 2005

(65) Prior Publication Data
US 2006/0142542 A1    Jun. 29, 2006

(30) Foreign Application Priority Data

| Jun. 5, 2003 | (JP) | 2003-161079 |
| Jul. 30, 2003 | (JP) | 2003-204023 |
| Jul. 30, 2003 | (JP) | 2003-204036 |

(51) Int. Cl.
*C07F 9/547* (2006.01)
(52) U.S. Cl. .................................................... 564/13
(58) Field of Classification Search .................. 564/13
See application file for complete search history.

(56) References Cited

U.S. PATENT DOCUMENTS

| 3,711,389 A * | 1/1973 | Hook et al. ................ 522/89 |
| 4,256,715 A | 3/1981 | Kinoshita et al. |
| 5,773,509 A | 6/1998 | Yoshida et al. |
| 5,994,497 A | 11/1999 | Raith et al. |
| 6,596,893 B2 * | 7/2003 | Nakacho et al. ............ 558/157 |
| 7,195,857 B2 * | 3/2007 | Tamura et al. ............ 430/280.1 |

| 2001/0056174 A1 | 12/2001 | Okada et al. |
| 2002/0161077 A1 | 10/2002 | Shimizu et al. |
| 2003/0166812 A1 * | 9/2003 | Taniguchi et al. ............ 526/274 |

FOREIGN PATENT DOCUMENTS

| JP | 54-145394 | 11/1979 |
| JP | 54-145395 | 11/1979 |
| JP | 58-219190 | 12/1983 |
| JP | 06-027667 | 2/1994 |
| JP | 07-242820 | 9/1995 |
| JP | 10-000733 | 1/1998 |
| JP | 10168428 A | 6/1998 |
| JP | 11-181268 | 7/1999 |
| JP | 2001-019930 | 1/2001 |
| JP | 2001-040149 | 2/2001 |
| JP | 2001-040219 | 2/2001 |
| JP | 2001-049090 | 2/2001 |
| JP | 2001-335619 | 12/2001 |
| JP | 2001-335703 | 12/2001 |
| JP | 2002-235001 | 8/2002 |
| JP | 2003-302751 | 10/2003 |

OTHER PUBLICATIONS

Giancarlo Fantin et al., "Photosensitive Phosphazene Substrates: Synthesis and Characterization", Gazzeta Chimica Italiana, vol. 127, 1997, No. 5., p. 287-292.

* cited by examiner

*Primary Examiner* — Peter O Sullivan
(74) *Attorney, Agent, or Firm* — Hogan Lovells US LLP

(57) ABSTRACT

Disclosed is a phosphazene compound and a photosensitive resin composition. The phosphazene compound is obtained by reacting a phenoxyphosphazene compound (A-1) having a phenolic hydroxyl group and/or a cross-linked phenoxyphosphazene compound (A-2) obtained by cross-linking the phenoxyphosphazene compound (A-1) with an epoxy compound (B) having an unsaturated double bond and/or an isocyanate compound (C), wherein the phosphazene compound has an unsaturated double bond in its molecule. The photosensitive resin composition includes at least: a soluble polyimide resin (G-1) having a carboxyl group and/or a hydroxyl group and is soluble in an organic solvent, as the polyimide resins (G); and a phenoxyphosphazene compound (H-1) having a phenolic hydroxyl group and/or a cross-linked phenoxyphosphazene compound (H-2), which is obtained by cross-linking the phenoxyphosphazene compound (H-1) and has at least one phenolic hydroxyl group, as the phosphazene compound (H), and the photosensitive resin composition further includes a (meth)acrylic compound (L).

9 Claims, 1 Drawing Sheet

PHOSPHAZENE COMPOUND, PHOTOSENSITIVE RESIN COMPOSITION AND USE THEREOF

TECHNICAL FIELD

The present invention relates to a phosphazene compound, a photosensitive resin composition, and usage thereof. More specifically, the present invention relates to (i) a phosphazene compound obtained by reacting a phenoxyphosphazene compound and/or a cross-linked phenoxyphosphazene compound with an epoxy compound having an unsaturated double bond and/or an isocyanate compound, (ii) a photosensitive resin composition which allows water system development, formation of a favorable pattern shape, and simplification of production steps, particularly, a photosensitive resin composition which uses phosphazene flame retardants having a phenolic hydroxyl group and allows a cured resin film to have a superior flame retardancy, and (iii) usage thereof.

BACKGROUND ART

Recently, with rapid improvement in performances and functions and rapid decrease in sizes and weights of electronic devices, electronic parts used in these electronic devices are required to have smaller sizes, lighter weights, and smaller thickness. Thus, on a print wiring board which is to be provided with electronic parts, it is required to install a semiconductor or the like in a high density manner, to make wires finer, and it is required to make the print wiring board multi-layered in order to reduce sizes and weights of the electronic parts and improve functions and performances of the electronic parts. In order to support finer wirings, it is necessary to use an insulative material having high electric insulation property for protecting the wirings. Further, as the print wiring substrate on which the electric parts are provided, a flexible print wiring board (referred to also as FPC as required) has recently attracted more attentions than an ordinary rigid print wiring board, and has come to be further demanded. Further, a resin is used as a material for various products such as an electric product, an automobile, and the like, due to its characteristics such as easiness to fabricate, mechanical property, electric property, appearance, and the like.

Incidentally, in producing the print wiring board, a photosensitive material is used in various manners. That is, the photosensitive material is used in (i) formation of circuit patterned on the print wiring board (pattern circuit), (ii) formation of a protection layer for protecting a surface and the pattern circuit of the print wiring board, (iii) formation of an insulation layer between layers in case where the print wiring board has a plurality of layers, (iv) and the like. As the photosensitive material used in these purposes, a liquid photosensitive material and a film photosensitive material are used. Among them, the film photosensitive material has such advantage that its film thickness is evener and its workability is more excellent than the liquid photosensitive material. Thus, various film photosensitive materials are used according to usages such as a pattern circuit resist film used to form a pattern circuit, a photosensitive cover lay film used to form the protection layer, a photosensitive dry film resist used to form the interlayer insulation layer, and the like.

For example, a polymer film referred to as a cover lay film is combined with a surface of the FPC so as to protect a conductive surface. As a process for combining the cover lay film with the conductor surface, it is general to perform the following process: The cover lay film, processed so as to have a predetermined shape, whose one side has an adhesive, is made to overlap the FPC and is properly positioned, and then the cover lay film is thermally pressed against the FPC with a pressing device or the like. However, as the foregoing adhesive, an epoxy adhesive or an acrylic adhesive is mainly used, but such adhesive is inferior in soldering heat resistance, bonding strength at high temperature, and flexibility. Thus, in case of combining the cover lay film with the conductor surface with an adhesive, it is impossible to sufficiently make use of a performance of the polyimide film.

Further, in case of combining the cover lay film with the FPC with the conventional epoxy adhesives or acrylic adhesives, it is necessary to form a hole or a window on an uncombined cover lay film so as to correspond to a junction of a terminal or a part of the circuit. However, the cover lay film is thin, so that it is difficult to form a hole and the like. Furthermore, the hole and the like of the cover lay film are almost manually positioned so as to correspond to junctions of terminals or portions of the FPC. This is not preferable in terms of workability and positional accuracy, and the manufacturing cost increases.

In order to improve the workability and the positional accuracy, conventionally, (i) a method for forming a protection layer by applying a photosensitive composition to the conductor surface and (ii) a photosensitive cover lay film (the photosensitive dry film resist is used as a cover lay film) have been developed, thereby improving the workability and the positional accuracy.

However, acrylic resins are used in the photosensitive cover lay film, so that its heat resistance property and durability of the film are not sufficient, and the film has no flame retardancy. That is, as the photosensitive cover lay film and the photosensitive dry film resist (hereinafter, both of them are generically referred to as a photosensitive dry film resist), merely acrylic or epoxy photosensitive dry film resists are focused at present, but there is such a problem that the film having been cured is inferior in heat resistance, chemical resistance, anti-bending property, and flame retardancy. In this way, the resin is more likely to burn than a metallic material or an inorganic material, so that improvement of the flame retardancy remains unrealized.

A general method for realizing the flame retardancy is a method in which a compound having a halogen is mixed. An example thereof is a photosensitive dry film resist produced by curing a photosensitive resin composition containing a bromic flame retardant (for example, Patent Document 1). However, the photosensitive dry film resist recited in Patent Document 1 contains the bromic flame retardant, so that the flame retardant having a halogen may have a bad influence on the environment. Further, the flame retardant having a halogen gives a great load to the environment, so that study on non-halogenous (halogen-free) materials is carried out all over the world. Thus, the halogen-free flame retardant is being studied instead of the bromic flame retardant (for example, Patent Documents 2, 3, and 4). As the halogen-free flame retardant, nitrogenous, phosphorus, and inorganic compounds, phosphate ester hydrate, red phosphorus hydrate, metal oxide hydrate, and the like, are known. However, phosphate ester and red phosphorus are hydrolyzed which may results in occurrence of phosphoric acid, and they are likely to drop electric reliability. The metal oxide scatters and absorbs light, so that it is difficult to use the metal oxide as the photosensitive resin.

Further, recently, a flame retardant using a resin to which a silicone compound has been added has been being studied (for example, Patent Document 5). Further, as a flame retardant, phosphazene compounds are being studied, and it is known that the phosphazene compounds exhibit high flame retardant effect (for example, Patent Document 7). Patent Document 7 discloses a flame retardant resin composition obtained by blending a phosphazene compounds with a polycarbonate resin and the like. The phosphazene compounds have an excellent effect in improving the flame retardancy, and has such an advantage that the phosphazene compounds give less load to the environment since this is a halogen-free flame retardant.

Further, conventionally, polyimide resin materials which can be bonded at low temperature and in short time and are superior in heat resistance have been proposed (for example, Patent Document 8). Further, as polyimide adhesive materials favorably used in production of the FPC, a material having photosensitivity has been proposed (for example, Patent Document 9). Also a laminate having not only flexibility but also heat resistance has been disclosed (for example, Patent Document 10). Incidentally, a resin material used in the wiring board is required to have flame retardancy as described above, and various kinds of resin materials whose flame retardancy has been improved are proposed (for example, Patent Document 11). Among them, it is more preferable to use a resin material having a phosphorus compound in order to avoid use of a material, giving some load to the environment, as much as possible.

[Patent Document 1]
Japanese Unexamined Patent Publication No. 335619/2001 (Tokukai 2001-335619)(Publication date: Dec. 4, 2001)
[Patent Document 2]
Japanese Unexamined Patent Publication No. 235001/2002 (Tokukai 2002-235001)(Publication date: Aug. 23, 2002)
[Patent Document 3]
Japanese Unexamined Patent Publication No. 19930/2001 (Tokukai 2001-19930)(Publication date: Jan. 23, 2001)
[Patent Document 4]
Japanese Unexamined Patent Publication No. 49090/2001 (Tokukai 2001-49090)(Publication date: Feb. 20, 2001)
[Patent Document 5]
Japanese Unexamined Patent Publication No. 40219/2001 (Tokukai 2001-40219)(Publication date: Feb. 13, 2001)
[Patent Document 6]
Japanese Unexamined Patent Publication No. 40149/2001 (Tokukai 2001-40149)(Publication date: Feb. 13, 2001)
[Patent Document 7]
Japanese Unexamined Patent Publication No. 181268/1999 (Tokukaihei 11-181268)(Publication date: Jul. 6, 1999)
[Patent Document 8]
Japanese Unexamined Patent Publication No. 242820/1995 (Tokukaihei 7-242820)(Publication date: Sep. 19, 1995)
[Patent Document 9]
Japanese Unexamined Patent Publication No. 27667/1994 (Tokukaihei 6-27667)(Publication date: Feb. 4, 1994)
[Patent Document 10]
Japanese Unexamined Patent Publication No. 733/1998 (Tokukaihei 10-733)(Publication date: Jan. 6, 1998)
[Patent Document 11]
Japanese Unexamined Patent Publication No. 335703/2001 (Tokukai 2001-335703)(Publication date: Dec. 4, 2001)

However, in case of using the nitrogenous compound, the phosphorus compound, or the inorganic compound as the halogen-free flame retardant, the nitrogenous compound generally has some influence on a curing property of the resin, and the phosphorus compound drops humidity resistance or has a similar influence, so that it is difficult to practically use each of these compounds. Thus, there are less choices of flame retardant materials which can be used in the photosensitive dry film resist required to have an electric insulation property and anti-hydrolysis property.

Further, also in case of using as the flame retardant the resin to which the silicone compound has been added, few kinds of resins can exhibit the flame retardant effect. Further, the flame retardant to which the silicone compound has been independently added rarely exhibits a great flame retardant effect, and even the flame retardant whose effect can be confirmed to some extent requires addition of a large quantity of silicone compounds in order to satisfy a strict flame retardant standard. As a result, a bad influence is exerted onto other necessary properties of the resin, so that this results in disadvantage in cost. Thus, use of such flame retardant is not practical.

Further, even in case of using the phosphazene compound as the flame retardant, when a resin obtained by mixing a conventional phosphazene compound is used in a cover lay film or the like, the phosphazene compound is deposited (bled or juiced) on a surface of the resin, so that properties of the resin drop. For example, conventionally used propoxylated phosphazene is in a liquid state, so that a bonding property of the photosensitive dry film resist cured after being treated at high temperature significantly drops.

Further, the resin is used for resin parts used in electric and electronic parts. In terms of environmental problems, solder containing no lead (lead-free solder) is practically used in a print wiring board on which the resin parts are installed. In case of using the lead-free solder, reflow temperature rises (250° C. to 260° C.), so that the resin parts are required to have sufficient heat resistance. However, in case of using the resin obtained by mixing the conventional phosphazene compound as the flame retardant, the phosphazene compound evaporates and disappears at such high temperature. Thus, a flame retardant which more persistently remains in the resin is required.

Further, a photo-curing resin which is cured by irradiation of an energy line such as an ultraviolet ray is practically used in various fields represented by a coating material field and an electric/electronic material field instead of a conventional thermosetting resin. As a compound which gives flame retardancy to the resin, an acrylic compound having a halogen and a compound having a double bond, e.g., a phosphate ester compound which is likely to be hydrolyzed, are known. However, each of these compounds has such a problem that this exerts a great load to the environment and such a problem that its hydrolysis property is low.

The present invention was made in view of the foregoing problems, and an object of the present invention is to provide (i) a phosphazene compound which allows water system development, formation of a favorable pattern shape, and realization of not only properties such as heat resistance, hydrolysis property, easiness to process (inclusive of solvent solubility), and bonding property, but also photosensitivity, flame retardancy, and sufficient mechanical strength, the phosphazene compound being favorably used to produce a wiring substrate for sufficiently supporting reduction of a size and a weight of each electronic part of an electronic device, and (ii) a photosensitive resin composition using the phosphazene compound, and (iii) typical usage thereof.

DISCLOSURE OF INVENTION

The inventors of the present invention diligently studied so as to solve the foregoing problems. As a result of the study, they found it preferable to use as a flame retardant a phosphazene compound obtained by reacting a specific phenoxyphosphazene compound (A-1) and/or a cross-linked phenoxyphosphazene compound (A-2) with a specific epoxy compound (B) and/or an isocyanate compound (C), particularly, they found it possible to realize excellent balance of flame retardancy, photosensitivity, and other properties in case of using the phosphazene compound as a flame retardant of a photosensitive resin composition.

That is, a phosphazene compound according to the present invention is obtained by reacting a phenoxyphosphazene compound (A-1) having a phenolic hydroxyl group and/or a cross-linked phenoxyphosphazene compound (A-2) obtained by cross-linking the phenoxyphosphazene compound (A-1) with an epoxy compound (B) having an unsaturated double bond and/or an isocyanate compound (C), wherein the phosphazene compound has an unsaturated double bond in its molecule.

It is preferable to arrange the phosphazene compound so that the phenoxyphosphazene compound (A-1) is a circular phenoxyphosphazene compound (A-11) represented by formula (1)

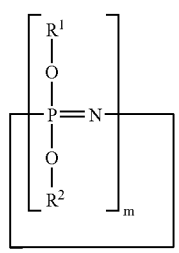

(1)

where m represents an integer ranging from 3 to 25, and each of $R^1$ and $R^2$ represents a phenyl group or a hydroxyphenyl group, and a single molecule has one or more hydroxyphenyl groups.

Further, it is preferable to arrange the phosphazene compound so that the phenoxyphosphazene compound (A-1) is a chain phenoxyphosphazene compound (A-12) represented by formula (2)

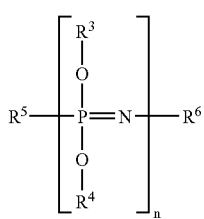

(2)

where n represents an integer ranging from 3 to 10000, and each of $R^3$ and $R^4$ represents a phenyl group or a hydroxyphenyl group, and a single molecule has one or more hydroxyphenyl groups, and $R^5$ represents —N=P(OC$_6$H$_5$)$_3$, —N=P(OC$_6$H$_5$)$_2$(OC$_6$H$_4$OH), —N=P(OC$_6$H$_5$)(OC$_6$H$_4$OH)$_2$, —N=P(OC$_6$H$_4$OH)$_3$, —N=P(O)OC$_6$H$_5$, or —N=P(O)(OC$_6$H$_4$OH), and $R^6$ represents —P(OC$_6$H$_5$)$_4$, —P(OC$_6$H$_5$)$_3$(OC$_6$H$_4$OH), —P(OC$_6$H$_5$)$_2$(OC$_6$H$_4$OH)$_2$, —P(OC$_6$H$_5$)(OC$_6$H$_4$OH)$_3$, —P(OC$_6$H$_4$OH)$_4$, —P(O)(OC$_6$H$_5$)$_2$, —P(O)(OC$_6$H$_5$)(OC$_6$H$_4$OH), or —P(O)(OC$_6$H$_4$OH)$_2$.

Further, it is preferable to arrange the phosphazene compound so that the cross-linked phenoxyphosphazene compound (A-2) is obtained by cross-linking the phenoxyphosphazene compound (A-1) on the basis of a phenylene cross-linking group having at least one of an o-phenylene group, a m-phenylene group, a p-phenylene group, and a bisphenylene group represented by formula (3)

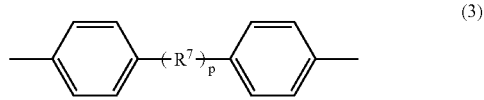

(3)

where $R^7$ represents —C(CH$_3$)$_2$—, —SO$_2$—, —S—, or —O—, and p represents 0 or 1.

Further, it is preferable to arrange the phosphazene compound so that the cross-linked phenoxyphosphazene compound (A-2) is a phenylene cross-linked phenoxyphosphazene compound (A-3) in which the circular phenoxyphosphazene compound (A-11) and/or the chain phenoxyphosphazene compound (A-12) is used as the phenoxyphosphazene compound, and the phenylene cross-linking group intervenes between two oxygen atoms obtained by desorbing a phenyl group and a hydroxyphenyl group from the phenoxyphosphazene compound (A-1) so that a ratio at which the phenyl group and the hydroxyphenyl group are contained in the cross-linked phenoxyphosphazene compound ranges from 50 to 99.9% with respect to a total of a phenyl group and a hydroxyphenyl group of the phenoxyphosphazene compound, the phenylene cross-linked phenoxyphosphazene compound (A-3) including at least one phenolic hydroxyl group.

A photosensitive resin composition according to the present invention includes at least the phosphazene compound having any one of the foregoing arrangements and a soluble polyimide resin (D) which is soluble in an organic solvent. It is preferable to arrange the photosensitive resin composition so that further includes a photoreaction initiator (E-1). Further, a photosensitive resin composition according to the present invention includes at least the phosphazene compound having any one of the foregoing arrangements and a photoreaction initiator (E-1). It is preferable to arrange the photosensitive resin composition so that further includes a compound having a carbon-carbon double bond (E-4).

Further, it is preferable to arrange the photosensitive resin composition so that 1 wt % or more of the soluble polyimide resin (D) is dissolved in at least one kind of an organic solvent selected from dioxolane, dioxane, tetrahydrofuran, N,N-dimethylformamide, N,N-dimethylacetamide, and N-methyl-2-pyrrolidone at temperature ranging from room temperature to 100° C.

The usage of the photosensitive resin composition according to the present invention is not particularly limited, but an example thereof is a photosensitive resin film produced by using the photosensitive resin composition. The photosensitive resin film can be used as a print wiring adhesive film, a photosensitive cover lay film, a print wiring board insulative protection film, or a print wiring board substrate.

As described above, the phosphazene compound according to the present invention is obtained by reacting a phenoxyphosphazene compound (A-1) having a phenolic hydroxyl group and/or a cross-linked phenoxyphosphazene compound (A-2) obtained by cross-linking the phenoxyphosphazene compound (A-1) with an epoxy compound (B) having an unsaturated double bond and/or an isocyanate compound (C), wherein the phosphazene compound has an unsaturated double bond in its molecule.

Further, as described above, the photosensitive resin composition according to the present invention includes at least the phosphazene compound and a soluble polyimide resin (D) which is soluble in an organic solvent. Alternatively, the photosensitive resin composition according to the present invention includes at least the phosphazene compound and a photoreaction initiator (E-1).

Therefore, the phosphazene compound and the photosensitive resin composition including the phosphazene compound are excellent not only in the heat resistance, the dielectric property, and the flame retardancy, but also the easiness to process since bonding can be carried out with the photosensitive resin composition at temperature lower than temperature at which bonding is carried out with a conventional thermoplastic polyimide resin adhesive. Moreover, a specific polyimide resin is used, so that the photosensitive resin composition has more preferable balance than a conventional polyimide/epoxy resin mixture adhesive in properties such as the easiness to process, the heat resistance, and the dielectric property. Thus, the photosensitive resin composition according to the present invention allows bonding at lower temperature than that in a conventional one, and is excellent in the easiness to process and the treatability, and can exhibit excellent heat resistance, dielectric property, and flame retardancy.

As a result, in case where the photosensitive resin composition according to the present invention is formed in a solution state like varnish, the photosensitive resin composition can be used as a resin chemical product such as an adhesive, a coating agent, or an ink. Further, in case where the photosensitive resin composition according to the present invention is formed in a resin sheet or a resin film, the photosensitive resin composition can be favorably used as a print wiring board (FPC) adhesive sheet, a photosensitive cover lay film, a print wiring board insulative circuit protection film, or a print wiring board substrate.

Further, as a result of diligent study on the foregoing problems, the inventors of the present invention found that: by selecting a combination of a specific polyimide resin (G), a specific phosphazene compound (H), and a specific (meth)acrylic compound (I) as a component of the photosensitive resin composition, it is possible to realize excellent balance of the flame retardancy and other properties. As a result, they completed the present invention.

That is, a photosensitive resin composition according to the present invention has at least a polyimide resin (G) and a phosphazene compound (H), and the photosensitive resin composition includes: a soluble polyimide resin (G-1), which has a carboxyl group and/or a hydroxyl group and is soluble in an organic solvent, as the polyimide resin (G); and a phenoxyphosphazene compound (H-1) having a phenolic hydroxyl group and/or a cross-linked phenoxyphosphazene compound (H-2), which is obtained by cross-linking the phenoxyphosphazene compound (H-1) and has at least one phenolic hydroxyl group, as the phosphazene compound (H), and the photosensitive resin composition further includes a (meth)acrylic compound (I).

It is preferable to arrange the photosensitive resin composition so that the phenoxyphosphazene compound (H-1) includes a circular phenoxyphosphazene compound (H-11) represented by formula (1)

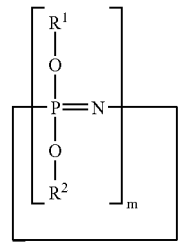

where m represents an integer ranging from 3 to 30, and each of R1 and R2 represents a phenyl group or a hydroxyphenyl group, and a single molecule has one or more hydroxyphenyl groups.

Further, it is preferable to arrange the photosensitive resin composition so that the phenoxyphosphazene compound (H-1) includes a chain phenoxyphosphazene compound (H-12) represented by formula (2)

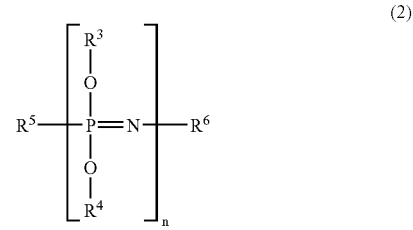

where n represents an integer ranging from 3 to 10000, and each of $R^3$ and $R^4$ represents a phenyl group or a hydroxyphenyl group, and a single molecule has one or more hydroxyphenyl groups, and $R^5$ represents —N=P(OC$_6$H$_5$)$_3$, —N=P(OC$_6$H$_5$)$_2$(OC$_6$H$_4$OH), —N=P(OC$_6$H$_5$)(OC$_6$H$_4$OH)$_2$, —N=P(OC$_6$H$_4$OH)$_3$, —N=P(O)OC$_6$H$_5$, or —N=P(O)(OC$_6$H$_4$OH), and $R^6$ represents —P(OC$_6$H$_5$)$_4$, —P(OC$_6$H$_5$)$_3$(OC$_6$H$_4$OH), —P(OH$_6$H$_5$)$_2$(OC$_6$H$_4$OH)$_2$, —P(OC$_6$H$_5$)(OC$_6$H$_4$OH)$_3$, —P(OC$_6$H$_4$OH)$_4$, —P(O)(OC$_6$H$_5$)$_2$, —P(O)(OC$_6$H$_5$)(OC$_6$H$_4$OH), or —P(O)(OC$_6$H$_4$OH)$_2$.

It is preferable to arrange the photosensitive resin composition so that the cross-linked phenoxyphosphazene compound (H-2) is obtained by cross-linking the phenoxyphosphazene compound (H-1) on the basis of a phenylene cross-linking group having at least one of an o-phenylene group, a m-phenylene group, a p-phenylene group, and a bisphenylene group represented by formula (3)

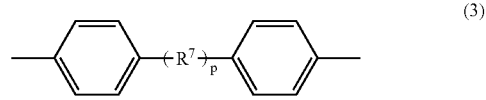

where $R^7$ represents —C(CH$_3$)$_2$—, —SO$_2$—, —S—, or —O—, and p represents 0 or 1.

It is more preferable to arrange the photosensitive resin composition so that the cross-linked phenoxyphosphazene compound (H-2) is a phenylene cross-linked phenoxyphosphazene compound (H-2 1) in which the circular phenoxyphosphazene compound (H-11) and/or the chain phenoxyphosphazene compound (H-12) is used as the phenoxyphosphazene compound, and the phenylene crosslinking group intervenes between two oxygen atoms obtained by desorbing a phenyl group and a hydroxyphenyl group from the phenoxyphosphazene compound (H-1) so that a ratio at which the phenyl group and the hydroxyphenyl group are contained in the cross-linked phenoxyphosphazene compound ranges from 50 to 99.9% with respect to a total of a phenyl group and a hydroxyphenyl group of the phenoxyphosphazene compound, said phenylene cross-linked phenoxyphosphazene compound (H-21) including at least one phenolic hydroxyl group.

It is preferable to arrange the photosensitive resin composition so that the soluble polyimide resin (G-1) has at least one kind of an unsaturated double bond selected from an acryl group, a methacryl group, a vinyl group, and an allyl group.

Further, it is preferable to arrange the photosensitive resin composition so that an amount of the phosphazene compound (H) ranges from 1 to 100 parts by weight with respect to 100 parts by weight corresponding to a total weight of the polyimide resins (G) and the (meth)acrylic compound (I).

The usage of the photosensitive resin composition according to the present invention is not particularly limited, but an example thereof is a photosensitive resin film produced by using the photosensitive resin composition. In the photosensitive resin film, in case of using 1 wt % of sodium hydroxide whose temperature is 40° C. as a developer and using a spray developing device as developing means, it is preferable that dissolving time under a spray pressure of 0.85 MPa is 180 seconds or less. Further, the photosensitive resin composition according to the present invention can be used as a pattern circuit resist film, a photosensitive cover lay film, or a photosensitive dry film resist.

As described above, the photosensitive resin composition according to the present invention includes at least the soluble polyimide resin (G-1.) and the phenoxyphosphazene compound (H-1) or the cross-linked phenoxyphosphazene compound (H-2), and includes the (meth)acrylic compound (I).

Therefore, the phosphazene compound arranged in the foregoing manner and the photosensitive resin composition having the phosphazene compound are excellent not only in the photosensitivity, the heat resistance, the dielectric property, and the flame retardancy, but also the easiness to process since bonding can be carried out with the photosensitive resin composition at temperature lower than temperature at which bonding is carried out with a conventional thermoplastic polyimide resin adhesive. Moreover, a specific polyimide resin is used, so that the photosensitive resin composition has more preferable balance than a conventional polyimide/epoxy resin mixture adhesive in properties such as the easiness to process, the heat resistance, and the dielectric property. Further, the photosensitive resin composition according to the present invention has an excellent developing property in a basic aqueous solution. Thus, the photosensitive resin composition according to the present invention allows bonding at lower temperature than that in a conventional one, and is excellent in the easiness to process and the treatability, and can exhibit excellent heat resistance, dielectric property, and flame retardancy.

As a result, in case where the photosensitive resin composition according to the present invention is formed in a solution state like varnish, the photosensitive resin composition can be used as a resin chemical product such as an adhesive, a coating agent, or an ink. Further, in case where the photosensitive resin composition according to the present invention is formed in a photosensitive resin film, the photosensitive resin composition can be favorably used as a pattern circuit resist film, a photosensitive cover lay film, or a photosensitive dry film resist.

Further, as a result of diligent study on the foregoing problems, the inventors of the present invention found that: it is possible to achieve a predetermined object by using (i) a photosensitive resin composition including a soluble polyimide resin (K) having a carboxyl group and/or a hydroxyl group, a specific phenoxyphosphazene compound (L), and a (meth)acrylic compound (I) and (ii) a photosensitive dry film resist produced by using the photosensitive resin composition. As a result, they completed the present invention.

That is, the present invention relates to a photosensitive resin composition includes a soluble polyimide resin (K) having a carboxyl group and/or a hydroxyl group, a phenoxyphosphazene compound (L), and a (meth)acrylic compound (M), and the phenoxyphosphazene compound (L) includes at least one of a circular phenoxyphosphazene compound (L-1) represented by formula (22) and a chain phenoxyphosphazene compound (L-2) represented by formula (23),

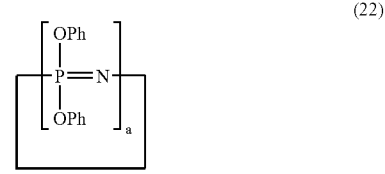

where a represents an integer ranging from 3 to 30,

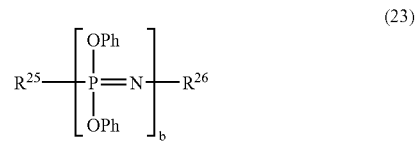

where $R^{25}$ represents group-N=P(OPh)$_3$ or group-N=P(O)OPh, and $R^{26}$ represents group-P(OPh)$_4$ or group-P(O)(OPh)$_2$, and b represents an integer ranging from 3 to 10000, wherein the phenoxyphosphazene compound (L) includes a cross-linked phenoxyphosphazene compound (L-3) having a structure cross-linked by causing a cross-linking group having any one of an o-phenylene group, an m-phenylene group, a p-phenylene group, and a bisphenylene group represented by formula (3) to intervene between two oxygen atoms obtained by desorbing a phenyl group,

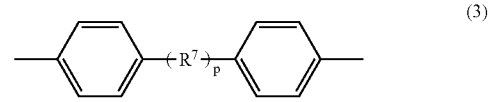

where $R^7$ represents —C(CH$_3$)$_2$—, —SO$_2$—, —S—, or —O—, and p represents 0 or 1.

It is preferable to arrange the photosensitive resin composition so that a soluble polyimide resin serving as the component (K) has at least one kind of a carbon-carbon double bond selected from an acryl group, a methacryl group, a vinyl group, and an allyl group.

Further, it is preferable to arrange the photosensitive resin composition so that an amount of the component (L) ranges from 1 to 100 parts by weight with respect to 100 parts by weight corresponding to a total weight of the components (K) and (L).

Further, the present invention relates to a photosensitive dry film resist produced by using the photosensitive resin composition recited in any one of the foregoing arrangements.

It is preferable to arrange the photosensitive dry film resist so that: in case of using 1 wt % of sodium hydroxide whose temperature is 40° C. as a developer and using a spray developing device as developing means, dissolution time under a spray pressure of 0.85 MPa is 180 seconds or less.

Further, the present invention relates to a print wiring board using the photosensitive dry film resist as an insulative protection layer.

Additional objects, features, and strengths of the present invention will be made clear by the description below. Further, the advantages of the present invention will be evident from the following explanation in reference to the drawings.

BEST MODE FOR CARRYING OUT THE INVENTION

Embodiment 1

Figure 1:
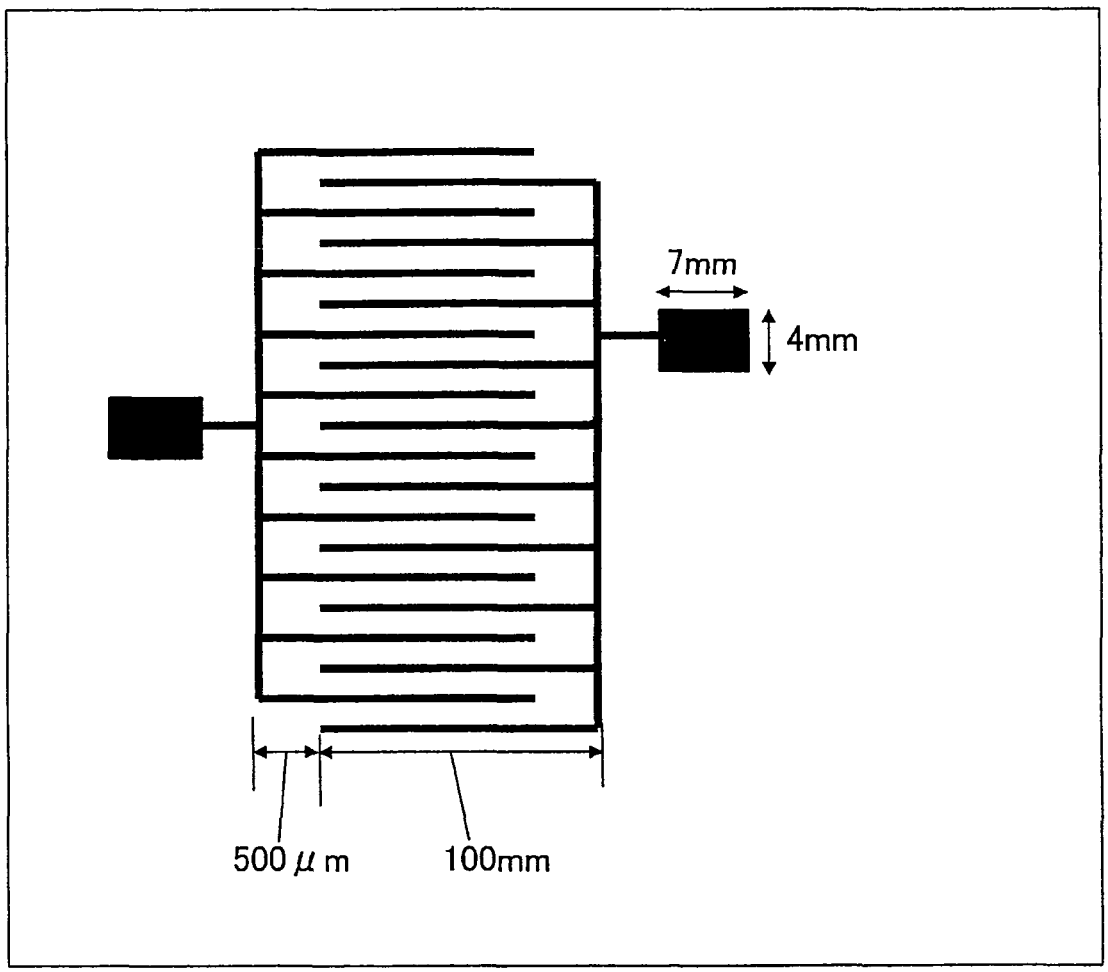
FIG. 1 is a schematic illustrating a comb-shape pattern used in Examples of the present invention.

The following will explain Embodiment 1 of the present invention. Note that, the present invention is not limited to this.

(A) Phosphazene Compound

The phosphazene compound according to the present invention is a compound obtained by reacting a phenoxyphosphazene compound (A-1) having a phenolic hydroxyl group, and/or a cross-linked phenoxyphosphazene compound (A-2) obtained by cross-linking the phenoxyphosphazene compound (A-1), and/or an isocyanate compound (C), and the phosphazene compound has an unsaturated double bond in its molecule.

The phenoxyphosphazene compound (A-1) and/or the cross-linked phenoxyphosphazene compound (A-2) are included, so that it is possible to give flame retardancy without losing the heat resistance of the obtained photosensitive resin composition. Particularly, the phosphazene compound used in the present invention has a phenolic hydroxyl group in its molecule, so that the phenolic hydroxyl group remarkably improves compatibility with respect to the soluble polyimide resin. Thus, in the obtained photosensitive resin composition, it is possible to suppress deposition (bleeding or juicing) of the flame retardant on the surface, thereby further improving the flame retardancy.

Moreover, the phenolic hydroxyl group is included in the molecule, so that the phosphazene compound allows formation of a mesh structure by reacting particularly with an epoxy resin component (described later) in curing the photosensitive resin composition. Thus, efficient curing is possible, thereby obtaining a cured product having excellent heat resistance. Further, it is also possible to improve alkaline solubility compared with the conventional phosphazene compound.

Note that, hereinafter, the phosphazene compound according to the present invention, that is, the phosphazene compound which is obtained by reacting the phenoxyphosphazene compound (A-1), and/or the cross-linked phenoxyphosphazene compound (A-2), the epoxy compound (B), and/or the isocyanate compound (C) and has an unsaturated double bond in its molecule is referred to as a double bond phosphazene compound for ease of description.

[Phenoxyphosphazene Compound (A-1)]

The phenoxyphosphazene compound (A-1) used in synthesis of the double bond phosphazene compound according to the present invention is not particularly limited as long as the phenolic hydroxyl group is included. Specifically, it is preferable to use at least one of a circular phenoxyphosphazene compound (A-11) and a chain phenoxyphosphazene compound (A-12).

First, the circular phenoxyphosphazene compound (A-11) has a structure represented by the following formula (1)

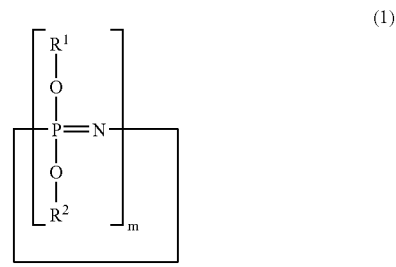

(1)

where m represents an integer ranging from 3 to 25, and each of $R^1$ and $R^2$ represents a phenyl group or a hydroxyphenyl group ($—C_6H_4OH$), and a single molecule has one or more hydroxyphenyl groups.

Next, the chain phenoxyphosphazene compound (A-12) has a structure represented by the following formula (2)

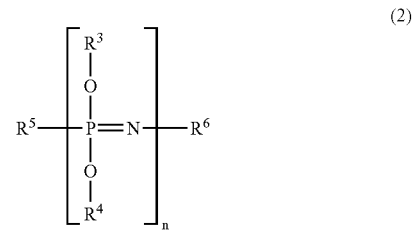

(2)

where n represents an integer ranging from 3 to 10000, and each of $R^3$ and $R^4$ represents a phenyl group or a hydroxyphenyl group, and a single molecule has one or more hydroxyphenyl groups, and $R^5$ represents $—N=P(OC_6H_5)_3$, $—N=P(OC_6H_5)_2(OC_6H_4OH)$, $—N=P(OC_6H_5)(OC_6H_4OH)_2$, $—N=P(OC_6H_4OH)_3$, $—N=P(O)OC_6H_5$, or $—N=P(O)(C_6H_4OH)$, and $R^6$ represents $—P(OC_6H_5)_4$, $—P(OC_6H_5)_3(OC_6H_4OH)$, $—P(OC_6H_5)2(OC_6H_4OH)_2$, $—P(OC_6H_5)(OC_6H_4OH)_3$, $—P(OC_6H_4OH)_4$, $—P(O)(OC_6H_5)_2$, $—P(O)(OC_6H_5)(OC_6H_4OH)$, or $—P(O)(OC_6H_4OH)_2$.

Each of the circular phenoxyphosphazene compound (A-11) and the chain phenoxyphosphazene compound (A-12) has excellent compatibility with respect to the soluble polyimide resin and the epoxy resin (described later), and allows the obtained photosensitive resin composition to have excellent heat resistance after being cured.

A production process of the circular phenoxyphosphazene compound (A-11) and the chain phenoxyphosphazene compound (A-12) is not particularly limited, but specific examples of the production process are recited in the following documents.

Document A: Engineering/Chemistry Magazine, Vol. 67, No. 9, p.1378 (1964), Masaaki Yokoyama et al.

Document B: Engineering/Chemistry Magazine, Vol. 73, No. 6, p.1164 (1970), Tomoya Okuhashi et al.

Document C: Japanese Unexamined Patent Publication No. 219190/1983 (Tokukaisho 58-219190)

Document D: Alessandro Medici, et al., Macromolecules, Vol. 25, No. 10, p. 2569 (.1992)

Document E: Japanese Unexamined Patent Publication No. 145394/1979 (Tokukaisho 54-145394)

Document F: Japanese Unexamined Patent Publication No. 145395/1979 (Tokukaisho 54-145395)

For example, a compound in which one hydroxyl group of bivalent phenol is protected by a methyl group or a benzyl group (for ease of description, the compound is referred to as a protected phenol compound) is synthesized as in 4-methoxyphenol, 4-(benzyloxy)phenol, etc., and an alkaline metallic salt (e.g., lithium salt, sodium salt, potassium salt, and the like) of the compounds is obtained. The alkaline metallic salt (4-methoxyphenol alkaline metallic salt or 4-(benzyloxy)phenol alkaline metallic salt) of the obtained protected phenol compound is reacted with phosphonitryl chloride recited in Documents E and F. Thereafter, the resultant is reacted with pyridine halogenoid hydracid salt or tribromoboron etc. so as to deprotect the methyl group or the benzyl group, thereby carrying out conversion into the hydroxyl group. This treatment allows synthesis of the foregoing phenoxyphosphazene compound.

Further, as to the phenoxyphosphazene compound, in case of producing a compound having a phenoxy group partially substituted by a hydroxyl group, alkaline metal of the protected phenol compound and/or alkaline metallic salt of hydroxyalkylphenol are obtained, and alkaline metallic salt of alcoholic or phenolic compound is used at the same time as reaction with phosphonitryl chloride.

It is preferable to use the phenoxyphosphazene compound (A-1) since it is possible to give not only flame retardancy and high soldering-heat resistance but also excellent electric insulation property to the photosensitive resin film obtained by curing the photosensitive resin composition without using any halogen compound.

[Example of Synthesis (Production) of phenoxyphosphazene compound (A-1)]

The following explains a specific example of synthesis (production) of the circular phenoxyphosphazene compound (A-11) and the chain phenoxyphosphazene compound (A-12).

First, at least one kind of a dichlorophosphazene compound selected from a circular dichlorophosphazene compound represented by the following formula (4) and a straight chain or chain dichlorophosphazene compound represented by the following formula (5) is used as a material phosphazene compound

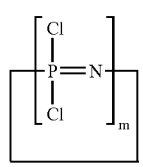

(4)

where m represents an integer ranging from 3 to 25

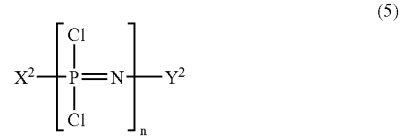

(5)

where $X^2$ represents —N=PCl$_3$ or —N=P(O)Cl, and $Y^2$ represents —PCl$_4$ or —P(O)Cl$_2$, and n represents an integer ranging from 3 to 10000.

Then, alkaline metallic phenolate represented by the following formula (6) or (7) is reacted with the compound represented by the formula (4) or (5). Note that, in alkaline metallic phenolate represented by the formula (7), a position of an alkyloxy group (methoxy group) is not particularly limited.

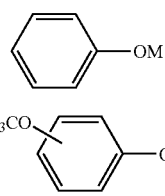

(6)

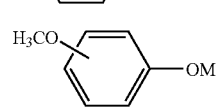

(7)

where M represents alkaline metal.

Due to the reaction, it is possible to introduce the phenyl group and the methoxyphenyl group into the structure represented by the formula (4) or (5). At this time, in the structure represented by the formula (4) or (5), it is necessary that at least one methoxyphenyl group is introduced into a single molecule. In other words, in case of reacting the compound represented by the formula (4) or (5) with the compounds represented by the formulas (6) and (7), it is necessary to define a reaction condition including an amount (molar ratio conversion) of the compound of the formula (7) so that at least one methoxyphenyl group is introduced into a single molecule. Note that, a detail reaction condition is not particularly limited, but a known condition is adopted.

In the compound obtained through the foregoing reaction, the reaction with pyridine halogenoid hydracid salt or tribromoboron etc. causes the methoxyphenyl group to be deprotected, thereby carrying out conversion into a hydroxyl group. The operation results in the synthesis of the circular phenoxyphosphazene compound (A-11) represented by the formula (1) and the chain phenoxyphosphazene compound (A-12) represented by the formula (2).

[Cross-linked phenoxyphosphazene Compound (A-2)]

As described above, the cross-linked phenoxyphosphazene compound (A-2) used in the synthesis of the double bond phosphazene compound according to the present invention has at least one phenolic hydroxyl group, and is a phosphazene compound obtained by cross-linking the phenoxyphosphazene compound (A-1). The cross-linked phenoxyphosphazene compound (A-2) may be obtained in any manner as long as the phenoxyphosphazene compound (A-1) is cross-linked with a known cross-linking group. However, it is preferable to cross-link the phenoxyphosphazene compound (A-1) with phenylene cross-linking groups.

The phenylene cross-linking groups are not particularly limited as long as each cross-linking group has a phenyl group in its structure. However, a specific example thereof is a cross-linking group having at least any one of an o-phenylene group, an m-phenylene group, and a p-phenylene group,

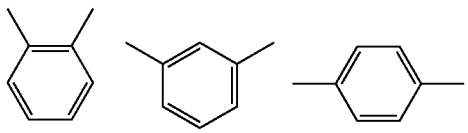

or a bisphenylene group represented by the following formula (3)

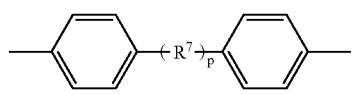
(3)

where $R^7$ represents —C(CH$_3$)$_2$—, —SO$_2$—, —S— or —O—, and p represents 0 or 1.

In the present invention, in case of synthesizing (producing) the cross-linked phenoxyphosphazene compound, any compound corresponding to the phenoxyphosphazene compound may be used, but it is preferable to use the circular phenoxyphosphazene compound (A-11) and/or the chain phenoxyphosphazene compound (A-12).

Further, in case where (1) the circular phenoxyphosphazene compound (A-11) and/or the chain phenoxyphosphazene compound (A-12) are used as the phenoxyphosphazene compound and (2) the phenylene cross-linking groups are used as the cross-linking group, when these conditions are satisfied, it is preferable to define a cross-linking condition so as to satisfy the following conditions (3) and (4).

That is, it is preferable that: (3) the phenylene cross-linking groups intervene between two oxygen atoms obtained by desorbing a phenyl group and a hydroxyphenyl group from the circular phenoxyphosphazene compound (A-11) and/or the chain phenoxyphosphazene compound (A-12), and (4) a ratio at which the phenyl group and the hydroxyphenyl group are included in the cross-linked phenoxyphosphazene compound ranges from 50 to 99.9% with respect to a total of a phenyl group and a hydroxyphenyl group of the foregoing phenoxyphosphazene compound.

When the cross-linked phenoxyphosphazene compound (A-2) satisfying the conditions (1) to (4) is used, it is possible to further improve the flame retardancy of the heat-resistance resin composition. Note that, the cross-linked phenoxyphosphazene compound satisfying the conditions (1) to (4) is referred to as phenylene cross-linked phenoxyphosphazene compounds (A-3).

[Example of Synthesis (Production) of Cross-linked phenoxyphosphazene Compound (A-2)]

A production process of the cross-linked phenoxyphosphazene compound (A-2) is not particularly limited, but an example of the synthesis process thereof is described as follows by taking the phenylene cross-linked phenoxyphosphazene compounds (A-3) as an example.

First, the dichlorophosphazene compound represented by the formula (4) or (5) is reacted with alkaline metallic phenolate. As the alkaline metallic phenolate used at this time, not only the alkaline metallic phenolate represented by the formula (6) or (7) but also alkaline metallic diphenolate represented by the following formula (8) or (9)

(8)

(9)

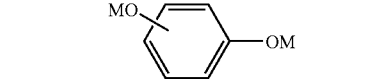

where M represents alkaline metal, and $R^7$ represents —C(CH$_3$)$_2$—, —SO$_2$—, —S— or —O—, and p represents 0 or 1.

A compound obtained in this manner has a structure in which: a methoxyphenyl group (and a phenyl group) is introduced into the structure represented by the formula (4) or (5), and the structure represented by the formula (4) or (5) is cross-linked by the alkaline metallic diphenolate represented by the formula (8) or (9). Thereafter, due to reaction with pyridine halogenoid hydracid salt or tribromoboron, the methyl group or the benzyl group is deprotected, thereby carrying out conversion into a hydroxyl group. On this account, it is possible to obtain a compound obtained by cross-linking the phenoxyphosphazene compound represented by the formula (1) and/or the formula (2) with aromatic diol, that is, it is possible to obtain the phenylene cross-linked phenoxyphosphazene compounds (A-3).

An amount of the phenoxyphosphazene compound (inclusive of the cross-linked resultant) blended is not particularly limited, but it is preferable that the amount ranges from 0.1 to 50 wt % with respect to 100 wt % (total weight) of the heat-resistance resin composition. When the amount is less than 0.1 wt %, the flame retardant effect may drop. When the amount exceeds 50 wt %, the bonding property may drop or the dynamic property may drop.

[Epoxy Compound (B)]

The following explains the epoxy compound (B) having an unsaturated double bond used in the synthesis of the phosphazene compound according to the present invention.

Any material may be used as the epoxy compound (B) according to the present invention as long as the compound has an epoxy group and an unsaturated double bond in its molecule. However, specific examples thereof include glycidyl methacrylate, glycidyl acrylate, allyl glycidyl ether, glycidyl vinyl ether, or a compound etc. represented by the following formula (10). where r represents an integer ranging from 0 to 40, and R.sup.8 represents H or a methyl group. These compounds may be independently used, or a suitable combination of two or more kinds may be used.

The following explains reaction between the phenoxyphosphazene compound (A-1) (the circular phenoxyphosphazene compound (A-11) having a phenolic hydroxyl group and/or the chain phenoxyphosphazene compound (A-12) having a phenolic hydroxyl group) and the epoxy compound (B) having an unsaturated double bond, that is, the following explains synthesis (production) of a double-bond phosphazene compound according to the present invention.

First, the phenoxyphosphazene compound (A-1) and the epoxy compound (B) are dissolved in an organic solvent. Preferable examples of the organic solvent include: aromatics such as benzene, toluene, and xylene; ethers such as ether, tetrahydrofuran, and dioxane; N-substituted amides such as N,N-dimethylformamide; and the like. These organic solvents may be independently used, or a suitable combination of two or more kinds may be used. Note that, in case where the phenoxyphosphazene compound (A-1) melts at reaction temperature, it is possible to carry out the synthesis without any solvent.

A solution obtained by dissolving the phenoxyphosphazene compound (A-1) and the epoxy compound (B) is reacted in the presence of tertiary amine such as pyridine triethylamine at temperature ranging from room temperature or higher to reflux temperature or lower of the solvent for one to 20 hours. Further, in case of using no solvent, the epoxy compound (B) is dissolved in the phenoxyphosphazene compound (A-1) having melted, the thus obtained solution is reacted at temperature ranging from room temperature or higher to reflux temperature or lower of the phenoxyphosphazene compound (A-1). On this account, it is possible to obtain the double-bond phosphazene compound according to the present invention. Note that, it is possible to add a known stabilizer at the time of reaction.

In the foregoing reaction, it may be so arranged that: a reaction amount of the phenoxyphosphazene compound (A-1) having a phenolic hydroxyl group and the epoxy compound (B) having an unsaturated double bond is adjusted so as to react all the phenolic hydroxyl groups of the phenoxyphosphazene compound with the epoxy compound (B) having an unsaturated double bond. Further, in case of using the double-bond phosphazene compound according to the present invention as the photosensitive resin composition, it may be so arranged that: a phosphazene compound in which a phenolic hydroxyl group is left without reacting all the phenolic hydroxyl groups of the phosphazene compound with the epoxy compound (B) having an unsaturated double bond so as to improve the solubility in the alkaline aqueous solution serving as the developer.

An amount of the epoxy compound (B) blended is not more than three times larger, more preferably 2.5 times larger than the phenolic hydroxyl group of the phenoxyphosphazene compound (A-1) in terms of a molar ratio. Further, a lower limit of the amount of the epoxy compound (B) blended may be determined depending on an amount of the unsaturated double bond introduced into the phosphazene compound. The amount of the unsaturated double bond introduced into the phosphazene compound is preferably at least 1, more preferably 1.2 or more for each molecule of the phosphazene compound. Thus, it is preferable to add the epoxy compound (B) of 1 or more mol for each mol of the phosphazene compound, and it is more preferable to add the epoxy compound (B) of 1.2 or more mol for each mol of the phosphazene compound.

[Isocyanate Compound (C)]

The following explains the isocyanate compound (C) having an unsaturated double bond which is used to synthesize the double bond phosphazene compound according to the present invention.

Any compound may be used as the isocyanate compound (C) according to the present invention as long as the compound has an isocyanate group and an unsaturated double bond in its molecule. Specific examples thereof include methacryloylisocyanate, acryloylisocyanate, methacryloylethylisocyanate, acryloylethylisocyanate, methacryloxyethylisocyanate, acryloxyethylisocyanate, vinyldimethylbenzylisocyanate, m-isopropenyl-α, α-dimethylbenzylisocyanate, 2-methacryloyloxyethylisocyanate, and the like. These compounds may be independently used, or a suitable combination of two or more kinds may be used.

The following describes how the phenoxyphosphazene compound (A-1) (the circular phenoxyphosphazene compound (A-11) having a phenolic hydroxyl group and/or the chain phenoxyphosphazene compound (A-12) having a phenolic hydroxyl group) is reacted with the isocyanate compound (C) having an unsaturated double bond, that is, the following describes synthesis (production) of the double bond phosphazene compound according to the present invention.

First, the phenoxyphosphazene compound (A-1) and the isocyanate compound (C) are dissolved in an organic solvent. As the organic solvent, it is possible to use: N-substituted amides such as N,N-dimethylformamide, N,N-diethylformamide, N-methylformanilide, N-formylpiperidine, N,N-dimethylacetamide, N,N-diethylacetamide, N,N-dimethylpropanamide, N-methyl-α-pyrrolidone, N-methyl-α-piperidone, and N-methylcaprolactam; N-substituted ureas such as N-tetramethylurea, N-acetyl-α-pyrrolidone, N-acetyl-α-piperidone, and N-acetylcaprolactam; N-substituted thioureas such as N-tetramethylthiourea; sulfoxides such as dimethylsulfoxide, tetramethylenesulfoxide, diethylsulfoxide, diisopropylsulfoxide, di-n-propylsulfoxide, diisobutylsulfoxide, and di-n-butylsulfoxide; and N-substituted phosphorylamides such as hexamethylphosphorylamide and hexaethylphosphorylamide; aromatics such as benzene, toluene, and xylene; ethers such as ether, tetrahydrofuran, and dioxane; and the like. These organic solvents may be independently used, or a suitable combination of two or more kinds may be used. Note that, in case of melting the phenoxyphosphazene compound (A-1) at reaction temperature, it is possible to carry out the operation without any solvent.

A solution obtained by dissolving the phenoxyphosphazene compound (A-1) and the isocyanate compound (C) is reacted at temperature ranging from room temperature or higher to reflux temperature or lower for one to 20 hours. In case of carrying out the reaction without any solvent, the isocyanate compound (C) is dissolved in the melted phenoxyphosphazene compound (A-1), and the thus obtained solution is reacted at temperature ranging from room temperature or higher to reflux temperature or lower of the phenoxyphosphazene compound (A-1). In this manner, it is possible to obtain the double bond phosphazene compound according to the present invention. Note that, at the time of the reaction, it is possible to add a known stabilizer.

It may be so arranged that: a reaction amount of the phenoxyphosphazene compound (A-1) having a phenolic hydroxyl group and the isocanate compound (C) having an unsaturated double bond is adjusted so as to react all the phenolic hydroxyl groups of the phenoxyphosphazene compound with the isocyanate compound having the unsaturated double bond. Further, in case of using the phosphazene compound of the present invention as a photosensitive resin composition, it may be so arranged that: a phosphazene compound in which the phenolic hydroxyl groups are left is obtained without reacting all the phenolic hydroxyl groups of the phosphazene compound with the isocyanate compound having the unsaturated double bond so as to improve the solubility in the alkaline aqueous solution serving as the developer.

An amount of the isocyanate compound (C) blended is not more than three times larger, more preferably 2.5 times larger than the phenolic hydroxyl group of the phenoxyphosphazene compound (A-1) in terms of a molar ratio. Further, a lower limit of the amount of the isocyanate compound (C) blended may be determined depending on an amount of the unsaturated double bond introduced into the phosphazene compound. The amount of the unsaturated double bond introduced into the phosphazene compound is preferably at least 1, more preferably 1.2 or more for each molecule of the phosphazene compound. Thus, it is preferable to add the isocyanate compound (C) of 1 or more mol for each mol of the phosphazene compound, and it is more preferable to add the isocyanate compound (C) of 1.2 or more mol for each mol of the phosphazene compound.

In the foregoing example, the phenoxyphosphazene compound (A-1) and/or the cross-linked phenoxyphosphazene compound (A-2) are reacted with the epoxy compound (B) or the isocyanate compound (C) in synthesizing the double bond phosphazene compound according to the present invention. However, the double bond phosphazene compound according to the present invention may be synthesized by reacting the phenoxyphosphazene compound (A-1) and/or the cross-linked phenoxyphosphazene compound (A-2) with the epoxy compound (B) and the isocyanate compound (C). A reaction condition at this time is not particularly limited, and a suitable combination of the reaction conditions explained in [Isocyanate compound (C)] may be adopted.

Photosensitive Resin Composition (D)

The photosensitive resin composition according to the present embodiment includes at least the double bond phosphazene compound and polyimide resins (E). Among them, a soluble polyimide resin (E-1) having a carboxyl group and/or a hydroxyl group and being soluble in an organic solvent is used as the polyimide resins (E).

[Polyimide Resins (E)]

As the polyimide resins according to the present embodiment, at least the soluble polyimide resin (E-1) is used. The soluble polyimide resin (E-1) of the present invention is a resin having a carboxyl group and/or a hydroxyl group in its side chain and being soluble in an organic solvent, and the term "soluble polyimide resin" is an expediential term used to describe such a polyimide resin.

[Soluble Polyimide Resin (E-1)]

As described above, the "solubility" of the soluble polyimide resin (E-1) means a condition under which the resin is soluble in the organic solvent. More specifically, this condition is as follows: 1 wt % or more of the resin is dissolved in at least one kind of an organic solvent selected from dioxolane, dioxane, tetrahydrofuran, N,N-dimethylformamide, N,N-dimethylacetamide, and N-methyl-2-pyrrolidone at temperature ranging from room temperature to 100° C.

Any resin may be used as the soluble polyimide resin (E-1) as long as the resin has an imide ring as a recurring unit in its structure. Specifically, not only polyimide (resin having only an imide ring: polyimide resin in a narrow sense) but also polyamidimide, polyesterimide, polyetherimide, maleimide, and the like each of which has a recurring unit other than the imide ring are used as the polyimide resin in a broad sense.

Here, the soluble polyimide resin (E-1) is generally produced by the following two methods. In the first method, an acid dianhydride component and a diamine component are used as monomer components serving as materials of the soluble polyimide resin (E-1), and the monomer components are reacted with each other so as to polymerize polyamide acid (polyamic acid), and the polyamide acid (polyamic acid) is imidized, thereby obtaining the soluble polyimide resin. In the second method, an acid dianhydride component and an isocyanate component are used as monomer components serving as materials of the soluble polyimide resin (E-1), and these monomer components are reacted with each other, thereby obtaining the soluble polyimide resin.

Specific arrangement of the soluble polyimide resin (E-1) is not particularly limited. However, in the present invention, an acid dianhydride having a specific structure described later, diamine, or isocianate are used as the monomer components, thereby obtaining a soluble polyimide resin (D) which is more favorable in producing the photosensitive resin composition according to the present invention. A production method of the soluble polyimide resin (E-1) will be described later.

Note that, in the first method, it is necessary to carry out imidization in case of using polyamide acid, and it is necessary to expose the resultant at high temperature exceeding 250° C. for a long time, so that portions other than a copper foil or polyimide may deteriorate. However, it is preferable to use the imidized resultant in the soluble polyimide resin (E-1) according to the present invention. In this case, there is no deterioration in the photosensitive resin composition.

<Acid Dianhydride Component>

In the soluble polyimide resin (E-1) favorably used in the present invention, the acid dianhydride component is not particularly limited as long as acid dianhydride is used, but specific examples thereof include: aliphatic or alicyclic tetra carboxylate dianhydride such as 2,2'-hexafluoropropyliden diphthalate dianhydride, 2,2-bis(4-hydroxy phenyl)propane dibenzoate-3,3',4,4'-tetracarboxylate dianhydride, butane tetracarboxylate dianhydride, 1,2,3,4-cyclobutane tetracarboxylate dianhydride, 1,3-dimethyl-1,2,3,4-cyclobutane tetracarboxylate dianhydride, 1,2,3,4-cyclopentane tetracarboxylate dianhydride, 2,3,5-tricarboxycyclopentyl acetic acid dianhydride, 3,5,6-tricarboxynorbornane-2-acetic acid dianhydride, 2,3,4,5-tetrahydrofuran tetracarboxylate dianhydride, 5-(2,5-dioxotetrahydrofural)-3-methyl-3-cyclohexane-1, 2-dicarboxylate dianhydride, and bicyclo[2,2,2]-octo-7-ene-2,3,5,6-tetracarboxylate dianhydride; and aromatic tetracarboxylate dianhydride such as pyromellitic acid dianhydride, 3,3',4,4'-benzophenone tetracarboxylate dianhydride, 3,3',4,4'-biphenylsulfone tetracarboxylate dianhydride, 1,4,5,8-naphthalene tetracarboxylate dianhydride, 2,3,6,7-naphthalene tetracarboxylate dianhydride, 3,3',4,4'-biphenylether tetracarboxylate dianhydride, 3,3',4,4'-dimethyldiphenylsilane tetracarboxylate dianhydride, 3,3',4,4'-tetraphenylsilane tetracarboxylate dianhydride, 1,2,3,4-furan tetracarboxylate dianhydride, 4,4'-bis(3,4-dicarboxyphenoxy)diphenylsulfide dianhydride, 4,4'-bis(3,4-dicarboxyphenoxy)diphenylsulfone dianhydride, 4,4'-bis(3,4-dicarboxyphenoxy)diphenylpropane dianhydride, 4,4'-bis(3,4-dicarboxyphenoxy)diphenylpropane dianhydride, 3,3',4,4'-perfluoroisopropyliden diphthalic acid dianhydride, 3,3',4,4'-biphenyltetracarboxylate dianhydride, bis(phthalic acid)phenylphosphinoxide dianhydride, p-phenylene-bis(triphenyl phthalic acid)dianhydride, m-phenylene-bis(triphenyl phthalic acid)dianhydride, bis(triphenyl phthalic acid)-4,4'-diphenylether dianhydride, and bis(triphenyl phthalic acid)-4,4'-diphenylmethane dianhydride; and the like. These tetracarboxylate dianhydrides may be independently used, or a suitable combination of two or more kinds may be used.

Particularly, it is preferable to select one of structures represented by the following formulas (11) and (12) in order to express the heat resistance and the mechanical property at a high level.

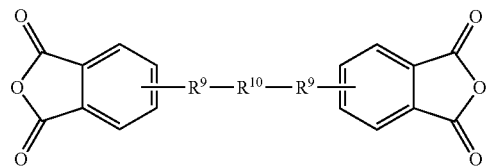

(11)

-continued (12)

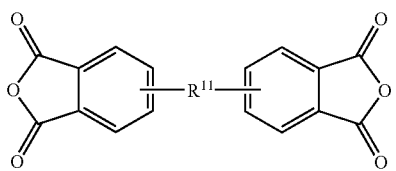

where $R^9$ represents an ester bond or an ether bond, and $R^{10}$ represents a binary organic group.

Particularly, it is preferable to use an acid dianhydride having a structure selected from the followings (13).

(13)

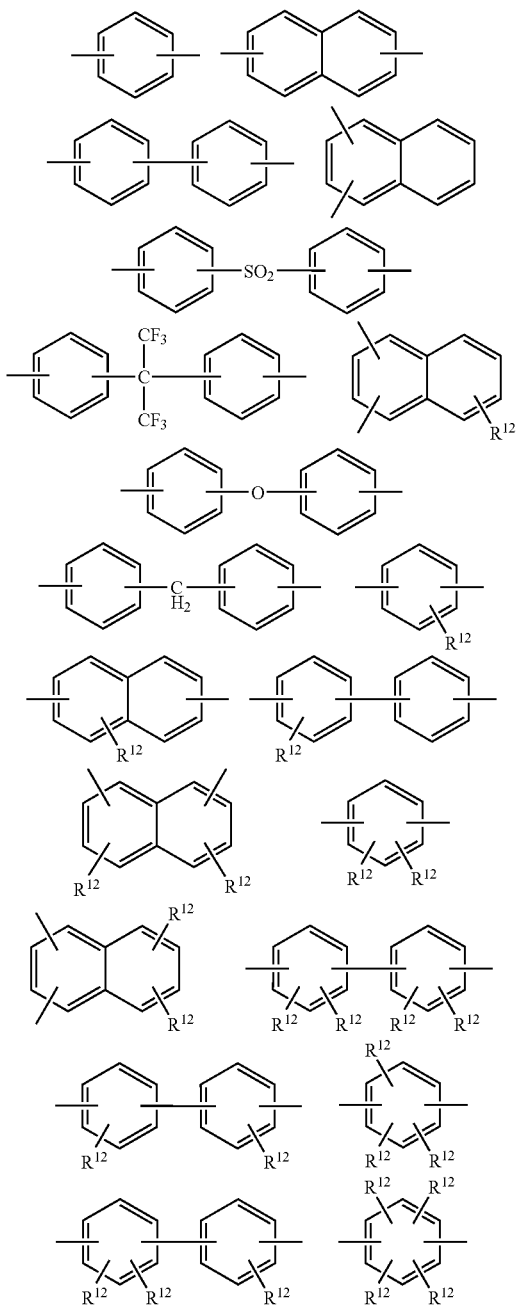

-continued

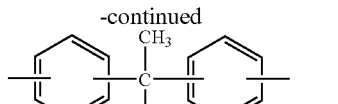

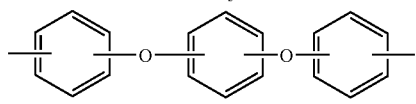

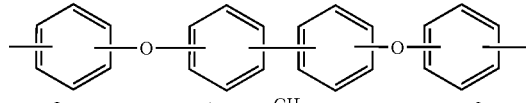

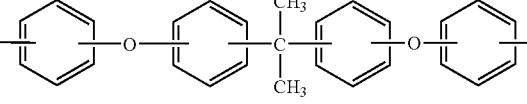

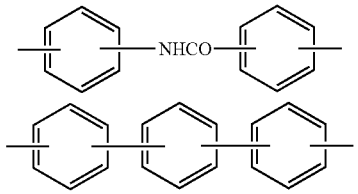

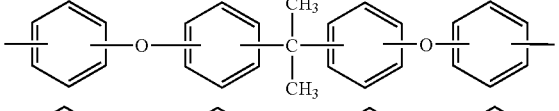

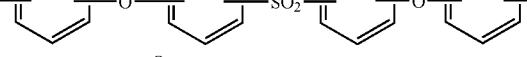

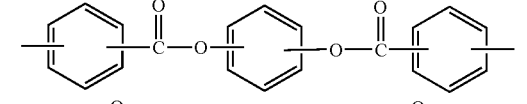

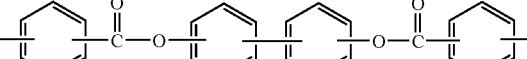

where $R^{12}$ represents hydrogen, halogen, a methoxy or an alkyl group containing 1 to 16 carbon atoms. Further, $R^{11}$ represents —O—, —CH$_2$—, —(C=O)—, —C(CH$_3$)$_2$—, —C(CF$_3$)$_2$—, or —SO$_2$—.

In order to obtain the soluble polyimide resin whose solubility in the organic solvent is high, it is preferable to use, in the compound represented by the formula (11) or (12), parts of 2,2'-hexafluoropropyliden diphthalic acid dianhydride, 2,3,3',4'-biphenyltetracarboxylate dianhydride, 4,4-(4,4'-isopropylidendiphenoxy)bisphthalic acid, 2,2-bis(4-hydroxyphenyl)propandibenzoate-3,3',4,4'-tetracarboxylate dianhydride.

<Diamine Component>

In the soluble polyimide resin (E-1) favorably used in the present invention, the diamine component used as a material is not particularly limited as long as diamine is used. However, as the developer used to develop the photosensitive resin, an aqueous solution, particularly, an alkaline aqueous solution developer comes to be used instead of an organic solvent developer since the organic solvent developer has some influence on the environment. Thus, in the present embodiment, in order to carry out the development with the alkaline aqueous solution, it is preferable to use diamine having one or two carboxyl groups or one or two hydroxyl groups in its molecule (for ease of description, this diamine is referred to as hydroxydiamine) as the diamine component constituting the soluble polyimide resin. On this account, it is possible to obtain the soluble polyimide resin having a carboxyl group or a hydroxyl group, thereby carrying out the development with the alkaline aqueous solution.

As the hydroxydiamine, any diamine may be used as long as the diamine has two carboxyl groups. However, specific examples thereof include: diamino phthalic acids such as 2,5-diamino terephthalic acid; carboxy biphenyl compounds such as 3,3'-diamino-4,4'-dicarboxy biphenyl, 3,3'-diamino-4,4'-dicarboxybiphenyl, 4,4'-diamino-3,3'-dicarboxybiphenyl, 4,4'-diamino-2,2'-dicarboxybiphenyl, and 4,4'-diamino-2,2',5,5'-tetradicarboxybiphenyl; carboxy diphenylalkanes such as carboxydiphenylmethane such as 3,3'-diamino-4,4'-dicarboxydiphenylmethane, 2,2-bis[3-amino-4-carboxyphenyl]propane, 2,2-bis[4-amino-3-carboxyphenyl]propane, 2,2-bis[3-amino-4-carboxyphenyl]hexafluoropropane, and 4,4'-diamino-2,2',5,5'-tetracarboxydiphenylmethane; carboxydiphenylether compound such as 3,3'-diamino-4,4'-dicarboxydiphenylether, 4,4'-diamino-3,3'-dicarboxydiphenylether, 4,4'-diamino-2,2'-dicarboxydiphenylether, and 4,4'-diamino-2,2',5,5'-tetracarboxydiphenylether; diphenyl sulfone compound such as 3,3'-diamino-4,4'-dicarboxydiphenylsulfone, 4,4'-diamino-3,3'-dicarboxydiphenylsulfone, 4,4'-diamino-2,2'-dicarboxydiphenylsulfone, and 4,4'-diamino-2,2',5,5'-tetracarboxydiphenylsulfone; bis[(carboxy phenoxy)phenyl]alkane compounds such as 2,2-bis[4-(4-amino-3-carboxyphenoxy)phenyl]propane; bis[(carboxy phenoxy)phenyl]sulfone compound such as 2,2-bis[4-(4-amino-3-carboxyphenoxy)phenyl]sulfone; and the like. These diamines each of which has two carboxyl groups may be independently used, or a suitable combination of two or more kinds may be used.

Further, it is preferable that a COOH equivalent (carboxylic acid equivalent) of the soluble polyimide resin (E-1) of the present invention ranges from 300 to 3000. This is realized by using the diamine having a carboxyl group as a material for the soluble polyimide resin (E-1). A carboxylic acid equivalent of the soluble polyimide resin (E-1) preferably ranges from 350 to 2500, more preferably from 350 to 2000. It is not preferable that the carboxylic acid equivalent exceeds 3000 since it is difficult to dissolve the polyimide in the aqueous solution alkaline developer and it takes longer time to carry out the development under this condition. Note that, the carboxylic acid equivalent means an average molecular weight for each carboxylic acid. For example, when 5 millimole of carboxylic acid is included in 1 g, the carboxylic acid equivalent is 200. Further, for example, in a resin having 1000 recurring units, when two carboxylic acids are included in each recurring unit, the carboxylic acid equivalent is 500.

Note that, in case where diamine having two or more carboxyl groups is used, it is possible to realize the carboxylic acid equivalent of 300 or less. However, it is necessary to use a monomer whose molecular weight is large to some extent in order to realize a structure having high solubility, so that it is preferable that the carboxylic acid equivalent is 300 or more.

In order to realize the favorable carboxylic acid equivalent, it is preferable to use diamine having two or more carboxyl groups in its molecule. When the diamine is used, it is possible to realize a predetermined carboxylic acid equivalent even in case where another kind of diamine is copolymerized, and it is easier to design properties, so that this arrangement is preferable. When the aforementioned carboxylic acid equivalent is satisfied, it is possible to use also diamine, such as 3,5-diamino benzoic acid, having one carboxyl group.

Further, the hydroxydiamine is not particularly limited as long as diamine has two hydroxyl groups. However, specific examples thereof include: hydroxybiphenyl compounds such as 4,6-diaminoresorcinol, 3,3'-diamino-4,4'-dihydroxybiphenyl, 4,4'-diamino-3,3'-dihydroxybiphenyl, 4,4'-diamino-2,2'-dihydroxybiphenyl, and 4,4'-diamino-2,2',5,5'-tetrahydroxybiphenyl; hydroxyl diphenylalkanes such as hydroxydiphenylmethane such as 3,3'-diamino-4,4'-dihydroxydiphenylmethane, 4,4'-diamino-3,3'-dihydroxydiphenylmethane, 4,4'-diamino-2,2'-dihydroxydiphenylmethane, 2,2-bis[3-amino-4-hydroxy phenyl]propane, 2,2-bis[4-amino-3-hydroxy phenyl]propane, 2,2-bis[3-amino-4-hydroxy phenyl]hexafluoropropane, and 4,4'-diamino-2,2',5,5'-tetrahydroxydiphenylmethane; hydroxy diphenylether compounds such as 3,3'-diamino-4,4'-hydroxy diphenylether, 4,4'-diamino-3,3'-dihydroxydiphenylether, 4,4'-diamino-2,2'-dihydroxydiphenylether, and 4,4'-diamino-2,2',5,5'-tetrahydroxydiphenylether; diphenylsulfone compounds such as 3,3'-diamino-4,4'-dihydroxydiphenylsulfone, 4,4'-diamino-3,3'-dihydroxydiphenylsulfone, 4,4'-diamino-2,2'-dihydroxydiphenylsulfone, and 4,4'-diamino-2,2',5,5'-tetrahydroxydiphenylsulfone; bis[(hydroxy phenoxy)biphenyl]alkane compounds such as 2,2-bis[4-(4-amino-3-hydroxyphenoxy)phenyl]propane; bis(hydroxyphenoxy) biphenyl compounds such as 4,4'-bis(4-amino-3-hydroxyphenoxy)biphenyl; bis[(hydroxyphenoxy)phenyl] sulfone compounds such as 2,2-bis [4-(4-amino-3-hydroxyphenoxy)phenyl]sulfone; bis(hydroxyphenoxy) biphenyl compounds such as 4,4'-diamino-3,3'-dihydroxydiphenylmethane, 4,4'-diamino-2,2'-dihydroxydiphenylmethane, 2,2-bis[3-amino-4-hydroxyphenyl]propane, and 4,4'-bis(4-amino-3-hydroxyphenoxy)biphenyl; and the like. These diamines each of which has two hydroxyl groups may be independently used, or a suitable combination of two or more kinds may be used.

Further, it is possible to use also diamine having one hydroxyl group as the hydroxydiamine. Specific examples thereof include diaminophenols such as 2,4-diaminophenol and the like.

Further, an OH equivalent (hydroxyl group equivalent) of the soluble polyimide resin (E-1) of the present invention preferably ranges from 250 to 3000, more preferably from 300 to 2000, most preferably from 300 to 1500. It is not preferable that the hydroxyl group equivalent exceeds 3000 since it is difficult to dissolve the resin in the alkaline aqueous solution and it is difficult to carry out the development. Further, it is not preferable that the hydroxyl group equivalent is less than 250 since the heat resistance drops and the resin is likely to absorb the moisture due to a large amount of water-absorptive hydroxyl groups. Note that, the hydroxyl group equivalent is an average molecular weight for each hydroxyl group. For example, when 5 millimole of hydroxyl groups are included in 1 g, the hydroxyl group equivalent is 200. Further, for example, in a resin having 1000 recurring units, when two hydroxyl groups are included in each recurring unit, the hydroxyl group equivalent is 500.

Further, there is a case where it is preferable to use not only the hydroxydiamine but also diamine having a siloxane bond (—Si—O—) (for ease of description, this diamine is referred to as siloxanediamine) as the diamine component constituting the soluble polyimide resin (E-1). A specific example of the siloxanediamine is a compound represented by the following formula (14)

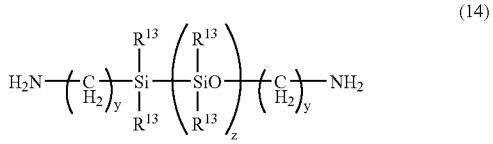

(14)

where $R^{13}$ represents an alkyl group containing 1 to 12 carbon atoms, or a phenyl group, and y represents an integer ranging from 1 to 40, and z represents an integer ranging from 1 to 20. When the siloxanediamine is used, it is possible to improve the solubility of the thus obtained soluble polyimide resin (E-1) in the organic solvent. Further, it is preferable to use the siloxanediamine represented by the formula (14) since it is possible to obtain the soluble polyimide resin having high flexibility and high solubility.

In the formula (14), favorable examples of $R^{13}$ are a methyl group, an ethyl group, and a phenyl group. A particularly preferable one is the methyl group. Further, it is more preferable that z is an integer ranging from 2 to 10, and it is particularly preferable that z is an integer ranging from 2 to 5. It is more preferable that y is an integer ranging from 4 to 30, and it is further more preferable that y is an integer ranging from 5 to 20, and it is particularly preferable that y is an integer ranging from 8 to 15. As to the range of y, its influence on properties of the soluble polyimide resin is great. When y is a small value, the obtained soluble polyimide resin is likely to be less flexible, and when y is excessively large, the obtained soluble polyimide resin is likely to have less heat resistance. Further, in all the diamine components, a molar ratio of the siloxanediamine preferably ranges from 5 to 70 mol %, more preferably from 10 to 50 mol %.

Further, any material may be used to constitute the soluble polyimide resin (E-1) as long as the material is diamine, and diamine other than the hydroxydiamine and the siloxanediamine may be used. Specific examples of other diamine include: aromatic diamine such as p-phenylene diamine, m-phenylene diamine, 4,4'-diamino diphenylmethane, 4,4'-diaminodiphenylethane, 4,4'-diaminodiphenyl ether, 4,4'-diaminodiphenyl sulfide, 4,4'-diaminodiphenyl sulfone, 1,5-diaminonaphthalene, 3,3-dimethyl-4,4'-diamino biphenyl, 5-amino-1-(4'-aminophenyl)-1, 3,3-trimethyl indan, 6-amino-1-(4'-amino phenyl)-1,3,3-trimethyl indan, 4,4'-diaminobenzanilide, 3,5-diamino-3'-trifluoromethyl benzanilide, 3,5-diamino-4'-trifluoromethyl benzanilide, 3,4'-diamino diphenylether, 2,7-diamino fluorene, 2,2-bis(4-aminophenyl)hexafluoropropane, 4,4'-methylene-bis(2-chloro aniline), 2,2',5,5'-tetra chloro-4,4'-diamino biphenyl, 2,2'-dichloro-4,4'-diamino-5,5'-dimethoxy biphenyl, 3,3'-dimethoxy-4,4'-diamino biphenyl, 4,4'-diamino-2,2'-bis(trifluoromethyl)biphenyl, 2,2-bis[4-(4-amino phenoxy)phenyl] propane, 2,2-bis[4-(4-amino phenoxy)phenyl] hexafluoropropane, 1,4-bis(4-amino phenoxy)benzene, 4,4'-bis(4-amino phenoxy)-biphenyl, 1,3'-bis(4-amino phenoxy) benzene, 9,9-bis(4-amino phenyl)fluorene, 4,4'-(p-phenylene isopropyliden)bisaniline, 4,4'-(m-phenylene isopropyliden) bisaniline, 2,2'-bis[4-(4-amino-2-trifluoromethyl phenoxy) phenyl]hexafluoropropane, and 4,4'-bis[4-(4-amino-2-trifluoromethyl)phenoxy]-octafluorobiphenyl; aromatic diamine having (i) two amino groups coupled to an aromatic ring such as diaminotetraphenylthiophene and (ii) a hetero atom other than a nitrogen atom of each amino group; aliphatic diamine such as 1,1-methaxylylene diamine, 1,3-propanediamine, tetramethylene diamine, pentamethylene diamine, octamethylene diamine, nanomethylene diamine, 4,4-diamino heptamethylene diamine, 1.4-diamino cyclohexane, isophorone diamine, tetrahydro dicyclopentadienylene diamine, hexahydro-4,7-methanoindanylene dimethylene diamine, tricyclo [6,2,1,02.7]-undecylene dimethyl diamine, and 4,4'-methylenebis(cyclohexylamine); and the like. These diamines may be independently used, or a suitable combination of two or more kinds may be used.

In case of using the aromatic diamine, it is advantageous, in designing the photosensitive resin composition, to use diamine having an amino group in an m-position (3-) since the soluble polyimide resin itself is likely to less absorb light at g-line and i-line areas.

<Synthesis of Soluble Polyimide Resin (E-1)>

The soluble polyimide resin (E-1) used in the present invention can be produced in accordance with a known method. Specifically, the synthesis method (production method) of the soluble polyimide resin (E-1) is roughly divided into two methods depending on materials used.

In the first method, an acid dianhydride component and a diamine component are used as materials (monomers), and these monomer components are condensed so as to synthesize polyamide acid (polyamic acid) serving as a precursor, and these resultants are chemically or thermally subjected to dehydration cyclization (imidization). In this manner, the first method is a two-step method. While, in the second method, an acid dianhydride component and an isocyanate component are used as materials, and these monomer components are polymerized, thereby obtaining the polyimide resin. In this manner, the second method is a single-step method.

The following description details the first method in which synthesis (production) of polyamide acid and imidization of the polyamide acid are carried out and details the second method.

<Synthesis (Production) Method of Polyamide Acid in the First Method>

The synthesis (production) method of polyamide acid is a method in which an acid dianhydride component containing at least one kind of acid dianhydride is reacted with a diamine component containing at least one kind of diamine in an organic solvent. At this time, the acid dianhydride component and the diamine component are blended with each other so that they are substantially identical with each other in a molar ratio. Thus, in case of using only one kind of acid dianhydride and only one kind of diamine, it is necessary only to blend them so that they are substantially identical with each other in a molar ratio. In case of two or more kinds of acid dianhydrides and two or more kinds of diamines, it is necessary only to blend them so that a total amount of the acid dianhydride components (total amount of plural acid dianhydrides) and a total amount of the diamine components (total amount of plural diamines) are substantially identical with each other in a molar ratio. In case of using plural acid dianhydrides and plural diamines, it is possible to intentionally obtain a polyamide acid copolymer.

In the synthesis of the polyamide acid, the method for reacting the monomer components is not particularly limited, but it is general that: after dissolving in the organic solvent the acid dianhydride component and the diamine component which are substantially identical with each other in a molar ratio, the resultant is stirred until completion of polymerization while controlling various reaction conditions. According to the method, it is possible to obtain a solution through dissolution of the polyamide acid in the organic solvent (hereinafter, the solution is referred to as a polyamide acid solution).

An example of an order in which the acid dianhydride component and the diamine component are added is as follows: (1) the diamine component is dissolved in the organic solvent and then the acid dianhydride component is added thereto; (2) the acid dianhydride component is dissolved in the organic solvent and then the diamine component is added thereto; and (3) a proper amount of diamine component is added to and dissolved in the organic solvent, and the acid dianhydride component whose amount exceeds the amount of the diamine component is added thereto, and a diamine component whose amount corresponds to the excess of the added acid dianhydride is added thereto; and so on. However, the order is not particularly limited. Note that, "dissolve" means not only a condition under which a solvent completely dissolves a substance but also a condition under which the substance is evenly dispersed or diffused in the solvent so as to be substantially dissolved in the solvent.

A synthesis condition in the synthesis reaction of the polyamide acid is not particularly limited as long as polymerization of the monomer components sufficiently enables synthesis of the polyamide acid. In the present invention, as to the synthesis conditions, it is preferable to define a temperature condition, a reaction time, and an organic solvent to be used, as follows.

First, the temperature condition under which synthesis reaction of the polyamide acid is carried out is not particularly limited as long as the temperature range allows polymerization of the acid dianhydride component and the diamine component. However, an upper limit of the temperature is preferably 80° C. or lower, more preferably 50° C. or lower, further more preferably 30° C. or lower, particularly preferably 20° C. or lower. Further, a lower limit of the temperature is preferably −20° C. or more. When the temperature exceeds 80° C., the polyamide acid may be decomposed. When the temperature is lower than −20° C., the polymerization reaction is more slowly promoted.

Next, the reaction time in the synthesis reaction of the polyamide acid is not particularly limited as long as it is possible to complete the polymerization reaction of the acid dianhydride component and the diamine component within this time. However, generally, 50 hours is enough as an upper limit of the reaction time, and the upper limit may be 12 hours or less. While, a lower limit of the reaction time is preferably 30 minutes or more, and more preferably 3 hours or more.

Next, the organic solvent used in the synthesis reaction of the polyamide acid is not particularly limited as long as the solvent can sufficiently dissolve the polyamide acid, but it is general to use an organic polar solvent. Further, it is preferable to select an organic polar solvent which can favorably dissolve the polyamide acid and whose boiling point is as low as possible, in order to make it easier to stir the solvent while suppressing increase of viscosity in synthesizing the polyamide acid, to make it easier to dry the obtained soluble polyimide resin (E-1), and to realize a similar object. Thus, it is possible to make the production steps of the soluble polyimide resin (E-1) more efficient.

Specific examples of the organic polar solvent used in the synthesis of the polyamide acid include: sulfoxide solvent such as N,N-dimethyl sulfoxide and N,N-diethyl sulfoxide; formamide solvent such as N,N-dimethyl formamide and N,N-diethyl formamide; acetamide solvent such as N,N-dimethyl acetamide and N,N-diethyl acetamide; pyrrolidone solvent such as N-methyl-2-pyrrolidone and N-vinyl-2-pyrrolidone; phenol solvent such as phenol, o-cresol, m-cresol, p-cresol, xylenol, phenol halide, and catechol; ether solvent such as tetrahydrofuran and dioxane; alcohol solvent such as methanol, ethanol, and butanol; cellosolve such as butyl cellosolve; hexamethylphosphoamide; γ-butyrolactone; and the like, but the organic polar solvent is not particularly limited.

These organic polar solvents may be independently used, or a combination of two or more kinds may be used as a mixture. Further, a combination of the organic polar solvent and an aromatic carbon hydride such as xylene or toluene may be used as required.

A specific condition of the polyamide acid solution obtained in the foregoing synthesis method is not particularly limited, it is preferable that logarithmic viscosity is within the following range. That is, in case where 100 ml of a solution is prepared by using the polyamide acid so that its concentration is 0.5 g/N-methyl-2-pyrrolidone, the logarithmic viscosity at 30° C. preferably ranges from 0.2 to 4.0 (deciliter/gram), more preferably from 0.3 to 2.0 (deciliter/gram).

The polyamide acid used in the present invention is obtained by reacting the acid dianhydride component and the diamine component with each other in the organic solvent as described above. This reaction can be carried out as follows: the diamine component is dissolved or dispersed in the organic solvent in a slurry manner in an inert atmosphere such as argon or nitrogen, and then the acid dianhydride is added. The acid dianhydride is dissolved in the organic solvent or is diffused in a slurry manner or the acid dianhydride is in a solid state. In this case, the reaction temperature preferably ranges from −20° C. to 90° C., and the reaction time preferably ranges from 30 minutes to 24 hours.

Further, an average molecular weight of the polyamide acid used in the present invention preferably ranges from 5000 to 1000000. When the average molecular weight is less than 5000, also a molecular weight of the obtained polyimide composition drops. Thus, even when the polyimide composition is used as a resin, the resin is likely to be brittle. While, the average molecular weight exceeds 1000000, viscosity of the polyamide acid varnish is too high, so that it is likely to be difficult to treat the polyimide acid varnish. Further, it is also possible to mix various kinds of organic additives, inorganic fillers, or various kinds of reinforcing agents with the polyimide composition.

<Imidization of Polyamide Acid in the First Method>

The soluble polyimide resin (E-1) used in the present invention is obtained by imidizing the polyamide acid produced in the foregoing synthesis method. A specific means for carrying out the imidization is not particularly limited. However, the polyamide acid in the polyamide acid solution is subjected to dehydration ring closure for example through a thermal process or a chemical process. The thermal process is a process in which the polyamide acid solution is dehydrated through thermal treatment. The chemical process is a process in which the dehydration is carried out with a dehydrating agent. In addition to these techniques, there is a process in which the imidization is carried out through heat treatment under reduced pressure.

(1) Thermal Process

The thermal process is not particularly limited as long as ring closure based on dehydration is carried out by heating the polyamide acid. Specifically, it is also possible to carry out the ring closure based on dehydration with respect to the polyamide acid for example by performing such an operation that: the polyamide acid solution is heated so as to promote imidization reaction and the solvent is evaporated at the same time; or a similar operation. Conditions of the heat treatment are not particularly limited, but it is preferable that the heating temperature is 300° C. or lower and the heating time ranges from 5 minutes to 10 hours. An example of the thermal process is an azeotropy process using an azeotropic agent. Further, it is possible to adopt a thermal cyclization process or the like using toluene, xylene, or the like.

In the azeotropy process using the azeotropic agent, the imidization is carried out as follows: water such as toluene, xylene, or the like and azeotropic solvent are added to the polyamide acid solution, and temperature of the resultant is raised at 170° C. to 200° C., and reaction thereof is carried out for 1 to 5 hours while positively excluding water, generated by dehydration ring closure of the polyamide acid, to the outside of the system. After completion of the reaction, a product is deposited in an alcohol solvent such as methanol, and the product is rinsed with an alcohol solvent as required, and then the rinsed product is dried, thereby obtaining a soluble polyimide resin (G-1).

Further, another method for carrying out the imidization based on the thermal process is as follows: the polyamide acid solution is made to flow in a spreading manner on or is applied to a film-shape support such as a glass plate, a metal plate, a PET (polyethylene terephthalate), and the like, and then the film-shape support is heated at a temperature ranging from 80° C. to 300° C., thereby obtaining the soluble polyimide resin (G-1).

Note that, the heating time varies depending on an amount of the polyamide acid solution to be subjected to the dehydration ring closure and temperature at which the polyamide acid solution is heated. Generally, it is preferable to heat the polyamide acid solution for a period of time ranging from one minute to five hours after the process temperature has reached the maximum temperature. By carrying out the thermal process, it is possible to obtain the soluble polyimide resin (E-1).

(2) Chemical Process

An example of the chemical process is a process in which a dehydrating agent whose amount is not less than a stoichiometric amount and a catalyst are added to the polyamide acid solution, thereby carrying out dehydration reaction and evaporation of the organic solvent. After completion of the reaction, a product is deposited in an alcohol solvent such as methanol, and the deposited product is rinsed with an alcohol solvent as required, and then the rinsed product is dried. By carrying out the chemical process, it is possible to obtain the soluble polyimide resin (E-1).

Specific examples of the dehydrating agent include: fatty acid anhydride such as acetic anhydride and propionic acid anhydride; aromatic acid anhydride such as anhydrous benzoic acid; carbodiimides such as N,N'-dichlohexylcarbodiimide and N,N'-diisopropylcarbodiimide; and the like. Further, specific examples of the catalyst include: aliphatic tertiary amines such as triethylamine and trimethylamine; aromatic tertiary amines such as dimethylaniline; heterocyclic tertiary amines such as pyridine, α-picoline, β-picoline, γ-picoline, isoquinoline, and imidazole.

Conditions of the chemical process are not particularly limited, but the reaction temperature is preferably 100° C. or lower, and the reaction time preferably ranges from approximately one to 50 hours. Further, conditions of the evaporation of the organic solvent are not particularly limited, the heating temperature is preferably 200° C. or lower, and the heating time preferably ranges from approximately 5 minutes to 12 hours.

Note that, in case where the soluble polyimide resin (G-1) obtained in the foregoing manner has a hydroxyl group, the acid dianhydride added as the dehydrating agent may react with the hydroxyl group, so that it is preferable that an amount of the acid anhydride is minimum stoichiometrically required in the imidization.

(3) Heat Treatment Under Reduced Pressure

An example of a process other than the thermal process and the chemical process is imidization based on heat treatment under reduced pressure (for ease of description, this treatment is referred to as reduced-pressure heating process). By carrying out the reduced-pressure heating process, it is possible to obtain the soluble polyimide resin (E-1). Conditions of the reduced-pressure heating process are not particularly limited as long as it is possible to carry out the imidization under the conditions. However, among the conditions, it is preferable to define a heating condition and a pressure condition as follows.

First, as to the heating condition, the temperature ranges from 80° C. to 400° C. However, in order to efficiently carry out the imidization and dehydration, a lower limit thereof is preferably 100° C. or higher, more preferably 120° C. or higher. While, it is preferable that a maximum temperature (upper limit) in the heat treatment is a thermal decomposition temperature or lower of the obtained soluble polyimide resin (E-1). Thus, the upper limit in the heating generally ranges from approximately 250° C. to 350° C. (temperature at which the imidization is completed), preferably from approximately 180° C. to 350° C.

Next, the pressure condition is not particularly limited as long as the pressure is low. Specifically, the pressure preferably ranges from 0.001 to 0.9 atomometer, more preferably from 0.001 to 0.8 atomometer, still more preferably from 0.001 to 0.7 atomometer. In other words, an upper limit of the pressure in the reduced-pressure heating process is less than 1 atomometer, preferably 0.9 atomometer or less, more preferably 0.8 atomometer or less, still more preferably 0.7 atomometer or less. While, a lower limit of the pressure is not particularly limited as long as the lower limit is 0.001 atomometer or more.

In the method for imidizing the polyamide acid in accordance with the reduced-pressure heating process, it is possible to positively exclude water generated by the imidization to the outside of the system. Thus, it is possible to suppress hydrolysis of the polyamide acid. Further, the acid dianhydride serving as a material for the polyamide acid contains a one-side ring-opened substance or a double-side ring-opened substance as an impurity, but it is possible to carry out ring closure with respect to the one-side ring-opened substance or the double-side ring-opened substance by adopting the reduced-pressure heating process. As a result, it is possible to raise a molecular weight of the obtained soluble polyimide resin (E-1).

Here, the following describes a specific method for directly imidizing the polyamide acid solution by heating/drying the polyamide acid solution under reduced pressure.

As described above, any method may be adopted as the method for imidizing the polyamide acid solution as long as it is possible to heat/dry the polyamide acid solution under reduced pressure. However, examples of the method are: a method in which the polyamide acid solution is heated/dried by using a vacuum oven as a batch-type process; and a method in which the polyamide acid solution is heated/dried by using a double-axis or triple-axis extruder having a decompressor as a sequential-type process. By adopting either of the methods, it is possible to carry out the imidization. Each of these methods may be selected in consideration for an amount of production and the like.

The double-axis or triple-axis extruder having a decompressor is obtained by providing a general melting extruder, heating/melting a thermoplastic resin, with a device for removing the solvent through decompression. When the double-axis or triple-axis extruder is used, the polyamide acid is kneaded by the extruder, and the solvent and water generated at the time of imidization are removed, thereby obtaining the soluble polyimide resin (E-1).

In this manner, it is possible to obtain the soluble polyimide resin (E-1) of the present invention whose carboxylic acid equivalent ranges from 300 to 3000 or the soluble polyimide resin (E-1) of the present invention whose hydroxyl group equivalent ranges from 250 to 3000. Further, a carboxyl group or a hydroxyl group is included, so that it is possible to provide the soluble polyimide resin which is soluble in an alkaline aqueous solution.

Further, the polyamide acid solution is poured directly into a vessel having been subjected to a mold releasing treatment such as coating or the like with a fluorine resin, and the polyamide acid solution is heated/dried under reduced pressure, so that it is also possible to carry out dehydration ring closure with respect to the polyamide acid solution.

(4) Solidification Process which Causes the Solvent not to Evaporate

In the thermal process and the chemical process or the reduced-pressure heating process, the solvent is evaporated during a process for carrying out the imidization. However, in the thermal process and the chemical process, there is a method for obtaining the solid soluble polyimide resin (E-1) without evaporating the solvent for example. Specifically, in this method, a solution of the soluble polyimide resin (E-1) obtained in the thermal process or the chemical process is added to a poor solvent, and the polyimide resin is deposited, and the deposited polyimide resin is dried, thereby obtaining the solid soluble polyimide resin (E-1).

A solvent used as the poor solvent used in this method is not particularly limited as long as the poor solvent is favorably mixed with the solution of the obtained soluble polyimide resin (E-1) but less dissolves the soluble polyimide resin (E-1). Specific examples of the poor solvent include acetone, methanol, ethanol, isopropanol, benzene, methylcellosolve (registered trademark), methyl ethyl ketone, water, and the like.

According to the method, the soluble polyimide resin (E-1) is deposited in the poor solvent, so that it is possible not only to obtain the solid soluble polyimide resin (E-1) but also to purify the soluble polyimide resin (E-1) by removing impurities. Examples of the impurities are unreacted monomer components (acid dianhydride and diamine), acetic anhydride and pyridine (in case of the chemical process), toluene and xylene (in case of the thermal process). In the method for carrying out the deposition with the poor solvent, it is possible to purify and dry the soluble polyimide resin (E-1) by removing the impurities. Thus, it is possible to improve the quality of the obtained soluble polyimide resin (E-1).

<Second Method>

The second method for synthesizing (producing) the soluble polyimide resin (E-1) is a method in which the acid dianhydride containing at least one kind of acid dianhydride is reacted with the isocyanate component containing at least one kind of diisocyanate in the organic solvent. At this time, as in the synthesis of the polyamide acid of the first method, the acid dianhydride component and the isocyanate component are blended with each other so that they are substantially identical with each other in a molar ratio.

In the second method, the method for reacting the monomer components with each other is not particularly limited. However, it is general to adopt a method in which: as in the synthesis of the polyamide acid, the acid dianhydride component and the isocyanate component which are substantially identical with each other in a molar ratio are dissolved in the organic solvent, and then the resultant is stirred while controlling reaction conditions until the polymerization is completed. The method allows preparation of a solution (soluble polyimide solution) by dissolving the polyimide acid in the organic solvent with a single step.

It is possible to react the monomer components without any solvent. However, it is preferable to use a catalyst in reaction between the isocyanate component and an active hydrogen compound. Examples of the catalyst include: tertiary amines; an alkaline metal compound; an alkaline earth metal compound; or metals such as cobalt, titanium, tin, zinc; and a semimetal compound; and the like. Note that, in the second method, an order in which the acid dianhydride component and the isocyanate component are added is not particularly limited as long as the addition is carried out in the same manner as in the synthesis method of the polyamide acid.

In the second method, a synthesis condition of the soluble polyimide resin (E-1) is not particularly limited as long as it is possible to sufficiently synthesize polyimide by polymerizing the monomer components. In the present invention, among synthesis conditions, it is preferable to define a temperature condition and the organic solvent to use as follows.

First, in the second method, the temperature condition under which synthesis reaction of the polyamide acid is carried out is not particularly limited as long as the temperature range allows polymerization of the acid dianhydride component and the isocyanate component. However, generally, the reaction temperature preferably ranges from 50° C. to 220° C. Note that, the reaction time is not particularly limited.

Next, the organic solvent used in the synthesis reaction of the second method is not particularly limited as long as the solvent can sufficiently dissolve the obtained soluble polyimide resin (E-1). However, as in the case of synthesizing the polyamide acid, it is preferable to select an organic solvent which can favorably dissolve the polyimide and whose boiling point is as low as possible, in order to make it easier to stir the solvent while suppressing increase of viscosity in synthesizing the polyimide, to make it easier to dry the obtained soluble polyimide resin (E-1), and to realize a similar object. Thus, it is possible to make the production steps of the soluble polyimide resin (E-1) more efficient.

Specific examples of the organic solvent which can be used in the synthesis reaction of the second method include: amides organic solvent such as N,N-dimethyl formamide, N,N-dimethyl acetamide, N,N-diethyl acetamide, N,N-dimethylmethoxy acetamide, N-methyl-2-pyrrolidone, and hexamethyl phosphamido; lactams organic solvent such as N-methyl caprolactam; urea organic solvent such as 1,3-dimethyl-2-imidazolidinon and tetramethyl area; hydrocarbons organic solvent such as 1,2-dimethoxyethane, 1,2-bis(2-methoxyethyl)ethane, and bis[2-(2-methoxyethoxy)ethane]; ethers organic solvent such as bis(2-methoxyethyl)ether, bis [2-(2-methoxy)ethyl]ether, 1,3-dioxane, 1,4-dioxane, tetrahydrofuran, and digrime; esters organic solvent such as γ-butyrolactone; pyridines organic solvent such as pyridine and picoline; sulfurs organic solvent such as dimethyl sulfoxide, dimethyl sulfone, and sulforan; nitro organic solvent such as nitromethane, nitroethane, and nitrobenzene; nitryls organic solvent such as acetonitrile; and the like. However, the organic solvent is not limited to them. The organic solvents may be independently used, or a suitable combination of two or more kinds may be used.

<Soluble Polyimide Solution>

In preparing the photosensitive resin composition of the present invention, the obtained soluble polyimide resin (E-1) is dissolved in the desired organic solvent, thereby using the resultant as the soluble polyimide solution. The organic solvent used in the soluble polyimide solution is not particularly limited as long as the organic solvent can dissolve the obtained soluble polyimide resin (E-1). However, an example thereof is an organic polar solvent used in the synthesis reaction of the polyamide acid. These organic solvents may be independently used, or a suitable combination of two or more kinds may be used.

A concentration of the soluble polyimide solution is not particularly limited, and the concentration may be suitably determined depending on use (purpose of use) of the obtained photosensitive resin composition and how the photosensitive resin composition is used. However, the concentration generally ranges from 1 to 30 wt %. Further, the viscosity of the soluble polyimide solution is not particularly limited. However, generally, in case where N-methyl-2-pyrrolidone solution is used as the soluble polyimide solution, it is preferable that the logarithmic viscosity at 30° C. ranges from 0.1 to 2.5 (deciliter/gram). When the logarithmic viscosity is within this range, this allows a molecular weight of the soluble polyimide resin (E-1) have a generally favorable value.

Note that, in the photosensitive resin composition according to the present invention, at least one kind of the soluble polyimide resin (E-1) is included, two or more kinds of soluble polyimide resins (E-1) may be included, or a polyimide resin other than these resins may be included. Further, a polyamide acid serving as a precursor that has not been imidized may be used as the soluble polyimide resin (E-1). In preparing the heat resistance resin composition and the photosensitive resin composition, it is preferable to use not the polyamide acid but the imidized soluble polyimide resin (E-1) since the imidized soluble polyimide resin (E-1) hardly causes reaction in blending the components and its stability is high.

In the photosensitive resin composition according to the present invention, an amount of the soluble polyimide resin (E-1) blended is not particularly limited. However, when a total amount of the photosensitive resin composition is 100 wt (mass) %, its lower limit is preferably 20 wt % or more, more preferably 30 wt % or more. While, its upper limit is preferably 80 mass% or less, more preferably 60 mass% or less. When the amount of the soluble polyimide resin (E-1) blended is within this range, it is possible to enhance the easiness to process the photosensitive resin composition and it is possible to improve properties (dielectric property, heat resistance, and the like) of a cured resin (cured product) obtained by curing the photosensitive resin composition.

<Epoxy Denaturalized Polyimide Resin>

As described above, it is preferable that the soluble polyimide resin (E-1) used in the present invention has a hydroxyl group or a carboxyl group. An epoxy compound having an epoxy group (for ease of description, the epoxy compound added to the soluble polyimide resin is referred to as a PI epoxy compound) is added to the soluble polyimide resin having a carboxyl group, so that the carboxyl group of the soluble polyimide resin and the epoxy group of the epoxy compound are reacted with each other. As a result, an ester bond and a secondary hydroxyl group are generated as CO—O—CH$_2$—CH(OH)—. The compound having the ester bond and the secondary hydroxyl group less takes in metal ions at the time of development, so that its electric property does not drop. This fact was found by the inventors of the present invention. In addition, it was found that development can be carried out with an alkaline aqueous solution. Thus, it is preferable that: in the soluble polyimide resin (E-1) of the present invention, the carboxyl group and the epoxy group of the soluble polyimide resin are reacted with each other so as to produce a soluble polyimide resin having been epoxy-denaturalized (hereinafter, referred to as epoxy denaturalized polyimide resin).

That is, it is preferable to produce the epoxy denaturalized polyimide resin by denaturalizing the soluble polyimide resin (E-1) whose carboxylic acid equivalent ranges from 300 to 3000 with a PI epoxy compound having an epoxy group. The carboxylic acid equivalent of the soluble polyimide resin (E-1) constituting the epoxy denaturalized polyimide resin preferably ranges from 350 to 2500, more preferably from 350 to 2000. It is not preferable that the carboxylic acid equivalent exceeds 3000 since the epoxy denaturalized polyimide resin is less dissolved in an aqueous alkaline developer and developing time is longer. Further, when diamine having two or more carboxyl groups is used, it is possible to realize the carboxylic acid equivalent of 300 or less, but it is necessary to use a monomer having a large molecular weight to some extent so as to raise the solubility, so that it is difficult to set the carboxylic acid equivalent to 300 or less.

In order to realize the aforementioned carboxylic acid equivalent, it is preferable to use diamine having two or more carboxyl groups in its molecule. It is preferable to use the diamine since it is possible to copolymerize diamines different from each other in realizing a predetermined carboxylic acid equivalent, so that it becomes easier to design properties.

Note that, a hydroxyl group equivalent of the epoxy denaturalized polyimide resin preferably ranges from 250 to 3000, more preferably from 300 to 2000, most preferably from 300 to 1500. It is not preferable that the hydroxyl group equivalent exceeds 3000 since the epoxy denaturalized polyimide resin is less dissolved in the alkaline aqueous solution and it is difficult to carry out the development. Further, it is not preferable that the hydroxyl group equivalent is less than 250 since the heat resistance drops and its large amount of water absorptive hydroxyl groups causes the resultant to absorb more moisture.

Next, a production method of the epoxy denaturalized polyimide resin is described as follows. The soluble polyimide resin (E-1) having a carboxyl group is dissolved in an organic solvent, and the PI epoxy compound and the carboxyl group of the soluble polyimide resin (E-1) are reacted with each other, thereby obtaining the epoxy denaturalized polyimide resin.

The organic solvent used in the reaction is not particularly limited as long as the organic solvent does not react with the epoxy group and can dissolve the soluble polyimide resin (E-1) having a carboxyl group. Specific examples of the organic solvent include: sulfoxide solvent such as dimethyl sulfoxide and diethyl sulfoxide; formamide solvent such as N,N-dimethyl formamide and N,N-diethyl formamide; acetamide solvent such as N,N-dimethyl acetamide and N,N-diethyl acetamide; pyrrolidone solvent such as N-methyl-2-pyrrolidone and N-vinyl-2-pyrrolidone; ether solvent such as tetrahydrofuran and dioxane; alcohol solvent such as methanol, ethanol, and butanol; cellosolve such as butyl cellosolve; hexamethyl phosphoamide; γ-butyrolactone; and the like. Additional examples thereof are aromatic hydrocarbons such as xylene and toluene. These organic solvents may be independently used, or a suitable combination of two or more kinds may be used. It is general that the epoxy denaturalized polyimide resin used in the present invention is finally used after removing the solvent therefrom, so that it is important to select a solvent whose boiling point is as low as possible.

<PI Epoxy Compound>

Here, the PI epoxy compound reacted with the soluble polyimide resin (E-1) having a carboxyl group is described as follows. Preferable examples of the PI epoxy compound include an epoxy compound having two or more epoxy groups and an epoxy compound having an epoxy group and an unsaturated double bond or an unsaturated triple bond.

The epoxy compound having two or more epoxy groups is a compound which has two or more epoxy groups in its molecule. Specific examples thereof include: bisphenol resins such as Epikote 828 (commercial name: product of Shell Chemicals Japan Ltd.); o-cresolnovolak-type epoxy resins such as 180S65 (commercial name: product of Shell Chemicals Japan Ltd.); bisphenol A novolak resins such as 157S70 (commercial name: product of Shell Chemicals Japan Ltd.); trishydroxyphenylmethanenovolak resins such as 1032H60 (commercial name: product of Shell Chemicals Japan Ltd.); naphthalenearalkylnovolak resins such as ESN375 (commercial name: product of Nippon Steel Chemical Group); tetraphenylolethane 1031 S (commercial name: product of Shell Chemicals Japan Ltd.); glycidyl amine type resins such as YGD414S (commercial name: product of Tohto Kasei CO., Ltd.), trishydroxyphenylmethane EPPN502H (commercial name: Nippon Kasei Chemical Co., Ltd.), special bisphenol VG3101L (commercial name: product of Mitsui Chemicals. Inc.), special naphthol NC7000 (commercial name: product of Nippon Kayaku Co., Ltd.), TETRAD-X and TETRAD-C (both of which are commercial names: products of MITSUBISHI GAS CHEMICAL COMPANY. INC.; and the like. However, the epoxy compound having two or more epoxy groups is not limited to them. These PI epoxy compounds may be independently used, or a suitable combination of two or more kinds may be used.

Further, the epoxy compound having an epoxy group and an unsaturated double bond is a compound which has an epoxy compound and an unsaturated double bond in its molecule. Specific examples thereof includes allyl glycidyl ether, glycidyl acrylate, glycidyl methacrylate, glycidyl vinyl ether, and at least one kind of a epoxy compound selected from compounds each of which has a structure represented by the following formula (15). However, the PI epoxy compound is not limited to them.

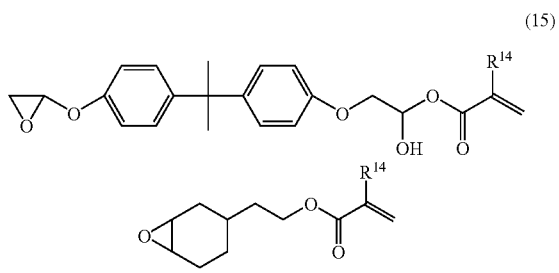

(15)

where $R^{14}$ represents a hydrogen or methyl group. These PI epoxy compounds may be independently used, or a suitable combination of two or more kinds may be used.

Further, the epoxy compound having an epoxy group and an unsaturated triple bond is a compound which has an epoxy group and an unsaturated triple bond in its molecule. Specific examples thereof include propargyl glycidyl ether, glycidyl propioate, ethynyl glycidyl ether, and the like, but the PI epoxy compound is not limited to them. These PI epoxy compounds may be independently used, or a suitable combination of two or more kinds may be used.

In order to react the PI epoxy compound with the soluble polyimide resin (E-1) having a carboxyl group, they are dissolved in the organic solvent, and the mixture is heated. It is possible to adopt any method for dissolving these components in the organic solvent, and the reaction temperature is preferably 40° C. or higher and 130° C. or lower. Particularly, in case of using the PI epoxy compound having an unsaturated double bond or an unsaturated triple bond, it is preferable to carry out the reaction at such temperature that the unsaturated double bond or the unsaturated triple bond is decomposed or cross-linked by heat. Specifically, it is preferable to carry out the reaction at 40° C. or higher and 100° C. or lower, and it is more preferable to carry out the reaction at 50° C. or higher and 90° C. or lower. Further, the reaction time preferably ranges from several minutes to about 8 hours. In this manner, it is possible to obtain a solution of the epoxy denaturalized polyimide resin.

Note that, a thermoplastic resin such as polyester, polyamide, polyurethane, polycarbonate, and the like may be mixed with the epoxy denaturalized polyimide resin solution, or a thermosetting resin such as epoxy resin, acryl resin, bismaleimide, bisallylnadiimide, a phenolic resin, a cyanate resin, and the like may be mixed with the epoxy denaturalized polyimide resin solution. Further, various kinds of coupling agents may be mixed.

When a curing agent generally used for an epoxy resin is blended with the epoxy denaturalized polyimide resin used in the present invention, it may be possible to obtain a cured product having favorable properties. This condition is confirmed particularly in an epoxy denaturalized polyimide resin obtained by reacting the PI epoxy compound having two or more epoxy groups with the soluble polyimide resin (E-1) having a carboxyl group. Typical examples of the epoxy resin curing agent used in this case include amine curing agents, imidazole curing agents, acid dianhydride curing agents, acid curing agents, and the like, but the curing agent is not particularly limited.

[Other Component (F)]

The photosensitive resin composition according to the present invention may include not only the double bond phosphazene compound and the soluble polyimide resin (E-1) but also other component (F). The "other component (F)" is suitably selected depending on usage thereof, and is not particularly limited. However, specific examples thereof include a photoreaction initiator (F-1), a sensitizer (F-2), a photopolymerization assistant (F-3), a compound having a carbon-carbon double bond (F-4), a composition epoxy resin (F-5), an inorganic filler, and the like.

<Photoreaction Initiator (F-1)>

It is more preferable that the photosensitive resin composition according to the present invention contains the photoreaction initiator (F-1) in order to have the photosensitivity. An example of the compound used as the photoreaction initiator (F-1) is an acylphosphine oxide compound which generates a radical by light whose wavelength is long as a g line and is represented by the following formula. (16) or an acylphosphine oxide compound represented by the following formula (17).

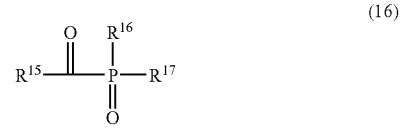

(16)

where each of $R^{15}$, $R^{16}$, and $R^{17}$ represents $C_6H_5$—, $C_6H_4(CH_3)$—, $C_6H_2(CH_3)_3$—, $(CH_3)_3C$—, $C_6H_3Cl_2$—, $C_6H_3(CH_3)_2$—, $C_5H_4Cl$—, or $C_6H_2Cl_3$—.

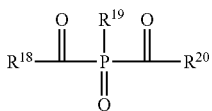
(17)

where each of $R^{18}$, $R^{19}$, and $R^{20}$ represents $C_6H_5$—, a methoxy group, an ethoxy group, $C_6H_4(CH_3)$—, $C_6H_2(CH_3)_3$—, $C_6H_3(CH_3)_2$—, $C_6H_4Cl$—, or $C_6H_2Cl_3$—. A radical generated from each of the compounds reacts with a reaction group (a vinyl group, an acryloyl group, a methacryloyl group, an acryl group, and the like) having an unsaturated double bond, and promotes cross-linking.

It is preferable to use the acylphosphineoxide compound represented by the formula (16) as the photoreaction initiator (F-1) since this generates two radicals. It is more preferable to use the acylphosphine oxide compound represented by the formula (17) since this generates four radicals through a cleavage.

As a radical initiator, various kinds of peroxides can be combined with the following sensitizer (F-2). Among them, it is particularly preferable to combine 3,3',4,4'-tetra (t-butylperoxycarbonyl)benzophenon with the sensitizer (F-2).

<Sensitizer (F-2)>

In order to achieve practical photosensitivity, the photosensitive resin composition according to the present invention may include the sensitizer (F-2). Preferable specific examples of the sensitizer (F-2) include Michler's ketone, bis-4,4'-diethylaminobenzophenon, benzophenon, camphor quinone, benzyl, 4,4'-dimethylaminobenzyl, 3,5-bis(diethylamino benzylidene)-N-methyl-4-pipelidone, 3,5-bis(dimethylamino benzylidene)-N-methyl-4-pipelidone, 3,5-bis(diethylamino benzylidene)-N-ethyl-4-pipelidone, 3,3'-carbonylbis (7-diethylamino)coumarin, riboflavintetrabutylate, 2-methyl-1-[4-(methylthio)phenyl]-2-morpholinopropane-1-one, 2,4-dimethylthioxanthene, 2,4-diethylthioxanthene, 2,4-diisopropylthioxanthene, 3,5-dimethylthioxanthene, 3,5-diisopropylthioxanthene, 1-phenyl-2-(ethoxycarbonyl)oxy-iminopropane-1-one, benzoin ether, benzoinisopropylether, benzanthrone, 5-nitroacenaphthene, 2-nitrofluorene, anthrone, 1,2-benzanthraquinone, 1-phenyl-5-mercapto-1H-tetrazole, thioxanthene-9-one, 10-thioxanthenone, 3-acetylindole, 2,6-di(p-dimethylaminobenzal)-4-carboxycyclohexanone, 2,6-di(p-dimethylaminobenzal)-4-hydroxycyclohexanone, 2,6-di(p-diethylaminobenzal)-4-carboxycyclohexanone, 2,6-di(p-diethylaminobenzal)-4-hydroxycyclohexanone, 4,6-dimethyl-7-ethylaminocoumarin, 7-diethylamino-4-methylcoumarin, 7-diethylamino-3-(1-methylbenzoimidazolyl)coumarin, 3-(2-benzoimidazolyl)-7-diethylaminocoumarin, 3-(2-benzothiazolyl)-7-diethylaminocoumarin, 2-(p-dimethylaminostyryl)benzoxazole, 2-(p-dimethylaminostilyl)quinoline, 4-(p-dimethylaminostilyl)quinoline, 2-(p-dimethylaminostilyl)benzothiazole, 2-(p-dimethylaminostilyl)-3,3-dimethyl-3H-indole, and the like, but the sensitizer is not limited to them.

With respect to 100 parts by weight of the phosphazene compound of the present invention, an amount of the sensitizer (F-2) blended preferably ranges from 0.1 to 50 parts by weight, more preferably from 0.3 to 20 parts by weight. It is not preferable that the amount deviates from the foregoing range (0.1 to 50 parts by weight) because it is impossible to obtain the sensitization effect and this may have a bad influence on the developing property. Note that, as the sensitizer (F-2), one kind of a compound may be used, or a mixture of plural kinds may be used.

<Photopolymerization assistant (F-3)>

In order to achieve practical photosensitivity, the photosensitive resin composition according to the present invention may include a photopolymerization assistant (F-3). Specific examples of the photopolymerization assistant (F-3) include 4-diethylaminoethylbenzoate, 4-dimethylaminoethylbenzoate, 4-diethylaminopropylbenzoate, 4-dimethylaminopropylbenzoate, 4-dimethylaminoisoamylebenzoate, N-phenylglycine, N-methyl-N-phenylglycine, N-(4-cyanophenyl) glycine, 4-dimethylaminobenzonitrile, ethyleneglycoldithioglycolate, ethyleneglycol di(3-mercaptopropionate), trimethylolpropanethioglycolate, trimethylolpropane tri(3-mercaptopropionate), pentaerythritoltetrathioglycolate, pentaerythritol tetra(3-mercaptopropionate), trimethylolethanetrithioglycolate, trimethylolpropanetrithioglycolate, trimethylolethane tri(3-mercaptopropionate), dipentaerythritolhexa(3-mercaptopropionate), thioglycolic acid, α-mercaptopropionic acid, t-butylperoxybenzoate, t-butylperoxymethoxybenzoate, t-butylperoxynitrobenzoate, t-butylperoxyethylbenzoate, phenylisopropylperoxybenzoate, di t-butyldiperoxyisophthalate, tri t-butyltriperoxytrimellitate, tri t-butyltriperoxytrimesitate, tetra t-butyltetraperoxypyromellitate, 2,5-dimethyl-2,5-di(benzoylperoxy)hexane, 3,3',4,4'-tetra(t-butylperoxycarbonyl)benzophenone, 3,3,4,4'-tetra(t-amylperoxycarbonyl)benzophenone, 3,3',4,4'-tetra(t-hexylperoxycarbonyl)benzophenone, 2,6-di(p-azidobenzal)-4-hydroxycyclohexanone, 2,6-di(p-azidobenzal)-4-carboxycyclohexanone, 2,6-di(p-azidobenzal)-4-methoxycyclohexanone, 2,6-di(p-azidobenzal)-4-hydroxycyclohexanone, 3,5-di(p-azidobenzal)-1-methyl-4-piperidone, 3,5-di(p-azidobenzal)-4-piperidone, 3,5-di(p-azidobenzal)-N-acetyl-4-piperidone, 3,5-di(p-azidobenzal)-N-methoxycarbonyl-4-piperidone, 2,6-di(p-azidobenzal)-4-hydroxycyclohexanone, 2,6-di(m-azidobenzal)-4-carboxycyclohexanone, 2,6-di(m-azidobenzal)-4-methoxycyclohexanone, 2,6-di(m-azidobenzal)-4-hydroxycyclohexanone, 3,5-di(m-azidobenzal)-N-methyl-4-piperidone, 3,5-di(m-azidobenzal)-4-piperidone, 3,5-di(m-azidobenzal)-N-acetyl-4-piperidone, 3,5-di(m-azidobenzal)-N-methoxycarbonyl-4-piperidone, 2,6-di(p-azidecinnamyliden)-4-hydroxycyclohexanone, 2,6-di(p-azidecinnamyliden)-4-carboxycyclohexanone, 2,6-di(p-azidecinnamyliden)-4-cyclohexanone, 3,5-di(p-azidecinnamyliden)-N-methyl-4-piperidone, 4,4'-diazidochalcone, 3,3'-diazidochalcone, 3,4'-diazidochalcone, 4,3'-diazidochalcone, 1,3-diphenyl-1,2,3-propanetrione-2-(o-acetyl)oxime, 1,3-diphenyl-1,2,3-propanetrione-2-(o-n-propylcarbonyl)oxime, 1,3-diphenyl-1,2,3-propanetrione-2-(o-methoxycarbonyl)oxime, 1,3-diphenyl-1,2,3-propanetrione-2-(o-ethoxycarbonyl)oxime, 1,3-diphenyl-1,2,3-propanetrione-2-(o-benzoyl)oxime, 1,3-diphenyl-1,2,3-propanetrione-2-(o-phenyloxycarbonyl) oxime, 1,3-bis(p-methylphenyl)-1,2,3-propanetrione-2-(o-benzoyl)oxime, 1,3-bis(p-methoxyphenyl)-1,2,3-propanetrione-2-(o-ethoxycarbonyl)oxime, 1-(p-methoxyphenyl)-3-(p-nitrophenyl)-1,2,3-propanetrione-2-(o-phenyloxycarbonyl)oxime, and the like, but the photopolymerization assistant is not limited to them. Further, as another assistant, it is possible to use trialkylamines such as triethylamine, tributylamine, triethernolamine, and the like.

With respect to 100 parts by weight of the phosphazene compound of the present invention, an amount of the photopolymerization assistant blended preferably ranges from 0.1 to 50 parts by weight, more preferably from 0.3 to 20 parts by weight. It is not preferable that the amount deviates from the foregoing range (0.1 to 50 parts by weight) because it is impossible to obtain the desired sensitization effect and this may have a bad influence on the developing property. Note that, as the photopolymerization assistant (F-3), one kind of a compound may be used, or a mixture of plural kinds may be used.

<Compound having a Carbon-carbon Double Bond (Copolymerizable Polymer) (F-4)>

Further, in order to achieve practical photosensitivity, the photosensitive resin composition according to the present invention may include not only the sensitizer and the photopolymerization assistant but also a compound having a carbon-carbon double bond (copolymerizable polymer) (F-4) (for ease of description, this compound is referred to as a copolymerizable monomer). The copolymerizable monomer (F-4) has a carbon-carbon double bond (unsaturated double bond) in its molecule, so that this facilitates the photopolymerization.

Specific examples of the copolymerizable monomer (F-4) include bisphenol F EO denaturalized (n=2 to 50) diacrylate, bisphenol A EO denaturalized (n=2 to 50) diacrylate, bisphenol S EO denaturalized (n=2 to 50) diacrylate, 1,6-hexandiol diacrylate, neopentylglycol diacrylate, ethyleneglycol diacrylate, pentaerythritol diacrylate, trimethylolpropane triacrylate, pentaerythritol triacrylate, dipentaerythritol hexa acrylate, tetramethylol propane tetra acrylate, tetraethyleneglycol diacrylate, 1,6-hexanediol dimethacrylate, neopentylglycol dimethacrylate, ethyleneglycol dimethacrylate, pentaerythritol dimethacrylate, trimethylol propane trimethacrylate, pentaerythritol trimethacrylate, dipentaerythritol hexamethacrylate, tetramethylol propane tetramethacrylate, tetraethyleneglycol dimethacrylate, methoxydiethyleneglycol methacrylate, methoxypolyethyleneglycol methacrylate, β-metachroyl oxyethyl hydrogen phthalate, β-metachroyl oxyethyl hydrogen succinate, 3-chloro-2-hydroxypropyl methacrylate, steallyl methacrylate, phenoxyethyl acrylate, phenoxydiethyleneglycol acrylate, phenoxypolyethyleneglycol acrylate, β-acryloyloxtethyl hydrogen succinate, lauryl acrylate, ethyleneglycol dimethacrylate, diethyleneglycol dimethacrylate, triethyleneglycol dimethacrylate, polyethyleneglycol dimethacrylate, 1,3-buthyleneglycol dimethacrylate, 1,6-hexanediol dimethacrylate, neopentylglycol dimethacrylate, polypropyleneglycol dimethacrylate, 2-hydroxy-1,3dimethachroxypropane, 2,2-bis [4-(methachroxyethoxy)phenyl] propane, 2,2-bis [4-(methachroxy diethoxy)phenyl] propane, 2,2-bis [[4-(methachroxy polyethoxy)phenyl] propane, polyethyleneglycol dichrylate, tripropyleneglycol diacrylate, polypropyleneglycol diacrylate, 2,2-bis [4-(acryloxy diethoxy)phenyl] propane, 2,2-bis [4-(acryloxy polyethoxy) phenyl] propane, 2-hydroxy-1-acryloxy3-methachloxy propane, trimethylol propane trimethacrylate, tetramethylol methane triacrylate, tetramethyrol methane tetraacrylate, methoxy dipropyleneglycol methacrylate, methoxytriethyleneglycol acrylate, nonylphenoxypolyethyleneglycol acrylate, nonylphenoxypolypropyleneglycol acrylate, 1-acryloyloxypropyl-2-phthalate, isosteallyl acrylate, polyoxyethylenealkylether acrylate, nonylphenoxyethyleneglycol acrylate, polypropyleneglycol dimethacrylate, 1,4-butanediol dimethacrylate, 3-methyl-1,5-pentanediol dimethacrylate, 1,6-mexanediol dimethacrylate, 1,9-nonanediol methacrylate, 2,4-diethyl-1,5-pentanediol dimethacrylate, 1,4-cyclohexanedimethanol dimethacrylate, dipropyleneglycol diacrylate, tricyclodecanedimethanol diacrylate, 2,2-hydrogenerated bis [4-(acryloxy polyethoxy) phenyl] propane, 2,2'-bis [4-(acryloxy polypropoxy)phenyl] propane, 2,2-bis [4-(acryloxy polyethoxy)phenyl] propane, 2,4-diethyl-1,5-pentanediol diacrylate, ethoxylated tothymethylolpropane triacrylate, propoxylated tothymethylolpropane triacrylate, isocyanuric acid tri(ethaneacrylate), pentathritol tetra acrylate, ethoxylated pentathritol tetra acrylate, propoxylated pentathritol tetra acrylate, ditrimethylolpropane tetra acrylate, dipentaerythritol polyacrylate, isocyanuric acid triallyl, glycidyl methacrylate, glycidyl allylether, 1,3,5-triacryloylhexahydro-s-triazine, triallyl1,3,5-benzenecarboxylate, triallyl amine, triallyl citrate, triallyl phosphate, allobarbital, diallyl amine, diallyl dimethyl silane, diallyl disulfide, diallyl ether, diallyl cyanulate, diallyl isophthalate, diallyl telephtalate, 1,3-diallyloxy-2-propanol, diallyl sulfide diallyl maleate, 4,4'-isopropyliden diphenol dimethacrylate, 4,4'-isopropyliden diphenol diacrylate, and the like, but the copolymerizable monomer (F-4) is not limited to them.In order to improve the cross-linked density, it is particularly preferable to use a bifunctional or further multifunctional monomer. Note that, the EO denaturalization is an ethyleneoxide denaturalized portion.

Further, in order to exhibit the flexibility of a cured resin (for example, a photosensitive dry film resist) obtained by curing the photosensitive resin composition according to the present invention, it is preferable to use, as a copolymerizable monomer, bisphenol F EO denaturalized diacrylate, bisphenol A EO denaturalized diacrylate, bisphenol S EO denaturalized diacrylate, bisphenol F EO denaturalized dimathacrylate, bisphenol A EO denaturalized dimethacrylate, and bisphenol S EO denaturalized dimethacrylate. Particularly, the number of recurring units of denaturalized EO contained in a single molecule of diacrylate or methacrylate preferably ranges from 2 to 50, more preferably from 2 to 40. When the number of recurring units of EO is within the foregoing preferable range, the obtained photosensitive resin composition has higher solubility with respect to the alkaline aqueous solution, so that the developing time is reduced. Note that, it is not preferable that the number of recurring units of EO is 50 or more, because the heat resistance is likely to drop under this condition.

With respect to 100 parts by weight of the phosphazene compound of the present invention, an amount of the copolymerizable monomer (F-1) blended preferably ranges from 1 to 200 parts by weight, more preferably from 3 to 150 parts by weight. It is not preferable that the amount of the copolymerizable monomer blended deviates from the range (1 to 200 parts by weight) because it is impossible to obtain the desired sensitization effect and this may have a bad influence on the developing property. Note that, as the copolymerizable monomer (F-4), one kind of a compound may be used, or a mixture of plural kinds may be used.

<Composition Epoxy Resin (F-5)>

Further, in order to improve the bonding property, the photosensitive resin composition according to the present invention may include an epoxy resin (for ease of description, the epoxy resin included in the photosensitive resin composition is referred to as a composition epoxy resin). The composition epoxy resin (F-5) is not particularly limited as long as the compound has an epoxy group in its molecule. However, specific examples thereof include: bisphenol resins such as Epikote 828 (commercial name: product of Shell Chemicals Japan Ltd.); o-cresolnovolak-type epoxy resins such as 180S65 (commercial name: product of Shell Chemicals Japan Ltd.); bisphenol A novolak resins such as 157S70 (commercial name: product of Shell Chemicals Japan Ltd.); trishydroxyphenylmethanenovolak resins such as 1032H60 (commercial name: product of Shell Chemicals Japan Ltd.);

naphthalenearalkylnovolak resins such as ESN375 (commercial name: product of Nippon Steel Chemical Group); tetraphenylolethane 1031S (commercial name: product of Shell Chemicals Japan Ltd.); glycidyl amine type resins such as YGD414S (commercial name: product of Tohto Kasei CO., Ltd.), trishydroxyphenylmethane EPPN502H (commercial name: Nippon Kasei Chemical Co., Ltd.), special bisphenol VG3101L (commercial name: product of Mitsui Chemicals. Inc.), special naphthol NC7000 (commercial name: product of Nippon Kayaku Co., Ltd.), TETRAD-X and TETRAD-C (both of which are commercial names: products of MITSUBISHI GAS CHEMICAL COMPANY. INC.; and the like.

Further, as the composition epoxy resin (F-5), it is possible to mix an epoxy resin having an epoxy group and an unsaturated double bond or an unsaturated triple bond in its molecule. Examples of the epoxy resin include allyl glycidyl ether, glycidyl acrylate, glycidyl methacrylate, glycidyl vinyl ether, propargyl glycidyl ether, glycidyl propioate, ethynyl glycidyl ether, and the like.

Further, the composition epoxy resin can be used as a thermosetting resin. In this manner, in case where the composition epoxy resin is mixed with the photosensitive resin composition, the composition epoxy resin not only improves the bonding property but also serves as the thermosetting agent. It is preferable to mix the composition epoxy resin with the photosensitive resin composition as the thermosetting resin since it is possible to obtain a thermosetting resin which is made of photosensitive resin composition and has favorable properties. Any curing agent may be used as the thermosetting resin used here as long as the curing agent is made of epoxy resin: any thermosetting resin such as amines, imidazoles, acid dianhydrides, acids, and similar thermosetting resin may be used. Further, various kinds of coupling agents may be mixed therewith.

<Inorganic Filler or the Like (F-6)>

The photosensitive resin composition according to the present invention may further include an inorganic filler such as talc, mica, silica, alumina, barium sulfate, and magnesium oxide, or may further include a color pigment such as cyanine green and cyanine blue. Further, it is possible to use a thixotropy agent, an antifoaming agent, a levelling agent, an ultraviolet ray absorbing agent, an oxidation inhibitor, and a polymerization inhibitor.

Further, in the photosensitive resin composition, a thermosetting resin other than the composition epoxy resin may be mixed. Also in this case, it is possible to obtain a photosensitive resin composition having favorable properties, so that it is preferable to mix the thermosetting resin other than the composition epoxy resin. Examples of the thermosetting resin used here include bismaleimide, bisallylnadiimide, a phenolic resin, a cyanate resin, and the like.

[Photosensitive Resin Composition having no Soluble Polyimide Resin (D)]

As the photosensitive resin composition according to the present invention, it is possible to use not only the photosensitive resin composition containing at least the phosphazene compound and the soluble polyimide resin (D) but also a photosensitive resin composition containing at least the phosphazene compound and the photoreaction initiator (F-1). In this case, not only the phosphazene compound and the photoreaction initiator (F-1) but also a resin other than the soluble polyimide resin (D) may be contained.

As the resin other than the soluble polyimide resin (D), it is preferable to use a resin having properties equal with or superior to properties of the photosensitive resin composition containing the soluble polyimide resin (D) in terms of flame retardancy and easiness to process the obtained photosensitive resin composition. Examples thereof include a resin having a carboxyl group (for ease of description, this resin is referred to as a carboxyl-group resin) and a resin having a hydroxyl group (for ease of description, this resin is referred to as a hydroxyl-group resin). A weight-average molecular weight of the carboxyl-group resin or the hydroxyl-group resin preferably ranges from 10000 to 300000, more preferably from 10000 to 150000, still more preferably from 20000 to 100000. In case where the weight-average molecular weight is less than 10000, when the photosensitive resin composition is used as a photosensitive resin film, the photosensitive film is likely to be brittle. Adversely, when the weight-average molecular weight exceeds 300000, it is hard to develop the photosensitive resin composition, so that the resolution is likely to drop.

Examples of the carboxyl-group resin and the hydroxyl-group resin are as follows, but the carboxyl-group resin and the hydroxyl-group resin are not limited to these examples. An example of the carboxyl-group resin is acrylic copolymers obtained by copolymerizing acrylic compounds, serving as a main component, with an ethylene unsaturated carboxylic acid. Further, it is possible to use acrylic copolymers obtained by copolymerizing the acrylic compounds with other monomer, which is copolymerizable with (meth)acrylic compounds, as well as the ethylene unsaturated carboxylic acid.

Examples of the (meth)acrylic compounds include methyl (meth)acrylate, ethyl(meth)acrylate, propyl(meth)acrylate, butyl(meth)acrylate, hexyl(meth)acrylate, 2-ethylhexyl (meth)acrylate, cyclohexyl(meth)acrylate, benzyl(meth) acrylate, dimethylaminoethyl(meth)acrylate, hydroxyethyl (meth)acrylate, hydroxypropyl(meth)acrylate, glycidyl (meth)acrylate. These (meth)acrylic compounds may be independently used, or a suitable combination of two or more kinds may be used.

Examples of the ethylene unsaturated carboxylic acid include: monocarboxylic acid such as acrylic acid, methacrylic acid, and crotonic acid; dicarboxylic acid such as maleic acid and fumaric acid; or an anhydride or a half ester etc. thereof. These ethylene unsaturated carboxylic acids may be independently used, or a suitable combination of two or more kinds may be used.

Examples of other monomer include: acrylamide compounds such as (meth)acrylamide, 2,2,3,3-tetrafluoropropyl (meth)acrylamide, and diacetoneacrylamide; compound having a vinyl group, e.g., vinylacetate, alkylvinylether, and (meth)acrylnitryl; styrene; α-methylstyrene; tetrahydrofurfuryl(meth)acrylate; diethylaminoethyl(meth)acrylate; 2,2, 2-trifluoroethyl(meth)acrylate; and the like. These monomers may be independently used, or a suitable combination of two or more kinds may be used.

In case of obtaining acrylic copolymers having a carboxyl group by copolymerizing the (meth)acrylic compounds with the ethylene unsaturated carboxylic acid and other monomer, a weight ratio of the (meth)acrylic compounds, the ethylene unsaturated carboxylic acid, and other monomer is not particularly limited, but an amount of the (meth)acrylic compound component contained preferably ranges from 15 to 85 wt %, more preferably from 30 to 80 wt %. Further, an amount of the ethylene unsaturated carboxylic acid component contained preferably ranges from 15 to 85 wt %, more preferably from 20 to 70 wt %. An amount of other monomer component contained preferably ranges from 0 to 70 wt %.

Examples of the hydroxyl-group resin include a phenolic resin, a resorcinol resin, and the like. Further, as other resin, not only the carboxyl-group resin and the hydroxyl-group resin but also a polyester resin, a polyamide resin, a polyimide resin, a polyurethane resin, an epoxy resin, and the like may be used. It is possible to use also oligomer such as an epoxy acrylate resin and the like.

[Photosensitive Resin Composition Solution]

The photosensitive resin composition according to the present invention may include an appropriate organic solvent. When the photosensitive resin composition is dissolved in the appropriate organic solvent, the photosensitive resin composition can be used in a solution (varnish) state. This is convenient in applying and drying the photosensitive resin composition. As the solvent used in this case, it is preferable to use an aprotic polar solvent in terms of the solubility. Specific preferable examples thereof include N-methyl-2-pyrrolidone, N-acetyl-2-pyrrolidone, N-benzyl-2-pyrrolidone, N,N-dimethylformamide, N,N-dimethylacetamide, dimethylsulfoxide, hexamethylphosphortriamide, N-acetyl-ε-caprolactam, dimethylimidazolidinon, diethylglycoldimethylether, triethyleneglycoldimethylether, γ-butyrolactone, dioxane, dioxolane, tetrahydrofuran, chloroform, and methylene chloride. They may be independently used, or a suitable combination thereof may be used. As the organic solvent, a solvent used in the synthesis reaction of the phosphazene compound and left as it is may be used, or a solvent newly added to the isolated phosphazene compound may be used. Further, a solvent such as toluene, xylene, diethylketone, methoxybenzene, and cyclopentanone may be mixed within a range exerting no bad influence on the solubility in order to enhance the easiness to apply.

Further, a 2,2'-hexafluoropropylidendiphthalate dianhydride, a 2,3,3',4'-biphenyltetracarboxylate dianhydride, or the acid dianhydride represented by the formula (1 1) or (12) is used as a main component of the acid dianhydride component, and aromatic diamine having an amino group in its m-position, diamine having a sulfonic group, or siloxanediamine represented by the formula (12) is used as a part of the diamine component, thereby remarkably improving the solubility of the obtained soluble polyimide resin (D). Thus, it is possible to dissolve the resultant in a solvent whose boiling point is low (120° C. or lower) e.g., an ether solvent such as dioxane, dioxolane, and tetrahydrofuran, and a halogen solvent such as chloroform and methylene chloride. Particularly, in case of applying/drying the photosensitive resin composition, it is advantageous to use the solvent whose boiling point is low (120° C. or lower) so as to prevent thermal polymerization when acryl and/or methacryl are mixed.

As described above, the photosensitive resin composition is dissolved in the organic solvent, so that it is possible to obtain the photosensitive resin composition solution. Further, a thermosetting resin such as an epoxy resin and an acryl resin or a thermoplastic resin such as polyester, polyamide, polyurethane, and polycarbonate may be mixed with the photosensitive resin solution as required.

Instead of dissolution of the photosensitive resin composition in the organic solvent, the photosensitive resin composition according to the present invention can be produced in a solution state. Examples thereof include dimethylsulfoxide, hexamethylphosphoamide, dimethylacetoamide, dimethylformamide, N-methyl-2-pyrrolidone, gammabutyrolactone, diglyme, butoxyethanol, propyleneglycolmethylethylacetate (PGMEA), toluene, xylene, dioxolane, tetrahydrofuran, methylethylketone, isopropylalcohol, and the like, but the photosensitive resin composition in the solution state is not limited to them. In order to realize uneven film thickness of the photosensitive resin composition, adjust the thickness, and improve the bonding property thereof, a mixture of two or more solvents can be used. In case of producing a heat-resistant photoresist composition by using the photosensitive resin composition, a photosensitive resin composition solution is produced so as to have concentration ranging from 0.1 to 70 wt %, and coating thickness thereof is adjusted, thereby producing the heat-resistant photoresist.

[Usage of Photosensitive Resin Composition]

A usage of the photosensitive resin composition according to the present invention is not particularly limited, but a specific example thereof is a photosensitive resin film obtained by using the photosensitive resin composition for example. The photosensitive resin composition can be favorably used as a print wiring board adhesive sheet, a photosensitive cover lay film, a print wiring board insulative circuit protection film, or a print wiring board substrate.

The photosensitive resin film is described as follows with a specific example thereof.

The photosensitive resin composition solution is dried into a thin film, thereby producing the photosensitive resin film. It is possible to form the thin film made of the photosensitive resin composition by adopting any one of a spin coating process, a bar coating process, and a doctor blade process, which are widely carried out in an electronic field.

In forming the thin film made of the photosensitive resin composition, it may be so arranged that: the photosensitive resin composition solution is applied to a support made of metal, PET, or the like, and the photosensitive resin composition is stripped away from the support after being dried, and the stripped photosensitive resin composition is treated as a film; or it may be so arranged that: the photosensitive resin composition is used with it laminated on a film such as PET or the like. A temperature at which the photosensitive resin composition solution is dried preferably ranges from 40° C. to 180° C., more preferably from 40° C. to 150° C. When the drying temperature is excessively low, the drying time is longer. It is not preferable that the drying temperature is excessively high since the heat causes the epoxy group and the unsaturated double bond/unsaturated triple bond to be cross-linked and causes thermal decomposition.

As the photosensitive resin film, it is possible to use an FPC photosensitive cover lay film for example. Generally, in the production steps of the FPC, an adhesive is applied to a long film, and the film is dried, and a copper foil is laminated thereon so that these steps are sequentially carried out. The production steps are excellent in terms of the productivity. However, as described above, it is necessary to form holes or windows on an uncombined cover lay film so as to correspond to junctions of terminals or portions of the circuit, and the hole and the like of the cover lay film are almost manually positioned so as to correspond to junctions of terminals or portions of the FPC, and the work size is small and the photosensitive cover lay film is combined with the FPC by a batch process, so that this is not preferable in terms of workability and positional accuracy. This results in increase of the manufacturing cost.

The photosensitive resin film according to the present invention can be laminated at temperature not more than 150° C., and the photosensitive resin film can be laminated directly on the print substrate without any adhesive. It is more preferable that a lamination temperature is lower. The lamination temperature is preferably 130° C. or lower, more preferably 110° C. or lower. Further, in the photosensitive resin film of the present invention, after combining the FPC with the photosensitive resin film, exposure and development are carried out, so that it is possible to form holes which allow connection with the FPC terminal sections, thereby improving the positional accuracy, the workability, and the like. Thus, the photosensitive resin film of the present invention can be favorably used as an FPC photosensitive cover lay film.

In the production steps of the FPC, the FPC is exposed to high temperature of 200° C. or higher in bonding parts and the like with solder. Thus, it is preferable that the cured photosensitive resin film can resist higher temperature. Further, a thermal decomposition temperature of the photosensitive resin film itself is preferably 300° C. or higher, more preferably 320° C. or higher, still more preferably 340° C. or higher.

Further, an FPC conductive layer is made mainly of copper. In case where the copper is exposed to temperature exceeding 200° C., a crystal structure of the copper gradually changes, and its strength drops. Thus, it is necessary to set the curing temperature to 200° C. or lower.

The step of combining the photosensitive resin film with the FPC is described as follows. In this step, a conductor surface of the FPC whose circuit is made of conductor such as a silver foil in advance is protected by the photosensitive resin film. Specifically, the FPC and the photosensitive resin film are made to overlap each other, and they are combined with each other by heat lamination, heat press, or heat vacuum lamination. It is preferable that temperature for combining them is set so as not to cause the epoxy group or the unsaturated double bond/unsaturated triple bond to be cross-linked or so as not to cause thermal decomposition. Specifically, the temperature for combining is preferably 180° C. or lower, more preferably 150° C. or lower, still more preferably 130° C. or lower.

Next, light is irradiated to the thin film made of the photosensitive resin film via a photo mask having a predetermined pattern, thereby obtaining a desired pattern. The developing step may be carried out by using a general positive photoresist developing device. In carrying out the exposure, it is possible to use an exposing device for irradiating visible light or an ultraviolet ray whose wavelength ranges from 200 to 500 nm, and it is advantageous to use an exposing device, provided with a filter preferably indicative of a monotone wavelength, in terms of the resolution and the workability. Further, the present invention is not limited to a specific device or a specific exposing device.

Time required in exposure can be varied depending on an experimental condition. In the present invention, when an ultraviolet ray exposing device provided with a filter indicative of a wavelength of 365 nm is used, it is possible to vary the exposing time from 5 to 300 seconds. By enhancing the exposure of the exposing device, it is possible to reduce the exposing time. A quantity of exposing energy is determined by an energy gauge, and resolution is confirmed by a profile gauge in terms of a depth and a width.

<Developer>

A developer used in the developing step is described as follows.

As the developer, a basic solution can be used. For example, as the developer, an aqueous solution which is basic or a solution in which one kind of a basic compound is dissolved may be used, or a solution in which two or more kinds of basic compounds are dissolved may be used. Generally, the basic solution is a solution obtained by dissolving a basic compound in water. A concentration of the basic compound in the basic solution preferably ranges from 0.1 to 50 weight/wt %, and more preferably from 0.1 to 30 weight/wt % in terms of influence exerted on the support substrate and the like. Note that, in order to improve the solubility of the soluble polyimide resin (D), the developer may partially include an aqueous organic solvent such as methanol, ethanol, propanol, isopropyl alcohol, N-methyl-2-pyrrolidone, N-methyl-2-pyrrolidone, N,N-dimethyl formamide, and N,N-dimethyl acetamide.

Examples of the basic compound are alkaline metal, alkaline earth metal or ammonium ion hydroxide or carbonate, amine compound, and the like. Specific preferable examples thereof include 2-dimethylaminoethanol, 3-dimethylamino-1-propanol, 4-dimethylamino-1-butanol, 5-dimethylamino-1-pentanol, 6-dimethylamino-1-hexanol, 2-dimethylamino-2-methyl-1-propanol, 3-dimethylamino-2,2-dimethyl-1-propanol, 2-diethylaminoethanol, 3-diethylamino-1-propanol, 2-diisopropylaminoethanol, 2-di-n-butylaminoethanol, N,N-benzyl-2-aminoethanol, 2-(2-dimethylaminoethoxy)ethanol, 2-(2-diethylaminoethoxy)ethanol, 1-dimethylamino-2-propanol, 1-diethylamino-2-propanol, N-methyldiethanolamine, N-ethyldiethanolamine, N-n-butyldiethanolamine, N-t-butyldiethanolamine, N-lauryldiethanolamine, 3-diethylamino-1,2-propanediol, triethanolamine, triisopropanolamine, N-methylethanolamine, N-ethylethanolamine, N-n-butylethanolamine, N-t-butylethanolamine, diethanolamine, diisopropanolamine, 2-aminoethanol, 3-amino-1-propanol, 4-amino-1-butanol, 6-amino-1-hexanol, 1-amino-2-propanol, 2-amino-2,2-dimethyl-1-propanol, 1-aminobutanol, 2-amino-1-butanol, N-(2-aminoethyl)ethanolamine, 2-amino-2-methyl-1,3-propanediol, 2-amino-2-ethyl-1,3-propanediol, 3-amino-1,2-propanediol, 2-amino-2-hydroxymethyl-1,3-propanediolamine, sodium hydroxide, potassium hydroxide, ammonium hydroxide, sodium carbonate, potassium carbonate, ammonium carbonate, sodium hydrogen carbonate, potassium hydrogen carbonate, ammonium hydrogen carbonate, tetramethylammoniumhydroxide, tetraethylammoniumhydroxide, tetrapropylammoniumhydroxide, tetraisopropylammoniumhydroxide, aminomethanol, 2-aminoethanol, 3-aminopropanol, 2-aminopropanol, methylamine, ethylamine, propylamine, isopropylamine, dimethylamine, diethylamine, dipropylamine, diisopropylamine, trimethylamine, triethylamine, tripropylamine, triisopropylamine, and the like. However, any other compound may be used as long as the compound is soluble in water or the aqueous organic solvent such as alcohol and the solution is basic.

The pattern formed through the development is subsequently rinsed with a rinse liquid so as to remove the developer. Preferable examples of the rinse liquid include methanol, ethanol, isopropyl alcohol, water, and the like which are compatible with the developer.

The pattern bound in the foregoing process is subjected to heat treatment at temperature ranging from 20° C or higher to 200° C. or lower, thereby binding a resin pattern made of the photosensitive resin film of the present invention with high resolution. The resin pattern has high heat resistance and an excellent mechanical property. In the foregoing manner, it is possible to produce the FPC photosensitive cover lay film with the photosensitive resin film of the present invention.

Embodiment 2

The following description explains Embodiment 2 of the present invention. Note that, the present invention is not limited to this.

The photosensitive resin composition according to the present embodiment includes at least the polyimide resins (G) and the phosphazene compound (H), and further includes (meth)acrylic compounds (I). Among them, as the polyimide resins, the soluble polyimide resin (G-1) which has a carboxyl group and/or a hydroxyl group and is soluble in an organic solvent is used. As the phosphazene compound (H), the phenoxyphosphazene compound (H-1) having a phenolic hydroxyl group and/or the cross-linked phenoxyphosphazene compound (G-2) obtained by cross-linking the phenoxyphosphazene compound (H-1) is used.

The photosensitive resin composition according to the present invention uses the soluble polyimide resin (G-1) having a carboxyl group and/or a hydroxyl group. On this account, it is possible to give the heat resistance, the anti-bending property, the excellent mechanical property, the electric insulation property, and the anti-chemical property to the cured resin obtained by curing the photosensitive resin composition (for example, the photosensitive resin film). Particularly, the soluble polyimide resin (G-1) has the carboxyl group and/or the hydroxyl group, so that it is possible to carry out the water development of the photosensitive resin composition. Further, other component (J) may be included as required. As the other component, for example, it is possible to include a component which gives properties such as the bonding property, the flame retardancy, the heat resistance, the anti-bending property to the photosensitive resin composition. Note that, the photosensitive resin film according to the present embodiment is formed by using the photosensitive resin composition according to the present embodiment. The following details components thereof.

[Polyimide Resins (G)]

As the polyimide resins according to the present embodiment, at least the soluble polyimide resin (G-1) is used. The soluble polyimide resin (G-1) of the present embodiment has a carboxyl group and/or a hydroxyl group in its side chain, and is soluble in the organic solvent. The "soluble polyimide resin" is a term given to such polyimide resin for ease of description.

The soluble polyimide resin (G-1) is not particularly limited as long as the resin is the polyimide resin defined in the foregoing manner. However, it is preferable that: the polyimide resin has a structure including at least one kind of an organic solvent solubility providing component selected from an aliphatic compound component, an alicyclic compound component, and an alkylene oxide providing component of a bisphenol compound.

<Soluble Polyimide Resin (G-1)>

As described above, the "soluble" of the soluble polyimide resin (G-1) means a condition under which the resin is soluble in an organic solvent. More specifically, in the present invention, the "soluble" means a condition under which 1.0 g or more of the resin is dissolved in 100 g of the organic solvent at 20° C. As to the solubility, it is preferable that 1.0 g or more of the soluble polyimide resin (G-1) of the present invention is dissolved in the 100 g of the organic solvent at 20° C., but it is more preferable that 5.0 g or more of the resin is dissolved in 100 g of the organic solvent at 20° C., and it is still more preferable that 10.0 g or more of the resin is dissolved in 100 g of the organic solvent at 20° C. In case where the solubility allows less than 1 g of the resin to be dissolved in 100 g of the organic solvent at 20° C., it is more difficult to form the photosensitive resin film so as to have a desired thickness in forming the photosensitive resin film by using the photosensitive resin composition. The organic solvent is not particularly limited, but examples thereof include: a formamide solvent such as N,N-dimethylformamide and N,N-diethylformamide; an ether solvent such as 1,4-dioxane, 1,3-dioxolane, and tetrahydrofuran; and the like.

A weight-average molecular weight of the soluble polyimide resin (G-1) preferably ranges from 5000 to 200000, more preferably from 10000 to 100000. When the weight-average molecular weight is less than 5000, the photosensitive resin film produced by using the photosensitive resin composition of the present invention is likely to be cloggy, and the cured photosensitive resin film is likely to be deteriorated in terms of the anti-bending property. While, when the weight-average molecular weight exceeds 200000, the solution of the soluble polyimide resin (G-1) has excessively high viscosity, so that it tends to be hard to treat the resultant. Further, the developing property of the produced photosensitive resin film is likely to drop. Note that, the weight-average molecular weight can be measured by a size exclusion chromatography (SEC), for example, HLC8220GPC (product of Tosoh Corporation).

As the hydroxyl group of the soluble polyimide resin (G-1), it is preferable to use a phenolic hydroxyl group. Further, a weight-average molecular weight of each carboxyl group and/or each hydroxyl group of the soluble polyimide resin (hereinafter, the weight-average molecular weight is referred to as an acid equivalent) is preferably 7000 or less, more preferably 5000 or less, most preferably 3000 or less. When the acid equivalent exceeds 7000, it is likely to be hard to carry out water development of the photosensitive resin film produced by using the photosensitive resin composition of the present invention. Note that, it is possible to obtain the acid equivalent of the soluble polyimide resin (G-1) by calculation based on a composition of the soluble polyimide resin (G-1).

Further, as will be described later, it is preferable that the soluble polyimide resin (G-1) of the present invention has at least one kind of an unsaturated double bond, selected from an acryl group, a methacryl group, a vinyl group, and an allyl group, in its side chain. The soluble polyimide resin (G-1) has a photosensitive group such as the acryl group, the methacryl group, the vinyl group, and the allyl group in its side chain, so that it is possible to improve a curing property of an exposed portion in exposing the photosensitive resin composition.

Note that, in the soluble polyimide resin (G-1), an acid dianhydride component and a diamine component are used as monomer components serving as materials, and these monomer components are reacted with each other, thereby polymerizing a polyamide acid (polyamic acid). Further, the resultant is imidized, thereby obtaining the soluble polyimide resin.

Further, also in the present embodiment, a specific structure of the soluble polyimide resin (G-1) is not particularly limited. However, as in Embodiment 1, an acid dianhydride and a diamine each of which has a specific structure described later are used as the monomer components, so that it is possible to obtain the soluble polyimide resin (G-1) which is more suitable for the photosensitive resin composition according to the present invention. Note that, a production method of the soluble polyimide resin (G-1) will be described later.

<Acid Dianhydride Component>

In the soluble polyimide resin (G-1) favorably used in the present invention, the acid dianhydride serving as a material is not particularly limited as long as the acid dianhydride is a carboxylate dianhydride having a carboxyl group. Further, in order to improve the heat resistance of the photosensitive resin composition, it is preferable to use a carboxylate dianhydride having one to four aromatic rings or an alicyclic carboxylate dianhydride. Further, in order to improve the solubility in the organic solvent, it is preferable to use a carboxylate dianhydride having two or more aromatic rings as at least a part of the photosensitive resin composition, and it is more preferable to use a carboxylate dianhydride having four or more aromatic rings as at least a part of the photosensitive resin composition.

Specific examples of a compound serving as the acid dianhydride include: aliphatic or alicyclic tetracarboxylate dianhydride such as butanetetracarboxylate dianhydride and 1,2, 3,4-cyclobutanetetracarboxylate dianhydride; aromatic tetracarboxylate dianhydride such as pyromellitic acid dianhydride, 3,3',4,4'-benzophenone tetracarboxylate dianhydride, 3,3',4,4'-biphenylsulfonete tracarboxylate dianhydride, 2,2'-bis(hydroxyphenyl)propanedibenzoate)-3,3',4,4'-tetracaboxylate dianhydride, 2,3(,3,4'-biphenylether tetracarboxylate dianhydride, 3,4,3',4'-biphenylethertetracarboxylate dianhydride, and biphenyl-3,4,3',4'-tetracarboxylate dianhydride; aliphatic tetracarboxylate dianhydride such as 1,3,3a,4,5,9b-hexahydro-2,5-dioxo-3-furanyl)-naptho[1,2-c]furan-1, and 3-dione, and the like, but the acid dianhydride component is not limited to them. The acid dianhydrides may be independently used, or a suitable combination of two or more kinds may be used.

As the acid dianhydride, it is more preferable to use a part of the acid dianhydride, having two or more aromatic rings, such as 2,2'-bis(4-hydroxyphenyl)propane dibenzoate-3,3',4,4'-tetra carboxylate dianhydride, 2,3',3,4'-biphenylether tetra carboxylate dianhydride, 3,4,4'-biphenylether tetra carboxylate dianhydride, and biphenyl-3,4,3',4'-tetra carboxylate dianhydride. These compounds can be easily synthesized, and each compound allows the obtained soluble polyimide resin (G-1) to have high solubility in the organic solvent.

<Diamine>

In the soluble polyimide resin (G-1) favorably used in the present invention, a diamine component serving as a material is not particularly limited, but it is preferable to use a diamine having one or more carboxyl groups and/or one or more hydroxyl groups in its molecule (for ease of description, this diamine is referred to as a hydroxy diamine) as at least a part of the material in terms of the water development. Further, it is preferable to use an aromatic diamine having one or more aromatic tins in its molecule as at least a part of the material in terms of the heat resistance and the anti-chemical property. Thus, particularly in case where an aromatic diamine having one or more carboxyl groups and one or more hydroxyl groups in its molecule (for ease of description, this diamine is referred to as a hydroxy aromatic diamine) is used as a part of the material, it is possible to give the heat resistance and the water developing property to the photosensitive resin film made of the photosensitive resin composition, so that use of the hydroxy aromatic diamine is more preferable.

The hydroxy aromatic diamine is not particularly limited as long as the diamine is an aromatic diamine having one or more carboxyl groups and/or one or more hydroxyl groups in its molecule, but it is preferable to use as a part of the material for the soluble polyimide resin (G-1) a hydroxy aromatic diamine represented by the following formula (19)

(19)

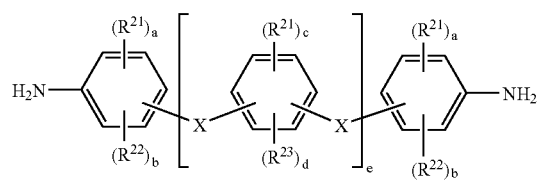

where $R^{12}$ represents a hydroxyl group or a carboxyl group, and $R^{22}$ and $R^{23}$ may be different from each other, and each of $R^{22}$ and $R^{23}$ represents a hydrogen atom, an alkyl group containing 1 to 9 carbon atoms, an alcoxy group containing 2 to 10 carbon atoms, or $COOR^{24}$ ($R^{24}$ represents an alkyl group containing 1 to 9 carbon atoms), and X represents —O—, —S—, —SO$_2$—, —C(CH$_3$)$_2$—, —CH$_2$—, —C(CH$_3$)

($C_2H_5$)—, or $C(CF_3)_2$—, each of a and b is an integer not less than 0 so that a+b=4, and each of c and d is an integer not less than 0 so that c+d=4, and e is an integer ranging from 0 to 10.

Further, among the hydroxy aromatic diamines, the hydroxyl diamine having a carboxyl group is not particularly limited as long as the diamine has a carboxyl group. However, examples thereof include: diamino benzoic acid such as 3,5-diamino benzoic acid; carboxy biphenyl compounds such as 3,3'-diamino-4,4'-dicarboxybiphenyl, 4,4'-diamino-2,2',5,5'-tetracarboxybiphenyl; carboxydiphenyl alkanes such as 4,4'-diamino-3,3'-dicarboxydiphenylmethane and 3,3'-diamino-4,4'-dicarboxydiphenylmethane; carboxy diphenylether compounds such as 4,4'-diamino-2,2',5,5'-tetracarboxy-diphenylether; diphenylsulfone compounds such as 3,3'-diamino-4,4'-dicarboxydiphenylsulfone; bis(hydroxy phenoxy)biphenyl compounds such as 2,2-bis[4-(4-amino-3-carboxyphenyl)phenyl]propane; bis[(-carboxy phenoxy) phenyl]sulfone compounds such as 2,2-bis [4-(4-amino-3-carboxy phenoxy)phenyl]sulfone; and the like.

Further, a particularly preferable example of a hydroxy aromatic diamine having a carboxyl group is a hydroxy aromatic diamine represented by the following formula (20).

(20)

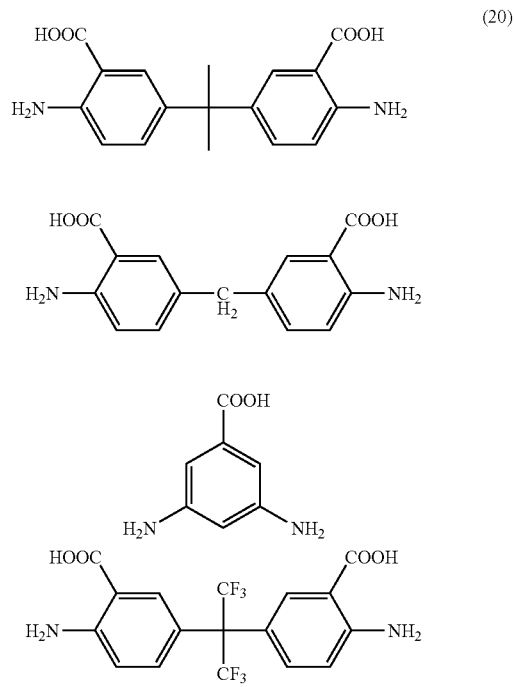

Further, among the hydroxy aromatic diamines, the hydroxy aromatic diamine having a hydroxyl group is not particularly limited as long as the hydroxy aromatic diamine has a hydroxyl group. However, examples thereof include: compounds such as 2,2'-diaminobisphenol A, 2,2'-bis(3-amino-4-hydroxyphenyl)hexafluoropropane, bis(2-hydroxy-3-amino-5-methylphenyl)methane, 2,6-di{(2-hydroxy-3-amino-5-methylphenyl)methyl}-4-methylphenol, 2,6-di{(2-hydroxy-3-amino-5-methypphenyl)methyl}-4-hydroxybenzoic acid propyl, and the like.

Further, a particularly preferable example of a hydroxy aromatic diamine having a hydroxyl group is a hydroxy aromatic diamine represented by the following formula (21).

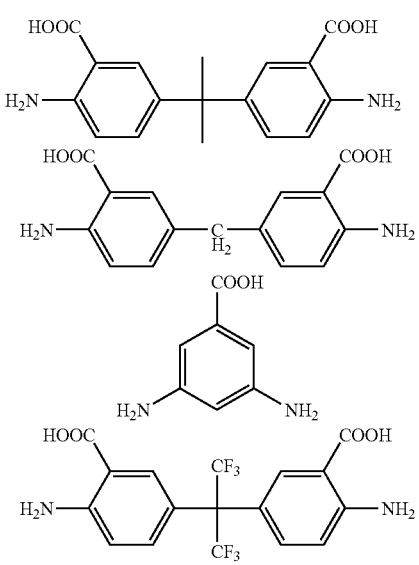

(21)

The hydroxy aromatic diamines may be independently used, or a suitable combination of two or more kinds may be used. The hydroxy aromatic diamine is used as a part of the material, so that the acid equivalent of the obtained soluble polyimide resin (G-1) drops, thereby improving the developing property with respect to the alkaline aqueous solution.

Not only the foregoing aromatic diamine but also other diamines may be simultaneously used as a part of the material. Specific examples of other diamines include compounds such as bis [4-(3-amino phenoxy)phenyl]sulfone, reactive silicone (hereinafter, referred to as silicon diamine) having an amino group in each end of its siloxane structure, [bis(4-amino-3-carboxy)phenyl]methane, and the like. Particularly, it is preferable to use silicon diamine since it is possible to drop the elastic mudulus of the photosensitive resin film. Such other diamines may be independently used, or a suitable combination of two or more kinds may be used.

<Synthesis of Soluble Polyimide Resin (C-1)>

It is possible to produce the soluble polyimide resin (G-1) used in the present in accordance with a known method. Specifically, it is possible to produce the soluble polyimide resin (G-1) in accordance with a method similar to the first method in Embodiment 1 for producing the soluble polyimide resin (E-1). That is, an acid dianhydride component and a diamine component are used as materials (monomer components), and these monomer components are polycondensed so as to synthesize a polyamide acid (polyamic acid) serving as a precursor, and the resultant is chemically or thermally subjected to dehydration cyclization (imidization). In this manner, these operations are performed in two steps. Also in synthesizing and imidizing the polyamide acid, it is possible to adopt a method similar to the first method.

Further, as the diamine component, for example, it is possible to use a diamine solution obtained by dissolving the diamine in an organic solvent in the presence of inert atmosphere such as argon and nitrogen or obtained by dispersing the diamine in the organic solvent in a slurry manner. Further, as the acid dianhydride component, for example, it is possible to use a solution obtained by dissolving the acid dianhydride in the organic solvent or dispersing the acid anhydride in the organic solvent in a slurry manner or it is possible to use the acid dianhydride in a solid phase.

<Soluble Polyimide Resin (G-1) having Unsaturated Double Bond>

Further, it is preferable that the soluble polyimide resin (G-1) according to the present invention is a soluble polyimide resin having at least one kind of an unsaturated double bond, selected from an acryl group, a methacryl group, a vinyl group, a vinyl group, and an allyl group, in its side chain (for ease of description, this soluble polyimide resin is referred to as a double bond polyimide resin). The soluble polyimide resin (G-1) has the unsaturated double bond, so that it is possible to carry out cross-linking reaction of the soluble polyimide resin (G-1) and the (meth)acrylic compounds (I), or it is possible to carry out cross-linking reaction of the soluble polyimide resins (G-1).

It is possible to obtain the double bond polyimide resin by reacting a compound having an unsaturated double bond with the soluble polyimide resin (G-1) and denaturalizing the resultant. The compound having the unsaturated double bond is not particularly limited as long as the compound reacts with the carboxyl group and/or the hydroxyl group positioned in the side chain of the soluble polyimide resin (G-1). However, examples of the compound include: halogen allyl, having an unsaturated double bond, such as an epoxy compound, (meth)acrylate anhydride, and allyl bromide; and the like.

The reaction of the soluble polyimide resin (G-1) and the epoxy compound having the unsaturated double bond can be carried out, for example, by reacting the soluble polyimide resin (G-1) with the epoxy compound in an inert solvent and in the presence of an organic base such as pyridine or triethylamine. In this manner, it is possible to obtain the desired double bond polyimide resin.

It is preferable that a reaction temperature in the reaction is 40° C. or higher and 130° C. or lower at which the epoxy group reacts with the carboxyl group and/or the hydroxyl group. Particularly, it is preferable to carry out the reaction at such temperature that heat does not cause reaction such as polymerization of the unsaturated double bond. Specifically, the reaction temperature is more preferably 40° C. or higher and 100° C. or lower, still more preferably 50° C. or higher and 80° C. or lower. Further, reaction time is suitably set, but it is preferable that the reaction time ranges from 1 hour to 20 hours.

A reaction solution obtained by the foregoing reaction may be used in a solution state after the reaction. Alternatively, it may be so arranged that: the compound is deposited in an alcohol solvent such as methanol, and the resultant is rinsed with the alcohol solvent as required.

The epoxy compound having an unsaturated double bond is not particularly limited as long as the compound has an epoxy group and an unsaturated double bond in its molecule. However, examples thereof include glycidyl acrylate, glycidyl methacrylate, allyl glycidyl ether, glycidyl vinyl ether, and the like. Among them, it is particularly preferable to use glycidyl methacrylate due to easiness to obtain at low cost and its favorable reactivity.

Next, an example of the reaction of the soluble polyimide resin (G-1) and the (meth)acrylate anhydride is reaction in which: a hydroxyl group positioned in the side chain of the soluble polyimide resin (G-1) and the (meth)acrylate anhydride are condensed in an inert solvent. In this manner, it is possible to obtain the desired double bond polyimide resin.

It is preferable that a reaction temperature in the reaction is 0° C. or higher and 100° C. or lower at which the hydroxyl group positioned in the side chain of the soluble polyimide resin (G-1) can be acylated. Particularly, it is preferable to carry out the reaction at such temperature that heat does not cause reaction such as polymerization of the unsaturated double bond. Specifically, the reaction temperature is more preferably 10° C. or higher and 100° C. or lower, still more preferably 20° C. or higher and 80° C. or lower. Further, reaction time is suitably set, but it is preferable that the reaction time ranges from 1 hour to 20 hours.

In order to remove the (meth)acryl acid generated by the foregoing reaction, it is preferable to treat the reaction solution obtained by the reaction as follows: the compound is deposited in an alcohol solvent such as methanol, and the compound is rinsed with the alcohol solvent as required.

Further, an example of the reaction of the soluble polyimide resin (G-1) and allyl halide is a reaction in which: the hydroxyl group positioned in the side chain of the soluble polyimide resin (G-1) and the ally halide are reacted with each other in an inert solvent and in an organic base such as pyridine or triethylamine. In this manner, it is possible to obtain the desired double bond.

It is preferable that the reaction temperature is 0° C. or higher and 100° C. or lower which allows reaction of the soluble polyimide resin (G-1) and the allyl halide. Particularly, it is preferable to carry out the reaction at such temperature that heat does not cause reaction such as polymerization of the unsaturated double bond. Specifically, the reaction temperature is more preferably 0° C. or higher and 80° C. or lower, still more preferably 20° C. or higher and 50° C. or lower. The reaction time can be suitably set, but the reaction time preferably ranges from 1 hour to 20 hours.

It is preferable to treat the reaction solution obtained in the foregoing reaction by depositing the compound in an alcohol solvent such as methanol and rinsing the resultant with the alcohol solvent as required.

In any one of the foregoing reactions, in order to keep the developing property with respect to the alkaline aqueous solution, it is preferable not to react all the carboxyl groups and/or all the hydroxyl groups in the side chain of the soluble polyimide resin (G-1) but to adjust an equivalent of the target compound having an unsaturated monomer so that the carboxyl groups and/or the hydroxyl groups remain. Specifically, it is necessary only to adjust an acid equivalent of the reacted double bond polyimide resin to 7000 or less.

Further, in order to prevent the unsaturated double bond from being polymerized during the reaction, it is preferable to add a polymerization inhibitor. Examples of the polymerization inhibitor include a hydroquinone derivative such as p-methoxyphenol, phenothiazine, N-nitrohydroxylamine salts, and the like.

The soluble polyimide resin (G-1) obtained by introducing a photopolymerizable group and/or a thermally polymerizable group such as the unsaturated double bond in this manner has a favorable curing property and a favorable bonding property.

Note that, the double bond polyimide resin is arranged in any manner as long as the soluble polyimide resin (G-1) has an unsaturated double bond in its side chain. That is, the unsaturated double bond of the soluble polyimide resin (G-1) is not limited to the foregoing functional groups, and the soluble polyimide resin (G-1) may have a functional group having an unsaturated double bond other than the foregoing functional groups.

[Phosphazene Compound (H)]

In the photosensitive resin composition according to the present invention, a compound having a phenolic hydroxyl group, that is, the phenoxyphosphazene compound (H-1) and/or the cross-linked phenoxyphosphazene compound (G-2) are used. The cross-linked phenoxyphosphazene compound (G-2) is a phosphazene compound obtained by cross-linking the phenoxyphosphazene compound (H-1).

The phenoxyphosphazene compound (H-1) and/or the cross-linked phenoxyphosphazene compound (G-2) are included, so that it is possible to give the flame retardancy without losing the heat resistance of the obtained photosensitive resin composition. Particularly, the phosphazene compound used in the present invention has a phenolic hydroxyl group in its molecule, so that it is possible to remarkably improve the compatibility with the soluble polyimide resin (G-1) due to influence of the phenolic hydroxyl group. Thus, in the obtained photosensitive resin composition, it is possible to suppress deposition (bleeding or juicing) of the flame retardant on the surface, thereby further improving the flame retardancy.

Moreover, the phenolic hydroxyl group is included in the molecule, so that the phosphazene compound allows formation of a mesh structure by reacting particularly with an epoxy resin component (described later) in curing the photosensitive resin composition. Thus, efficient curing is possible, thereby obtaining a cured product having excellent heat resistance. Further, it is also possible to improve alkaline solubility compared with the conventional phosphazene compound.

<Phenoxyphosphazene Compound (H-1)>

The phenoxyphosphazene compound (H-1) used in the present invention is not particularly limited as long as the compound is a phosphazene compound having a phenolic hydroxyl group. Specifically, it is preferable to use at least one of a circular phenoxyphosphazene compound (G-11) and a chain phenoxyphosphazene compound (G-12).

Structures, properties, production methods, and the like of the circular phenoxyphosphazene compound (G-11) and the chain phenoxyphosphazene compound (G-12) are the same as those of the circular phenoxyphosphazene compound (A-11) and the chain phenoxyphosphazene compound (A-12) in Embodiment 1.

<Cross-Linked Phenoxyphosphazene Compound (G-2)>

As described above, the cross-linked phenoxyphosphazene compound (G-2) has at least one phenolic hydroxyl group, and is a phosphazene compound obtained by cross-linking the phenoxyphosphazene compound (H-1). The cross-linked phenoxyphosphazene compound (G-2) may be obtained by cross-linking the phenoxyphosphazene compound (H-1) in accordance with a known method, but it is preferable to cross-link the phenoxyphosphazene compound (H-1) with a phenylene cross-linking group.

Any cross-linking group may be used as the phenylene cross-linking group as long as a phenyl group is included in a structure, but it is possible to use the same cross-linking group as that in Embodiment 1.

Further, also in the present embodiment, in case of synthesizing (producing) the cross-linked phenoxyphosphazene compound (G-2), any compound may be used as the phenoxyphosphazene compound, but it is preferable to use the circular phenoxyphosphazene compound (G-11) and/or the chain phenoxyphosphazene compound (G-12). At this time, it is preferable to use the phenylene cross-linking group as the cross-linking group.

Further, as in Embodiment 1, in case where (1) the circular phenoxyphosphazene compound (G-11) and/or the chain phenoxyphosphazene compound (G-12) are used as the phenoxyphosphazene compounds and (2) the phenylene cross-linking group is used as the cross-linking group, when these conditions are satisfied, it is preferable to define a cross-linking condition so as to satisfy the following conditions (3) and (4).

That is, it is preferable that: (3) the phenylene cross-linking group intervenes between two oxygen atoms of the phenoxyphosphazene compound (H-1) (the circular phenoxyphosphazene compound (G-11) and/or the chain phenoxyphosphazene compound (G-12)) which are obtained by desorbing a phenyl group and a hydroxyphenyl group, and (4) a ratio at which phenyl groups and hydroxyphenyl groups are included in the cross-linked phenoxyphosphazene compound ranges from 50 to 99.9% with respect to a total of phenyl groups and hydroxyphenyl groups of the foregoing phenoxyphosphazene compound.

When the cross-linked phenoxyphosphazene compound (G-2) satisfying the conditions (1) to (4) is used, it is possible to further improve the flame retardancy of the heat-resistance resin composition. Note that, the cross-linked phenoxyphosphazene compound satisfying the conditions (1) to (4) is referred to as phenylene cross-linked phenoxyphosphazene compounds.

<Example of Synthesis (Production) of Cross-linked Phenoxyphosphazene Compound (G-2)>

A production method of the cross-linked phenoxyphosphazene compound (G-2) is not particularly limited, but it is possible to produce the cross-linked phenoxyphosphazene compound (G-2) in the same manner as in Embodiment 1.

Note that, also in the present embodiment, an amount of the phenoxyphosphazene compound (inclusive the cross-linked compound) blended is not particularly limited. However, with respect to 100 parts by weight (total weight) of the soluble polyimide resin (G-1) and the (meth)acrylic compounds (I) described later, the amount preferably ranges from 1 to 100 parts by weight, more preferably from 1 to 50 parts by weight, particularly preferably from 1 to 40 parts by weight.

When the amount of the phenoxyphosphazene compound used is less than 1 part by weight with respect to 100 parts by weight (total weight) of the soluble polyimide resin (G-1) and the (meth)acrylic compounds (I), it may be impossible to obtain a sufficient flame retardant effect. While, when the amount exceeds 100 parts by weight with respect to 100 parts by weight (total weight), the half-cured photosensitive dry film resist (in a B stage state) may be cloggy, and the resin may exude at the time of thermal pressure. Moreover, this may have a bad influence on properties of the cured product. Thus, it is not preferable that the amount exceeds 100 parts by weight.

[(Meth)acrylic Compounds' (I)]

Next, the (meth)acrylic compounds (I) are described as follows. The photosensitive resin composition according to the present invention includes the (meth)acrylic compounds (I), so that it is possible not only to give a favorable curing property but also to give fluidity at the time of thermal lamination by dropping the viscoelasticity of the photosensitive resin film made of the photosensitive resin composition at the time of heat treatment. That is, it is possible to carry out the thermal lamination at relatively low temperature, so that indented portions of a circuit can be embedded therein.

In the present invention, the (meth)acrylic compounds (I) are compound selected from a (meth)acryl compound, epoxy (meth)acrylate, polyester(meth)acrylate, urethane(meth)acrylate, and imide(meth)acrylate. Note that, in the present invention, (meth)acryl means acryl and/or methacryl.

The (meth)acrylic compounds may be independently used, or a suitable combination of two or more kinds may be used. In the present invention, a total weight of the (meth)acrylic compounds (I) included in the photosensitive resin composition of the present invention preferably ranges from 1 to 100 parts by weight, more preferably from 1 to 80 parts by weight, still more preferably from 1 to 50 parts by weight, with respect to 100 parts by weight of the soluble polyimide resin (G-1).

In case where the (meth)acrylic compounds (I) whose amount exceeds 100 parts by weight with respect to 100 parts by weight of the soluble polyimide resin (G-1), the heat resistance of the photosensitive resin film made of the obtained photosensitive resin composition drops, so that the (meth)acrylic compounds (I) may exude at the time of the thermal lamination.

As the (meth)acrylic compounds (I) used in the photosensitive resin composition of the present invention, particularly, it is preferable to use a (meth)acrylic compounds (I) having one or more epoxy groups and one or more (meth)acryl groups in its molecule. By using such (meth)acrylic compounds (I), it is possible to improve the anti-hydrolysis property of the photosensitive resin film made of the obtained photosensitive resin composition and the bonding strength with respect to a copper foil.

The (meth)acrylic compounds (I) having one or more epoxy groups and one or more (meth)acryl groups in its molecule are not particularly limited, but examples thereof include: a glycidyl compound such as glycidyl methacrylate; and epoxy acrylate such as NK NK oligo EA-1010 and EA-6310 (each of which is a commercial name) produced by SHIN-NAKAMURA CHEMICAL CO., LTD.

Further, as the (meth)acrylic compounds (I) used in the photosensitive resin composition of the present invention, it is preferable to additionally use epoxy (meth)acrylate having two or more hydroxyl groups in its molecule, and it is more preferable to use epoxy (meth)acrylate having four or more hydroxyl groups in its molecule. Such epoxy (meth)acrylate is used, so that the solubility of the photosensitive resin film made of the photosensitive resin composition is improved, thereby realizing shorter developing time.

The epoxy(meth)acrylate having two or more hydroxyl groups in its molecule is not particularly limited, but examples thereof include: bisphenol A type epoxy acrylate such as LIPOXY SP-2600 (commercial name: product of Showa Highpolymer Co., Ltd.), NK oligo EA-1020 and NK oligo EA-6340 (both of which are commercial names: products of SHIN-NAKAMURA CHEMICAL CO., LTD.), KARAYAD R-280 and KARAYAD R-190 (both of which are commercial names: products of Nippon Kayaku Co., Ltd.), and Ebercryl 600 and Ebercryl 3700 (both of which are commercial names: products of DAICEL-UCB Company LTD.); denaturalized bisphenol A type epoxy acrylate such as Ebercryl 3200, Ebercryl 3500, Ebercryl 3701, and Ebercryl 3703 (all of which are commercial names: products of DAICEL-UCB Company LTD.); phenolnovolak epoxy acrylate such as NK oligo EA-6320 and NK oligo EA-6340; denaturalized 1,6-hexanediol acrylate such as KARAYAD R-167 and MAX-2104 (both of which are commercial names: products of Nippon Kayaku Co., Ltd.), and denacol acrylate DA-212 (commercial name: Nagase Chemical Industries Co., Ltd.); denaturalized phthalate diacrylate such as denacol acrylate DA-721 (commercial name: product of Nagase Chemical Industries Co., Ltd.); cresol novolak epoxy acrylate such as NK oligo EA-1020 (commercial name: product of SHIN-NAKAMURA CHEMICAL CO., LTD.); and the like.

In the photosensitive resin composition used in the present invention, it is possible to use not only the epoxy (meth)acrylate and the (meth)acrylic compounds having one or more epoxy groups and one or more (meth)acryl groups in its molecule but also polyester(meth)acrylate, urethane(meth)acrylate, imide(meth)acrylate, and other (meth)acrylic compound.

By using polyester(meth)acrylate, it is possible to give the flexibility to the photosensitive resin film made of the obtained photosensitive resin composition. The polyester (meth)acrylate is not particularly limited, but examples thereof include ARONIX M-5300, ARONIX M-6100, and ARONIX M-7100 (all of which are commercial names: product of TOAGOSEI CO., LTD.), and the like.

By using urethane(meth)acrylate, it is possible to give the flexibility to the photosensitive resin film made of the obtained photosensitive resin composition. The urethane (meth)acrylate is not particularly limited, but examples thereof include ARONIX M-1100 and ARONIX M-1310 (both of which are commercial names: products of TOAGOSEI CO., LTD.), KARAYAD UX-4101 (commercial name: product of Nippon Kayaku Co., Ltd.), and the like.

By using imide(meth)acrylate, it is possible to improve the adhesiveness of the base material (polyimide film, copper foil, and the like) with which the photosensitive resin film made of the obtained photosensitive resin composition is combined. The imide (meth)acrylate is not particularly limited, but examples thereof include ARONIX TO-1534, ARONIX TO-1429, and ARONIX TO-1428 (all of which are commercial names: products of TOAGOSEI CO., LTD.).

Further, other(meth)acrylic compound is not particularly limited. However, in order to improve cross-linked density based on light emission which will be described later, it is preferable to use a multifunctional (meth)acrylic compound having at least two unsaturated double bonds. Further, in order to give the heat resistance to the photosensitive resin film made of the obtained photosensitive resin composition, it is preferable to use a (meth)acrylic compound having at least one aromatic ring and/or one heterocycle in its molecule.

The (meth)acrylic compound having at least one aromatic ring and/or one heterocycle in its molecule and having at least two unsaturated double bonds is not particularly limited, but examples thereof include: bisphenol A EO denaturalized di(meth)acrylate such as ARONIX M-210 and ARONIX M-211B (both of which are commercial names: products of TOAGOSEI CO., LTD.), NK ester ABE-300, NK ester A-BPE-4, NK ester A-BPE-10, NK ester A-BPE-20, NK ester A-BPE-30, NK ester BPE-100, and NK ester BPE-200 (all of which are commercial names: products of SHIN-NAKAMURA CHEMICAL CO., LTD.); bisphenol F EO denaturalized (n=2 to 20) di(meth)acrylate such as ARONIX M-208 (commercial name: product of TOAGOSEI CO., LTD.); bisphenol A PO denaturalized (n=2 to 20) di(meth)acrylate such as denacol acrylate DA-250 (commercial name: Nagase Chemical Industries Co., Ltd.) and BISCOAT #540 (commercial name: product of Osaka Organic Chemical Industry Ltd.); phthalate PO denaturalized diacrylate such as denacol acrylate DA-721 (commercial name: Nagase Chemical Industries Co., Ltd.); and the like. Further, as the (meth)acrylic compound having no aromatic ring, for example, it is possible to use: isocyanuric acid EO denaturalized diacrylate such as ARONIX M-215 (commercial name: product of TOAGOSEI CO., LTD.); and isocyanuric acid EO denaturalized triacrylate such as ARONIX M-315 (commercial name: product of TOAGOSEI CO., LTD.) and NK ester A-9300. Note that, the "EO denaturalized" means that there is an ethylene oxide denaturalized portion, and the "PO denaturalized" means that there is a propylene oxide denaturalized portion.

Among the (meth)acrylic compounds, it is particularly preferable to use a (meth)acrylic compound in which the number of recurring units (—($CH_2CH_2O$)—) of an ethylene oxide denaturalized (EO denaturalized) portion in its molecule or the number of recurring units (—($CH(CH_3)CH_2O$)—) of a propylene oxide denaturalized (PO denaturalized) portion in its molecule is 10 or more. Due to 10 or more recurring units described above, it is possible to give thermal fluidity to the photosensitive resin film made of the obtained photosensitive resin composition at the time of lamination, thereby improving the solubility with respect to the alkaline aqueous solution.

The (meth)acrylic compound having 10 or more recurring units of an EO denaturalized portion in its molecule or 10 or more recurring units of a PO denaturalized portion in its molecule is not particularly limited, but examples thereof include: bisphenol A EO denaturalized di(meth)acrylate such as NK ester A-BPE-10, NK ester A-BPE-20, NK ester A-BPE-30, NK ester A-BPE-100, and NK ester A-BPE-200 (all of which are commercial names: products of SHIN-NAKAMURA CHEMICAL CO., LTD.); bisphenol F EO denaturalized (n=10 to 20) di(meth)acrylate; bisphenol A PO denaturalized (n=10 to 20) di(meth)acrylate; and the like.

With respect to a total weight of all the (meth)acrylic compounds (I) contained in the photosensitive resin composition of the present invention, an amount of the (meth)acrylic compound having 10 or more recurring units of an EO denaturalized portion in its molecule or 10 or more recurring units of a PO denaturalized portion in its molecule is preferably at least 10 parts by weight, more preferably 20 parts by weight or more.

[Other Component (J)]

The photosensitive resin composition of the present embodiment may include not only the soluble polyimide resin (G-1), the phenoxyphosphazene compound (H-1), and the (meth)acrylic compounds (I), but also other component (J). Examples of other component (J) include an epoxy resin (J-1), a curing promotion agent and/or curing agent (J-2), and a photoreaction initiator and/or sensitizer (J-3).

<Epoxy Resin (J-1)>

The photosensitive resin composition of the present invention contains the epoxy resin (J-1), so that it is possible to improve adhesiveness of the photosensitive resin film, made of the photosensitive resin composition, with respect to a copper foil, a polyimide film, and the like.

The epoxy resin is not particularly limited, but examples thereof include: a bisphenol A type epoxy resin such as Epikote 828, 834, 1001, 1002, 1003, 1004, 1005, 1007, 1010, and 1100L (all of which are commercial names: products of Japan Epoxy Resins Co., Ltd.); a brominated bisphenol A type epoxy resin such as Epikote 5050, 5051, and 5051H (all of which are commercial names: products of Japan Epoxy Resins Co., Ltd.); an o-cresolnovolak-type epoxy resin such as ESCN-220L, 220F, 220H, 220HH, 180H65, and 180S65 (all of which are commercial names: products of Japan Epoxy Resins Co., Ltd.); a novolak type epoxy resin such as 1032H60 (commercial name: product of Japan Epoxy Resins Co., Ltd.: trihydroxyphenylmethanenovolak type), EPPN-502H (commercial name: product of Nippon Kayaku Co., Ltd.: trihydroxyphenylmethanenovolak type), ESN-375 and ESN-185 (both of which are commercial names: products of Nippon Steel Chemical Group: naphthalenearalkylnovolak type), and 157S70 (commercial name: product of Japan Epoxy Resins Co., Ltd.: bisphenol A novolak type); bisphenol type epoxy resin such as YX4000H (commercial name: product of Japan Epoxy Resins Co., Ltd.); and the like.

Further, it is possible to use not only the foregoing resins but also a bisphenol A glycidyl ether type epoxy resin, a bisphenol F glycidyl ether type epoxy resin, novolak glycidyl ether type epoxy resin, a glycidyl ester type epoxy resin, a glycidyl ester type epoxy resin, a glycidyl amine type epoxy resin, a cyclic fatty epoxy resin, an aromatic epoxy resin, a halogenous epoxy resin, and the like.

As the epoxy resin (J-1) included in the photosensitive resin composition of the present invention, a suitable combination of two or more kinds selected from the foregoing epoxy resins may be used. Note that, with respect to 100 parts by weight of the soluble polyimide resin (G-1), an amount of the epoxy resin (J-1) preferably ranges from 1 to 100 parts by weight as required, more preferably from 1 to 50 parts by weight, particularly preferably from 2 to 30 parts by weight. When the amount of the epoxy resin is less than 1 part by weight with respect to 100 parts by weight of the soluble polyimide resin (G-1), the adhesiveness of the obtained photosensitive resin film drops. While, when the amount of the epoxy resin (J-1) exceeds 100 parts by weight, this may cause the heat resistance of the photosensitive resin film to drop and may cause the photosensitive resin film to be susceptible to damage upon being bent.

<Curing Promotion Agent/Curing Agent (J-2)>

In case where the epoxy resin (J-1) is used as a material of the photosensitive resin composition of the present invention, a curing promotion agent and/or a curing agent (J-2) may be added to the photosensitive resin composition in order to efficiently cure the photosensitive resin film made of the photosensitive resin composition. The curing promotion agent and/or the curing agent (J-2) is not particularly limited. However, examples thereof include imidazole compounds, acid anhydride, tertiary amines, hydrazines, aromatic amines, phenols, triphenylphosphins, organic peroxide, and the like. Among these curing promotion agents and/or the curing agents (J-2), one kind or a combination of two or more kinds is used.

With respect to 100 parts by weight of the soluble polyimide resin (G-1), an amount of the curing promotion agent and/or the curing agent (J-2) preferably ranges from 0.1 to 20 parts by weight, more preferably from 1 to 20 parts by weight, particularly preferably from 1 to 15 parts by weight. When the amount of the curing promotion agent and/or the curing agent (J-2) is less than 0.1 part by weight with respect to 100 parts by weight of the soluble polyimide resin (G-1), the epoxy resin (J-1) is not sufficiently cured. Adversely, when the amount exceeds 20 parts by weight, this may cause the heat resistance to drop.

<Photoreaction Initiator/Sensitizer (J-3)>

Further, it is preferable that the photosensitive resin composition of the present invention includes the photoreaction initiator and/or a sensitizer (J-3). In case where the photosensitive resin film made of the photosensitive resin composition obtained by adding the photoreaction initiator and/or the sensitizer (J-3) is exposed, it is possible to promote the cross-linking reaction or the polymerization reaction in an exposed area. On this account, it is possible to sufficiently differentiate the exposed area from an unexposed area in terms of the solubility of the photosensitive resin film with respect to the alkaline aqueous solution. As a result, it is possible to favorably develop a pattern on the photosensitive resin film.

Examples of the photoreaction initiator include a radical generation agent, a photocation generation agent, a photobase generation agent, photoacid generation agent, and the like.

As the radical generation agent, it is preferable to use an agent which generates a radical based on light whose wavelength is as long as a g-line. Examples thereof include: ketone compound such as 2,2-dimethoxy-1,2-diphenylethane-1-one and 2-hydroxy-2-methyl-1-phenyl-propane-1-one; phosphin oxide compound such as bis(2,4,6-trimethyl benzoyl)-phenylphosphinoxide and bis(2,6-dimethoxy benzoyl)-2,4,4-trimethyl-penthylphosphinoxide; titanocen compound such as bis(2,4-cyclopentadien-1-yl)-bis(2,6-difluoro-3-(1H-pyrrole-1-yl)-phenyl)titanium; and the like, but the radical generation agent is not limited to them. Among these compounds, it is particularly preferable to use a phosphin oxide compound or a titanocen compound.

Further, examples of the photocation generation agent include diphenyl iodonium saline such as diphenyl iodonium salt of dimethoxy anthraquinone sulphone; triphenyl sulphonium saline; pyrylinium saline; triphenyl onium saline; diazonium; and the like, but the photocation generation agent is not particularly limited. Note that, not only the foregoing saline but also an alicyclic epoxy or vinyl ether compound having a high cation-curing property may be mixed.

Further, examples of the photobase generation agent include: a benzylalcohol-urethane compound obtained by reacting nitro benzylalcohol or dinitro benzylalcohol with isocyanate; a phenylalcohol-urethane compound obtained by reacting nitro-1-phenylethylalcohol or dinitro-1-phenylethylalcohol with isocyanate; a propanol-urethane compound obtained by reacting dimethoxy-2-phenyl-2-propanol with isocyanate; and the like, but the photobase generation agent is not particularly limited.

Further, examples of the photoacid generation agent include: a compound which allows generation of sulfonic acid such as iodonium salt, sulfonium salt, and onium salt; a compound which allows generation of carboxylic acid such as naphthoquinone diazide; and the like, but the photoacid generation agent is not particularly limited. Further, it is preferable to use compounds such as diazonium salt and bis(trichloromethyl)triazine because each of these compounds allows generation of a sulfone group in response to irradiation of light.

While, the sensitizer is not particularly limited, but examples thereof include Michler's ketone, bis-4,4'-diethylamino benzophenone, 3,3'-carbonylbis(7-diethylamino) coumarin, 2-(p-dimethylamino styryl)quinoline, 4-(p-dimethylamino styryl)quinoline, and the like.

The photoreaction initiators and/or the sensitizers (J-3) may be independently used, or a combination of two or more kinds may be used.

With respect to 100 parts by weight (total weight) of the soluble polyimide resin (G-1) and the (meth)acrylic compounds (I), an amount of the photoreaction initiator and/or the sensitizer (J-3) preferably ranges from 0.001 to 10 parts by weight, more preferably from 0.01 to 10 parts by weight. When the amount of the photoreaction initiator and/or the sensitizer (J-3) is less than 0.001 parts by weight with respect to 100 parts by weight (total weight) of the soluble polyimide resin (G-1) and the (meth)acrylic compounds (I), or when the amount exceeds 10 parts by weight, it is impossible to obtain the sensitization effect, so that this may have bad influence on the developing property.

Further, in case of using the radical generation agent as the photoreaction initiator and the sensitizer in combination, it is possible to favorably use a combination of (i) peroxide such as bis(2,4,6-trimethyl benzoyl)phenylphosphinoxide and (ii) 3,3',4,4'-tetra(t-butylperoxycarbonyl)benzophenone.

[Photosensitive Resin Composition]

The photosensitive resin composition according to the present invention includes at least the soluble polyimide resin (G-1), the phenoxyphosphazene compound (H-1), and/or the cross-linked phenoxyphosphazene compound (G-2) obtained by cross-linking the phenoxyphosphazene compound (H-1), and the (meth)acrylic compounds (I). The photosensitive resin composition preferably further includes other component (J).

<Production of Photosensitive Resin Composition>

The production (preparation) method of the photosensitive resin composition according to the present invention, that is, the method for blending the foregoing components is not particularly limited. However, an example thereof is a method in which the components are dissolved in an organic solvent capable of favorably dissolving the components so as to obtain a solution of the photosensitive resin composition. More specifically, for example, it may be so arranged that the components are added to a proper solvent and the resultant is stirred so as to obtain the solution of the photosensitive resin composition, or it may be so arranged that the components are dissolved respectively in proper solvents as preparation of solutions respectively corresponding to the components and the thus obtained solutions are mixed with each other.

As the organic solvent used in this case, a known organic solvent used as polyimide resin solvents can be used. Specific examples thereof include organic solvents such as aromatic hydrocarbon, ketones, esters, ethers (circular ethers, glycol ethers, and the like), N-substituted amides, alcohols, carboxylic acids, amines, chlorine solvent, and the like. Note that, the organic solvent is removed in subsequent steps, so that it is advantageous in the production steps to select a solvent which dissolves components included in the photosensitive resin composition and whose boiling point is as low as possible. Particularly, it is possible to favorably use an organic solvent whose boiling point is 170° C. or lower, preferably 160° C. or lower.

Specific examples of the organic solvent having the foregoing boiling point include: circular ether such as tetrahydrofuran, dioxolane, and dioxane; ethers such as ethyleneglycol dimethylether, triglime, diethylglycol, ethyl cellosolve, methyl cellosolve, diethylether, and chain ether such as various propyleneglycolethers; alcohols such as methanol, ethanol, isopropyl alcohol, and butanol; ketones such as acetone, methylethylketone, and methylisobutylketone; cycloalkanes such as cyclopentanone and cyclohexanone; esters such as acetic ether; and the like. Further, it is possible to favorably use a mixture solvent obtained by mixing toluene, xylenes, glycols, N,N-dimethyl formamide, N,N-dimethyl acetamide, N-methyl pyrrolidone, circular siloxane, chain siloxane, and the like with the ethers. These organic solvents may be independently used, or a suitable combination of two or more kinds may be used.

<Usage of Photosensitive Resin Composition>

The usage of the photosensitive resin composition according to the present invention is not particularly limited. However, examples thereof include a photosensitive resin film or a photosensitive resin sheet and a resin chemical product each of which is made of the photosensitive resin composition.

The photosensitive resin film is obtained by forming the photosensitive resin composition into a film shape. It is possible to use the photosensitive resin film, for example, as a pattern circuit resist film used in formation of a pattern circuit, a photosensitive cover lay film used in formation of an insulative protection film, a photosensitive dry film resist used in formation of an interlayer insulation layer, or for other various purposes, but the usage thereof is not limited to them. Further, the photosensitive resin film is arranged so as to correspond to usage thereof.

Note that, in the present invention, the photosensitive resin films used as the photosensitive cover lay film and the photosensitive dry film resist are generically referred to as a photosentive dry film resist.

Further, an example of the usage of the present invention is a laminate which includes at least one resin layer made of (i) the photosensitive resin composition or (ii) a photosensitive resin film or a photosensitive resin chemical product using the photosensitive resin composition. The laminate can be favorably used, for example, as a circuit substrate or a multi-layered print wiring board.

The photosensitive resin composition according to the present invention can be used as a resin chemical product in the aforementioned solution state. Other various kinds of solvents and additives may be added thereto as required, and the resultant may be used as the resin chemical product. The resin chemical product including the photosensitive resin composition according to the present invention can be used as a coating agent or varnish. The resin chemical product can be impregnated into various fibers such as a glass cloth, a glass mat, an aromatic polyamide fiber cloth, and an aromatic polyamide fiber mat for example. When the photosensitive resin composition impregnated into the fiber is half-cured, it is possible to obtain a fiber reinforced resin sheet.

Further, when the photosensitive resin composition according to the present invention is formed in a sheet shape in advance, it is possible to use the photosensitive resin composition as the photosensitive resin film or the photosensitive resin sheet. Specific examples thereof include (1) a single-layer sheet made only of the photosensitive resin composition, (2) a two-layer or three-layer sheet obtained by providing a resin layer made of the photosensitive resin composition on one side or each side of a film used as a base material (film base material), and (3) a laminate such as a multi-layered sheet or the like in which film base materials and resin layers made of the photosensitive resin composition are alternately stacked.

Next, the photosensitive resin film is specifically described as follows by taking the photosensitive dry film resist as an example, and an example of a print wiring board produced by using the photosensitive dry film resist is specifically described as follows. However, the present invention is not limited to this.

<Photosensitive Dry Film Resist>

The photosensitive dry film resist is produced by evenly applying and drying the organic solvent solution of the photosensitive resin composition on a support film. After evenly applying and drying the organic solvent solution of the photosensitive resin composition on the support film, the resultant is heated or is blasted by hot air. On this account, the organic solvent is removed, so that it is possible to obtain the photosensitive dry film resist which is a film-shaped photosensitive resin composition. The photosensitive dry film resist formed in this manner is a half-cured photosensitive resin composition (in a B stage state). Therefore, in case of carrying out thermocompression bonding such as thermal lamination, the photosensitive dry film resist can exhibit proper fluidity. On this account, it is possible to favorably mount the pattern circuit of the print wiring board. Further, after mounting the pattern circuit, an exposure process, a thermocompression bonding process, and heating cure are carried out, thereby completely curing the mounted pattern circuit.

A drying temperature at which the organic solvent solution of the photosensitive resin composition is dried by heating and/or blasting with hot air is set so that curing groups such as a (meth)acryl group and an epoxy group included in the photosensitive resin composition react with each other. Specifically, the drying temperature is preferably 120° C. or lower, particularly preferably 100° C. or lower. Further, it is preferable to set a drying time to be shorter as long as the organic solvent can be removed within the drying time.

A material for the support film is not particularly limited, but it is possible to use various kinds of ordinarily available films such as a polyethylene terephthalate (PET) film, a polyphenylene sulfide film, and a polyimide film. Among the foregoing support films, the PET film is widely used since the PET film has proper heat resistance and can be obtained at relatively low cost. Note that, in a junction between the support film and the photosensitive dry film resist, it is possible to carry out surface treatment in order to improve the adhesiveness and fissility.

Further, thickness of the support film is not particularly limited, but preferably ranges from 5 μm to 50 μm, more preferably from 10 μm to 30 μm. When the thickness of the support film is less than 5 μm, the support film wrinkles, so that the operability is likely to drop. Therefore, the support film with the thickness of less than 5 μm is not preferable. Further, when the thickness of the support film exceeds 50 μm, it is difficult to wind the photosensitive dry film resist. Therefore, the support film with the thickness exceeding 50 μm is not preferable.

Further, it is preferable to laminate a protective film on the photosensitive dry film resist produced by applying the organic solvent solution of the photosensitive resin composition on the support film. The protective film is laminated, so that it is possible to prevent foreign substances and dusts in the air from adhering thereto and it is possible to prevent the quality of the photosensitive dry film resist from being dropped by the drying.

It is preferable to laminate the protective film on the surface of the photosensitive dry film resist at a temperature ranging from 10° C. to 50° C. Note that, when the temperature at which the lamination is carried out exceeds 50° C., the protective film thermally expands, so that the laminated protective film may be wrinkled and curled.

The protective film is exfoliated in using the photosensitive dry film resist, so that a junction between the protective film and the dry film resist preferably has proper adhesiveness at the time of storage and excellent fissility.

A material for the protective film is not particularly limited, but examples thereof include a polyethylene film (PE film), a polyethylenevinylalcohol film (EVA film), a "film made of copolymer of polyethylene and ethylenevinylalcohol (hereinafter, referred to as a (PE+EVA) copolymer film)", a "body obtained by combining the PE film to the (PE+EVA) copolymer film", or a "film obtained by simultaneously extruding the (PE+EVA) copolymer and polyethylene (a film in which one side is a PE film side and the other side is a (PE+EVA) copolymer film side)".

The PE film can be obtained at low cost and is superior in a surface smoothness. Further, the (PE+EVA) copolymer film has proper adhesiveness and fissility with respect to the photosensitive dry film resist. By using the protective film, it is possible to improve the smoothness when a three-layer sheet including three layers of a protection layer, a photosensitive dry film resist (layer of photosensitive resin composition), and a support film is winded into a roll shape.

<Print Wiring Board>

Next, the print wiring board produced by using the photosensitive dry film resist is described as follows. The photosensitive dry film resist is used to form an interlayer insulation layer of the print wiring board.

The following describes a technique for producing the print wiring board by forming the photosensitive dry film resist according to the present invention as an interlayer insulation layer. As to the print wiring board, a copper foil in which a pattern circuit is formed (hereinafter, this copper foil is referred to as a CCL having a circuit) is explained as an example. However, also in case of forming a multi-layered print wiring board, it is possible to form the interlayer insulation layer in the same manner.

First, the protective film is exfoliated from the three-layer sheet having the protective film, the photosensitive dry film resist, and the support film. In the following description, the two-layer sheet from which the protective film has been exfoliated is referred to as a "photosensitive dry film resist having a support film". Further, the flexible copper plate having a circuit is covered by the photosensitive dry film resist having a support film, and the photosensitive dry film resist and the flexible copper plate are combined with each other by thermal compression so as to be positioned opposite to each other. As the thermal compression, a thermal press process, a lamination process (thermal lamination process), a thermal roll lamination process, or the like are carried out, and the thermal compression is not particularly limited.

In case of combining the photosensitive dry film resist to the flexible copper plate by means of the thermal lamination process or the thermal roll lamination process (hereinafter, both the processes are referred to merely as a lamination process), a process temperature is not less than a lower limit temperature at which the lamination process can be carried out (hereinafter, the lower limit temperature is referred to as a thermal pressure executable temperature). Specifically, the process temperature preferably ranges from 50° C. to 150° C., more preferably from 60° C. to 120° C., still more preferably from 80° C. to 120° C.

When the process temperature exceeds 150° C., cross-linking reaction of photosensitive reaction groups contained in the photosensitive dry film resist occurs at the time of the lamination process, so that the photosensitive dry film resist is progressively cured. Thus, it is not preferable that the process temperature exceeds 150° C. While, when the process temperature is less than 50° C., the fluidity of the photosensitive dry film resist is low, so that it is difficult to mount the pattern circuit. Further, the adhesiveness between the photosensitive dry film resist and a copper circuit or a base film of the CCL having a circuit may drop.

Due to the thermal compression, the photosensitive dry film resist is laminated on the CCL having a circuit, and the support film is laminated, thereby obtaining a sample. Next, the pattern exposure and the development are carried out with respect to the laminate sample. In carrying out the pattern exposure and the development, a photomask pattern is disposed on the support film of the laminate sample, and an exposure process is carried out through the photomask. Thereafter, the support film is exfoliated and the development process is carried out, thereby forming a hole (via) corresponding to the photomask pattern.

Note that, in the foregoing example, the support film is exfoliated after the exposure process, but the exfoliation may be carried out after combining the photosensitive dry film resist having a support film onto the CC1 having a circuit, that is, the exfoliation may be carried out before the exposure process. However, in order to protect the photosensitive dry film resist, it is preferable to carry out the exfoliation after the exposure process has been completed.

As a light source used in the exposure, it is preferable to use a light source which effectively emits light whose wavelength ranges from 300 to 430 nm. This is because the photoreaction initiator contained in the photosensitive dry film resist generally functions by absorbing light whose wavelength is 450 nm or less.

Further, as the developer used in the development process, a basic solution in which a basic compound has been dissolved is used. As a solvent which dissolves the basic compound, any solvent may be used as long as the solvent can dissolve the basic compound. In terms of an environmental problem, it is preferable to use water.

Examples of the basic compound include: hydroxide or carbonate of alkaline metal or alkaline earth metal such as sodium hydroxide, potassium hydroxide, sodium carbonate, and sodium hydrogen carbonate; organic amine compound such as tetramethylammoniumhydroxide; and the like. Specifically, it is possible to use compounds exemplified in <Developer> of Embodiment 1. As the basic compound, one kind may be used, or two or more kinds of compounds may be used.

A concentration of the basic compound contained in the basic solution preferably ranges from 0.1 to 10 wt %. In terms of an anti-alkali property of the photosensitive dry film resist, the concentration more preferably ranges from 0.1 to 5 wt %.

Note that, the development process is not particularly limited. However, for example, it is possible to adopt: a method in which a developing sample is placed into basic solution and the basic solution is stirred; a method in which the developer is sprayed to the developing sample; and a similar method.

In the present invention, particularly, it is preferable to use 1 wt % of sodium hydroxide whose temperature has been adjusted to 40° C. as the developer so as to carry out the development with a spray developing device. The spray developing device is not particularly limited as long as the device sprays the developer to the sample.

Further, time taken to form a predetermined pattern on the photosensitive dry film resist is not particularly limited, but the developing time is preferably 180 seconds or less, more preferably 90 seconds or less, most preferably 60 seconds or less. It is not preferable that the developing time exceeds 180 seconds in terms of the productivity.

Here, as a standard of the developing time, time taken to dissolve the photosensitive dry film resist in the B stage (half-cured) state is measured. Specifically, an unexposed sample obtained by combining the photosensitive dry film resist to a lustrous surface of the copper foil is subjected to the spraying development by using sodium hydroxide aqueous solution whose concentration is 1% (liquid temperature is 40° C.) as the developer at a spray pressure of 0.85MPa. It is preferable that the spraying development causes the photosensitive dry film resist to be dissolved and removed in 180 seconds or less. When the time taken to dissolve and remove the photosensitive dry film resist exceeds 180 seconds, the workability drops.

As described above, after carrying out the exposure and developing processes, the heating cure is carried out with respect to the photosensitive dry film resist. On this account, it is possible to completely cure the photosensitive dry film resist. As a result, the thus cured photosensitive dry film resist serves as an insulative protection film of the print wiring board.

Further, in case of forming a multi-layer print wiring board, a protective layer of the print wiring is used as an interlayer insulation layer, and sputtering or dipping is carried out with respect to the interlayer insulation layer or a copper foil is combined to the interlayer insulation layer, and then a pattern circuit is formed thereon, so as to laminate the photosensitive dry film resist as described above. On this account, it is possible to produce the multi-layer print wiring board.

Note that, the present embodiment described the case where the photosensitive dry film resist is used as the insulative protection material or the interlayer insulation material of the print wiring board, but it is possible to use the photosensitive dry film resist for other purposes.

Embodiment 3

A photosensitive resin composition according to the present embodiment is a composition containing a soluble polyimide resin (K) having a carboxylic group and/or a hydroxyl group, a specific phenoxyphosphazene compound (L), and (meth)acrylic compounds (M). The photosensitive resin composition according to the present embodiment may further contain an other component (N), if necessary. For example, the photosensitive resin composition according to the present embodiment may further contain a compound, which gives a property such as adhesiveness, flame retardancy, heat resistance, anti-bending, and/or the like to a resultant photosensitive dry film resist. A photosensitive dry film resist according to the present embodiment is prepared from the photosensitive resin composition according to the present embodiment. In the following, each component is described.

<Soluble Polyimide Resin (K) having Carboxylic Group and/or Hydroxyl Group>

The photosensitive resin composition according to the present embodiment contains the soluble polyimide resin having a carboxyl group and/or a hydroxyl group. With this, the resultant photosensitive dry film resist attains heat resistance, anti-bending property, excellent mechanical property, electric insulation property, and anti-chemical property. Further, the presence of the carboxylic group and/or hydroxyl group (preferably phenolic hydroxyl group) makes it possible to develop water system.

The soluble polyimide resin (K) may be the soluble polyimide resin (G-1) described in Embodiment 2. That is, it is preferable that the soluble polyimide resin (K) have a carbon-carbon double bond, for example, in a side chain thereof. Moreover, the soluble polyimide resin (K) may be similar to the soluble polyimide resin (G-1) in terms of solubility with respect to an organic solvent, weight-average molecular weight, acidic equivalent, and the like. The organic solvent used in Embodiment 2 may be adopted in the present embodiment.

<Production Method of the Soluble Polyimide Resin (K)>

For explaining a production method of the soluble polyimide resin having a carboxylic group and/or a hydroxyl group, a synthesis method of a polyamide acid, and a method for imidizing the polyamide acid by dehydration ring closure are described below.

<Synthesis Method of Polyamide Acid>

The synthesis methods described in Embodiments 1 and 2 may be adopted here. That is, the soluble polyimide resin (K) may be prepared from a polyamide acid, which is a precursor thereof. The polyamide acid may be prepared by reacting a diamine with an acid dianhydride in an organic solvent. More specifically, a diamine solution is prepared by dissolving the diamine in the organic solvent under inert atmosphere using argon, nitrogen, or the like, or by prepare a slurry of the diamine by diffusing the diamine in the organic solvent under inert atmosphere using argon, nitrogen, or the like. The acid dianhydride may be added into the diamine solution by adding (i) a solution in which the acid dianhydride is dissolved in the organic solvent, (ii) a slurry of the acid dianhydride diffused in the organic solvent, or (iii) the acid dianhydride in a solid form. The compound and the acid dianhydride may be the diamine and the acid anhydride used in the production of the soluble polyimide (G-1) in Embodiment 2.

In the present embodiment, temperature condition of the reaction of the diamine with the acid dianhydride (i.e., the synthesis reaction of the polyamide acid) is not particularly limited, but is preferably 80° C. or less, and more preferably in a range of 0° C. to 50° C. At a temperature above 80° C., there is a risk of causing decomposition of the polyamide acid. On the other hand, polymerization reaction may be slow at a temperature of 0° C. or below. Moreover, reaction time may be set arbitrarily within a range of 10 minutes to 30 hours.

Further, the organic solvent for use in the synthesis reaction of the polyamide acid is not particularly limited as long as the solvent is an organic polar solvent. Examples of the organic solvent include: the organic solvents listed in Embodiment 2; ethers solvents such as tetrahydrofuran, dioxane, dioxolane, and the like; and the like organic solvent.

<Imidization of Polyamide Acid>

Imidization of the polyamide acid may be carried out by the same method as in Embodiment 2. Moreover, the imidization may be attained by dehydration ring closure of the polyamide acid carried out by thermally dehydrating the polyamide acid under reduced pressure in a container which has been subjected to mold-releasing treatment such as coating with fluorine resin.

<Polyimide having at Least One Kind of Carbon-carbon Double Bond, which is Selected from an Acryl Group, a Methacryl Group, a Vinyl Group, and an Allyl Group>

Next, the thus obtained soluble polyimide resin (K) is denaturalized thereby to introduce therein a photosensitive group such as an acryl group, a methacryl group, a vinyl group, an allyl group, and/or the like.

It is preferable that the soluble polyimide according to the present embodiment having the carboxyl group and/or hydroxyl group be the double-bond polyimide resin. More specifically, it is more preferable that the soluble polyimide have, for example, in its side chain, at least one kind of carbon-carbon double bond, which is selected from an acryl group, a methacryl group, a vinyl group, and an allyl group, even though the soluble polyimide may have a functional group having a carbon-carbon double bond except the functional groups mentioned above.

The double-bond polyimide resin according to the present embodiment may be obtained by denaturalizing the soluble polyimide resin having the carboxyl group and/or hydroxyl group by reacting it with a compound having a carbon-carbon double bond. The denaturalizing may be carried out in the same manner as in Embodiment 2 in terms of the compound to be reacted with the soluble polyimide resin, a solvent for use in the reaction, reaction conditions, and the like.

<Phenoxyphosphazene Compound (L)>

Next, the phenoxyphosphazene compound (L) is explained. The phenoxyphosphazene compound (L) according to the present embodiment comprises at least one of a circular phenoxyphosphazene compound (L-1) and a chain phenoxyphosphazene compound (L-2), and further comprises a cross-linked phenoxyphosphazene compound (L-3) which has a cross-linked structure in which a cross-linking agent is introduced between oxygen atoms obtained by desorbing phenyl groups, the circular phenoxyphosphazene compound (L-1) being represented by formula (22)

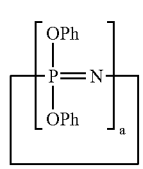

where a represents an integer ranging from 3 to 30, the chain phenoxyphosphazene compound (L-2) being represented by formula (23)

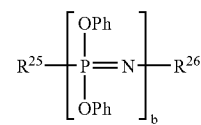

where $R^{25}$ represents group —N=(OPh)$_3$ or group —N=P(O)OPh, $R^{26}$ is group-P(OPh)4 or group-P(O)(OPh)$_2$, and b represents an integer ranging from 3 to 10000), and the cross-linking agent containing any one of o-phenylene group, m-phenylene group, p-phenylene, group, or bisphenylene group represented by the following formula (3)

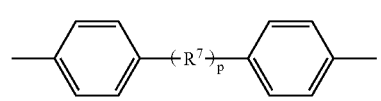

where $R^7$ represents —C(CH$_3$)$_2$—, —SO$_2$—, —S—, or —O—, and p is 0 or 1). Furthermore, a phenyl-group containing ratio of the cross-linked phenoxyphosphazene compound (L-3) is preferably in a range of 50% to 99.9% with respect to a total of phenyl groups present in the phosphazene compound including at least one of the circular phenoxyphosphazene compound (L-1) and the chain phenoxyphosphazene compound (L-2). The phenyl-group containing ratio can be obtained from an elemental analysis value.

Compared with the conventional phosphorus compounds, the phenoxyphosphazene compound (L) is excellent in anti-hydrolysis property. Moreover, compared with propoxylated phosphazene compounds, the phenoxyphosphazene compound (L) is excellent in heat resistance and can give flame retardancy to the resultant photosensitive dry film resist without deteriorating its property such as adhesiveness and the like. Especially, the use of the cross-linked phenoxyphosphazene compound is more preferable. This is because the cross-linked phenoxyphosphazene compound (L-3) has an excellent phase solubility with respect to polyimide resins, so that it makes bleeding hard to occur, and further the cross-linked phenoxyphosphazene compound (L-3) has low volatility, which can inhibit dropping and the like when flamed. The cross-linked phenoxyphosphazene compound (L-3) is not particularly limited. Examples of the cross-linked phenoxyphosphazene compound (L-3) include SPB-100, SPE-100, SPS-100, and SPB-156 (made by Otsuka Chemicals Inc.). The phenoxyphosphazene compound (L) may contain a phenoxyphosphazene compound other than the cross-linked phenoxyphosphazene compound (L-3), in addition to the cross-linked phenoxyphosphazene compound (L-3). The other phenoxyphosphazene compound may be the circular phenoxyphosphazene compound (L-1), the chain phenoxyphosphazene compound (L-2), and the like. The phenoxyphosphazene compound (L) is preferably used in an amount in a range of 1 to 100 parts by weight, more preferably in a range of 1 to 50 parts by weight, and especially preferably in a range of 1 to 40 parts by weight, where the total of the soluble polyimide resin (K) and the later described (meth) acrylic compounds (M) is 100 parts by weight.

There is a possibility that the flame retardancy becomes insufficient when the amount of the phenoxyphosphazene compound (L) is less than 1 part by weight where the total of the soluble polyimide resin (K) and the later described (meth) acrylic compounds (M) is 100 parts by weight. On the other hand, if the amount of the phenoxyphosphazene compound (L) exceeded 100 parts by weight, the photosensitive dry film resist would possibly becomes sticky in the B stage-state, the bleeding would be easy to occur during the thermo-pressing, and further, the cured product would possibly have poor properties. Therefore, the amount of the phenoxyphosphazene compound (L) exceeded 100 parts by weight is not preferable.

<(Meth)acrylic Compound (M)>

Next, the (meth)acrylic compounds (M) are described. The photosensitive composition comprising the (meth)acrylic compounds (M) can have good curing property. Further the photosensitive dry film resist produced therefrom can be less viscoelastic during thermal process and excellently flowable during thermal lamination process. That is, the photosensitive composition comprising the (meth)acrylic compounds (M) makes it possible to perform thermal lamination process at a relatively low temperature. This allows the composition to be used to bury an irregular surface of a circuit.

The (meth)acrylic compounds (M) according to the present embodiment may be the (meth)acrylic compounds (I) used in Embodiment 2. Further, the conditions such as an amount of the (meth)acrylic compounds (M) to be mixed are preferably similar to those in Embodiment 2.

<Other Component (N)>

The photosensitive resin composition according to the present invention may comprise the other component (N) if necessary, in addition to the soluble polyimide resin (K), phenoxyphosphazene compound (L), and (meth)acrylic compounds (M). The other component (N) may be, for example, an epoxy resin, curing promotion agent and/or curing agent, a photoreaction initiator and/or sensitizer, or the like.

<Epoxy Resin>

Use of the epoxy resin can give the thus produced photosensitive dry film resist a better adhesiveness with respect to a copper foil, polyimide film or the like.

The epoxy resin is not particularly limited and may be the same as the epoxy resin (J-1) used in Embodiment 2. Further, the conditions such as an amount of the epoxy resin to be mixed are preferably similar to those in Embodiment 2.

<Curing Promotion Agent and/or Curing Agent>

In case where the epoxy resin is used as a material of the photosensitive resin composition, a curing promotion agent and/or curing agent may be added to the photosensitive resin composition, so that the curing of the produced photosensitive dry film resist can be more efficient. There is no particular limitation in the curing promotion agent and/or curing agent. For example, the curing promotion agent and/or curing agent (J-2) used in Embodiment 2 may be adopted here. Further, the conditions such as an amount of the curing promotion agent and/or curing agent to be mixed are preferably similar to those in Embodiment 2.

<Photoreaction Initiator/Sensitizer>

If a photoreaction initiator and/or sensitizer is added to the photosensitive dry film resist, cross-linking reaction and/or polymerization reaction may be promoted in that portion of the photosensitive dry film resist which is exposed to light. With this, the exposed and unexposed portions of the photosensitive dry film resist can be sufficiently different from each other in terms of solubility with respect to an aqueous developer. As a result, it becomes possible to suitably develop a pattern on the photosensitive dry film resist.

The photoreaction initiator and/or sensitizer (J-3) used in Embodiment 2 may be adopted as the photoreaction initiator and/or sensitizer. Further, the conditions such as an amount of the photoreaction initiator and/or sensitizer to be mixed are preferably similar to those in Embodiment 2.

<Preparation Method of the Photosensitive Resin Composition and Production Method of the Photosensitive Dry Film Resist>

In the following, the preparation method of the photosensitive resin composition and production method of the photosensitive dry film resist are described. To produce the photosensitive dry film resist, an organic solvent solution of the photosensitive resin composition is evenly applied and dried on a support film.

<Preparation Method of Photosensitive Resin Composition>

The preparation method of the photosensitive resin composition according to the present invention is explained below. The photosensitive resin composition according to the present invention is a mixture of the soluble polyimide (A), phenoxyphosphazene compound (L), (meth)acrylic compounds (C), and if necessary the other component (D), which are mixed in a given mixing ratio. The organic solvent solution of the photosensitive resin composition is a solution in which the photosensitive resin composition is dissolved in an organic solvent. The organic solvent is not particularly limited as long as it can dissolve the components in the photosensitive resin composition. Examples of the organic solvent include: ethers solvents such as dioxolane, dioxane, tetrahydrofuran, and the like; ketones solvents such as acetone, methylethylketones, and the like; alcohols solvents such as methanol, ethanol, and the like; and the like organic solvents. The organic solvents may be used solely, or two or more of them may be used in combination. Because the organic solvent is removed in a later stage in the manufacturing process, it is preferable for the sake of the manufacturing process to choose an organic solvent which can dissolve the components in the photosensitive resin composition and which has a boiling point as low as possible.

<Production Method of the Photosensitive Dry Film Resist>

After that, the organic solvent solution of the photosensitive resin composition is applied evenly on the support film, and then thermally treated and/or blown with hot air. With this, the organic solvent is removed and the photosensitive resin composition attains a film-like form thereby forming the photosensitive dry film resist. The thus prepared photosensitive dry film resist, the photosensitive composition is still in half-cured state (at the B stage) Therefore, the photosensitive dry film resist can be appropriately flowable in the thermal compression process such as the thermal lamination process and the like, and thus suitable for burying the pattern circuit of the print wiring board. Further, curing of the photosensitive dry film resist can be completed by exposure process, thermal compression process, or thermal curing, after burying the pattern circuit therewith.

The production method of the photosensitive dry film resist may be similar to those in Embodiment 2. Moreover, the present embodiment is preferably similar to Embodiment 2 in terms of a material and thickness of the supporting film, a material of a protective film, lamination conditions of the films, and the like conditions.

<Production of the Print Wiring Board>

Next, the print wiring board produced by using the photosensitive dry film resist is described below. The photosensitive dry film resist is, for example, used to form an interlayer insulation film of the print wiring board. For example, production of the print wiring board according to the present embodiment may be carried out in a manner similar to that of Embodiment 2. That is, if a CCL on which a circuit is mounted is used, it is possible to produce the print wiring board by thermo compression and exposure/development process. In this case, the thermo compression and exposure/development process is preferably carried out in a manner similar to that of Embodiment 2.

Note that, the photosensitive dry film resist according to the present embodiment is applicable to usages other than using it as the insulative protection material or interlayer insulation material of the print wiring board, even though the use of the photosensitive resin as the insulative protection material or interlayer insulation material is exemplified here again.

EXAMPLES

The present invention is described below referring to Examples and Comparative Examples, which are not to limit the present invention. For a person skilled in the art, it is possible to make various changes, modification, and alternation within the scope of the present invention. In Examples 10 to 26 and Comparative Examples 1 and 2, various properties of photosensitive resin compositions are measured and evaluated in the following manners.

[Flame Retardancy]

Flame retardancy test was carried out in the following manner according to retardancy test standard UL94 for plastic materials. A solution of a photosensitive resin composition was applied on a polyimide film (made by Kaneka Corp.: 25AH film) of 25 μm thickness by using a bar coater while shielding the photosensitive resin composition from light. Then, the photosensitive resin composition was dried at 60° C. for 5 minutes, and at 90° C. for 5 minutes, whereby the thus applied photosensitive resin composition attained a thickness of 25 μm after drying. After that, the photosensitive resin composition is exposed to light of 400 nm with a dose of only 600 mJ/cm$^2$ and then thermally cured for 2 hours in an oven that was set at 180° C.

A sample prepared in this way was cut thereby to prepare 20 samples of 1.27 cm width×12.7 cm length×50 μm thickness (including the thickness of the polyimide film).

Ten out of 20 samples were treated with a temperature of 23° C. under 50% relative humidity for 48 hours (condition (1)), and the remaining ten samples were treated with a temperature of 70° C. for 168 hours (condition (2)) and then cooled for 4 hours in a desiccator with anhydrous calcium chloride.

Then, these samples were held vertically by clumping upper parts thereof and fired by holding flame of a burner close to lower parts thereof for 10 seconds. Ten seconds later the flame of the burner was moved away from the samples, Then, how long the flaming or burning of the samples took to be extinguished was measured. The sample was regarded as being proper if the samples of both the conditions ((1) and (2)) stopped burning or flaming and were self-extinguished within 5 seconds on average (average of 10 samples) from the time the flame of the burner was moved away from the samples, and none of them stopped burning or flaming and were self-extinguished beyond 10 seconds from the time the flame of the burner was moved away from the samples.

[Development]

A solution of a photosensitive resin composition was applied on an electrolysis copper foil (produced by MITSUI MINING & SMELTING Co., LTD.: NDP-3 ½ oz) of 25 μm thickness by using a bar coater. Then, the photosensitive resin composition was dried at 60° C. for 5 minutes, and then at 90° C. for 5 minutes, whereby the thus applied photosensitive resin composition attained a thickness of 25 μm after drying. In this way a lamination made from the photosensitive resin composition was prepared. After placing a mask pattern thereon, the photosensitive resin composition was exposed to light of wavelength 400 nm with a dose of only 300 mJ/cm$^2$. The photosensitive resin composition was developed by subjecting to an aqueous solution of potassium hydroxide of 1 wt % (liquid temperature 40° C.) for 1 minute, the aqueous solution having been sprayed thereon using a spray developer at a spray pressure 0.85 MPa. The photo mask pattern had a fine square hole of 100×100 μm. The pattern thus formed by the development was then washed with distilled water to remove the developer and dried. If the development of the fine square hole of 100×100 μm was successful, the sample was regarded as being proper.

[Soldering Heat Resistance]

An electrolysis copper foil (produced by MITSUI MINING & SMELTING Co., LTD.: NDP-3 ½ oz) was subjected to soft etching with an aqueous solution of sulfuric acid of 10 wt % (soft etching is a step for removing anti-lusting agent from a surface of the copper foil). After washed with water, the surface of the copper foil was washed with ethanol and acetone, and then dried. A solution of a photosensitive resin composition was applied on the electrolysis copper foil by using a bar coater, and then dried at 60° C. for 5 minutes, and further at 90° C. for 5 minutes, whereby the thus applied photosensitive resin composition attained a thickness of 25 μm after drying. After that, the thus laminated photosensitive resin composition was exposed to light of 400 nm wavelength with a dose of only 300 mJ/cm$^2$. Then, thus prepared sample was cut into 4 cm square, and cured at 180° C. for 2 hours. The sample was conditioned under normal condition (1) (20° C./relative humidity of 40%/24hours) or under humid condition (2) (40° C./relative humidity of 85%/48 hours). After that, the sample was dipped in a melted solder at a temperature of 270° C. or higher. It was observed as to whether or not swelling occurred in an interface between the copper foil and the coverlay and whether or not the coverlay was exfoliated from the copper foil. By dipping the sample in the melted solder for 30 seconds every 10° C. temperature elevation while gradually increasing the temperature of the melted solder, it was also observed until which temperature the sample had no such abnormality. A highest temperature at which no such abnormality occurred was put as 30-second-dipable temperature.

[Anti Migration]

Only one side of a flexible copper laminate plate produced by Nippon Steel Chemical Co., Ltd. (double-side copper lamination board formed by placing copper foil layers on a polyimide resin) SC18-25-00 WE was subjected to etching thereby removing the copper foil from the one side. In this way, a single-side flexible copper laminate plate was prepared. On the single-side flexible copper laminate plate an interleave pattern as illustrated in FIG. 1 was formed. Lines/spaces of the interleave pattern were 40 μm and 40 μm. On the interleave pattern, a photosensitive film from which a protection film had been exfoliated was placed and laminated applying a temperature of 100° C. and a pressure of 20000 Pa·m. Then, the lamination was exposed to light of 400 nm with a dose of only 1800m J/cm$^2$. After that, a cover film was laminated thereon by heating at 180° C. for 2 hours.

In an environmental testing machine adjusted to 85° C. and 85%RH, a DC voltage of 100V was applied across the interleave pattern covered with the photosensitive film. Variation of resistance and whether or not migration occurred were observed for 1000 hours. An insulation resistance after 1000 hours and whether or not migration occurred in 1000 hours were evaluated as test results. As to the insulation resistance, it was regarded as being proper if the insulation resistance was at least 10$^6$ Ω after 1000 hours.

[Adhesiveness]

The adhesiveness was measured in accordance with JIS-D-0202.

[Insulation Resistance]

The insulation resistance was measured in accordance with JIS-C-6481.

[Material to Use]

The following commercially available products were used as materials glycidyl methacrylate (produced by Wako Pure Chemical Industries, Ltd.), NK-oligo EA-1010 (SHIN-NA-KAMURA CHEMICAL CO., LTD.), triethyl amine (Wako Pure Chemical Industries, Ltd.), tetrahydrofuran (Wako Pure Chemical Industries, Ltd.), and hexane (Wako Pure Chemical Industries, Ltd.). NK-oligo EA-10101 has a structure represented by the following formula (18):

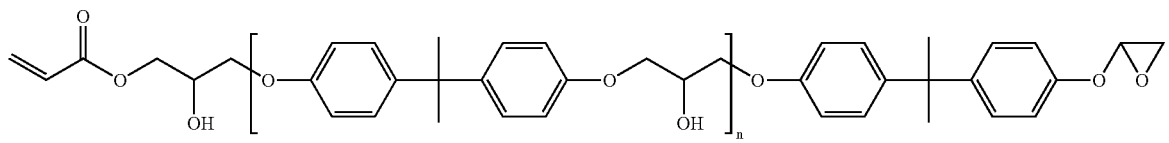

(18)

An average molecular weight of NK-oligo EA-10101 is 448.

Further, NMR (Nuclear Magnetic Resonance Spectrum) used was Gemini made by Varian. The measurement was carried out at 25° C.

Synthesis Example 1

Synthesis of Raw Material Phosphazene Compound

Into a 5 L-flask provided with a reflex condenser, thermometer, stirring device, a dropping device for dropping phosphorus trichloride, and a tube for introducing chloride gas, 2.5 L of chlorobenzen, 182.5 g (3.4 mol) of ammonium chloride, and 2.5 g of zinc chloride were introduced, thereby to obtain a mixture dispersion liquid. The dispersion liquid was heated to a temperature of 130° C. Under reflux, 425.5 g was dropped therein for 48 minutes at a rate of 9 g/min, and concurrently 227 g of chloride gas was supplied therein for 46 hours at a rate of 5 g/min. After the supply of phosphorous trichloride and chloride gas, the reflux was further continued for 150 minutes (at 131° C.). Then, the reaction was completed. Next, suction filtration was carried out to remove unreacted ammonium chloride. The filtrate was distilled under reduced pressure of 1.0 to 3.0 hPa at a temperature of 30° C. to 50° C., thereby distilling off chlorobenzene. In this way, a reaction product of 352 g was obtained. Yield of the reaction product was 98.1% with respect to phosphorus trichloride, which was the reaction product.

The thus prepared reaction product was dissolved into chlorobenzene again and recrystallized, thereby obtaining a mixture of hexachlorocyclotriphosphazene and octachlorocyclotetraphosphazene (226 g: hexachlorocyclotriphosphazene: 76%, octachlorocyclotetraphosphazene: 24%).

The chlorobenzene solution left over after the re crystallization was concentrated thereby obtaining 125 g of circular phosphazene compound and chain phosphazene compound (a mixture of the phosphazene compounds represented by the general formulae (4) and (5) where m and n are in a range of 3 to 15). Further, the mixture of hexachlorocyclotriphosphazene and octachlorocyclotetraphosphazene was subjected to recrystallization process with hexane three times, thereby obtaining 155 g of hexachlorocyclotriphosphazene of 99.9% purity.

Synthesis Example 2

Synthesis of Phenoxyphosphazene Compound (A-1)

In a 2 L four-necked flask provided with a reflux condenser, thermometer, stirring device, and dropping funnel, 58 g of hexachlorocyclotriphosphazene (0.5 unit mol, where NPC 12 is one unit), and 100 ml of tetrahydrofuran (THF) were introduced, thereby preparing a solution.

A THF solution of sodium salt of 4-methoxyphenol (149.0 g (1.2 mol) of 4-methoxyphenol, 25.3 g (1.1 g-atom) of sodium and 600 ml of THF) was prepared separately, and dropped into the thus prepared solution of hexachlorocyclotriphosphazene. The dropping was carried out to take two hours. The drop reaction was carried out with cooling because the reaction was highly exothermic until approximately ⅓ amount of the sodium salt was added. When the remaining ⅔ amount of the sodium salt was added, the reaction was not highly exothermic. However, the drop reaction was carried out with cooling to control reaction temperature at or below 30° C.

After the dropping, the reaction was continued with stirring at a room temperature for 12 hours. Next, to terminate the reaction, the reaction was carried out for 6 hours refluxing the solvent. After the reaction, THF used as the solvent was distilled off under a reduced pressure. Then, the resultant was redissolved in 500 ml of toluene added thereto. After 500 ml of water was added thereto, an organic layer was separated from the solution of the resultant and 500 ml toluene using a separating funnel. The organic layer was washed three times with an aqueous solution of sodium hydroxide of 5 wt %, once with 500 ml of an aqueous solution of (1+9) hydrochloric acid, once with 500 ml of sodium hydrogen carbonate solution of 5 wt %, and twice with 500 ml of water. After washing, pH of a water layer was 7 to 8.

The organic layer was separated, and then dehydrated with magnesium sulfuric anhydride. Then toluene was distilled off from the organic layer, thereby obtaining 138.4 g of hexa(4-methoxyphenoxy)cyclotriphosphazene in a yellowish solid form (yield 95%). Residual chlorine content was 0.02% and melting point was 104° C. (literature value 103° C. to 104° C.).

Then, in a 2-L four-necked flask, and 130.6 g (0.45 unit mol) of Hexa(4-methoxyphenoxy)cyclotriphosphazene thus obtained and 1040 g (9 mol) of pyridine chlorate were gradually heated and reacted with each other at 205-210° C. for one hour. After cooled down to a room temperature, 300 ml of water was added therein to dissolve a reaction product and excess pyridine chlorate. Then, pH of the solution was adjusted to pH 6 to 7 with sodium hydroxide of 20 wt %. In this way, a reaction solution was prepared. Then, the reaction solution was subjected to extraction four times with 500 ml ethyl acetate. Extracts of the four extractions were added together and then washed four times with 500 ml of saturated sodium sulfate solution. Then, an organic layer was separated therefrom. The organic layer was dehydrated with magnesium sulfuric anhydride, and then distilled under reduced pressure to distill off ethyl acetate therefrom. Next, the concentrate was dissolved in 200 ml of methanol. The methanol solution was added into 1.5 L of water. Crystallization was repeated three times. Thus obtained crystal was dried under reduced pressure, thereby obtaining 94.8 g of light-yellowing crystal (yield 80%).

A residual chlorine in the product was 0.01% or less. Hydroxide group content (OH, %) was measured according to acetylation method using acetic anhydride and pyridine (acetylation method is described in Analytical Chemistry Manual (edited by Japan Society for Analytical Chemistry), organic chemistry, p316). The hydroxide group content was 12.9%. (Theoretical value is 12.9%, composition formula $N_3P_3(OC_6H_4OH)_6$, hydroxide group equivalent 131.8) Moreover, 1H- and $^{31}$P-NMR analysis of the product showed that the synthesis was successful.

Synthesis Example 3

Synthesis of Phenoxyphosphazene Compound (A-1)

A 4-methoxyphenoxy derivative was obtained according to the same method as in Synthesis Example 2 except that 58 g (0.5 unit mol) of circular chlorophosphazene and chain chlorophosphazene were used. Yield was 135.7 g (93%). Residual chloride content was 0.04%. A yellowish and highly viscous material was obtained.

Methyl group was removed in the same manner as in Synthesis Example 2, except that 131.1 g (0.45 unit mol) of the thus obtained 4-methoxyphenoxy derivative. This produced a product, which was light brown and highly viscous. Yield was 98.6 g (75%). Residual chloride content in the product was not more than 0.01%. 1H- and 31-NMR analysis of the product showed that the synthesis was successful. Hydroxide group content was 12.7% (hydroxide group equivalent 133.9).

Synthesis Example 4

Synthesis of Phenoxyphosphazene Compound (A-1)

Into a 2 L four-necked flask provided with a reflux condenser, thermometer, stirring device, and dropping funnel, 58 g (0.5 unit mol where NPC 12 is one unit) of hexachlorocyclotriphosphazene of 99.9% purity and 100 ml of THF were introduced, thereby to obtain a THF solution. A THF solution of Na salt of 4-methoxyphenol was separately prepared by adding 68.3 g (0.55 mol) of 4-methoxyphenol, 11.1 g (0.44g-atom) of sodium, and 200 ml of THF). The THF solution of Na salt of 4-methoxyphenol was dropped into the THF solution of hexachlorocyclotriphosphazene with stirring. The dropping was carried out taking one hour to complete. Reaction was carried out with appropriate cooling not to allow reaction temperature to exceed 30° C. because the reaction was highly exothermic. After dropping, the reaction was continued for 6 hours at 60° C. with stirring. A partially substituted product obtained through this reaction had residual chloride content of 15.78% and its structure was deduced as $N_3P_3Cl_{3.36}(OC_6H_4OCH_3)_{2.63}$.

A THF solution of sodium phenolate was separately prepared by adding 61.2 g (0.65 mol) of phenol, 13.8 g (0.6 g-atom) of sodium, and 200 ml of THF. The THF solution of sodium phenolate was dropped therein with cooling not to allow reaction temperature to be more than 30° C. The dropping was carried out to take one hour to complete. Then, the reaction was continued at a room temperature for 5 hours and then at a reflux temperature for 3 hours. Then, the reaction was completed. After the reaction, the THF serving as the solvent was distilled off under reduced pressure. Next, 500 ml of toluene was added to redissolve a product from the reaction. Then, 300 ml of water was further added, and water-wash separation was performed. Thus obtained organic layer was washed once with an aqueous solution of sodium hydroxide of 5 wt %, once with an aqueous solution of sodium hydroxide of 2 wt %, once with an aqueous solution of (1+9) chloride acid twice with water, once with sodium hydrogen carbonate of 5 wt %, and twice with water. Thereby, a water layer became neutral. Next, the organic layer was separated, and dehydrated with magnesium sulfuric anhydride. Then, toluene was distilled off therefrom. This produced 122.6 g (yield 95%) of product, which was light yellow and oily and had residual chloride content not more than 0.01%.

Into a 2 L four-necked flask, 116.2 g (0.45 unit mol) of cyclotriphosphazene in which 4-methoxyphenoxy group and phenoxy group were mixedly substituted, and 583.6 g (5.05 mol) of pyridine chlorate were introduced. They were gradually heated and reacted with each other at 205-210° C. for one hour. Later process was carried out in the same manner as in Synthesis Example 2, thereby obtaining 90.5 g of yellow solid (yield 81.8%). The product had residual chloride content not more than 0.01% and hydroxide content of 6.1% (theoretical value 6.1%, composition formula $N_3P_3(OPh)_{3.36}(OC_6H_4OH)_{2.63}$, and hydroxide group equivalent 279).

Synthesis Example 5

Synthesis of Phenoxyphosphazene Compound (A-1)

Into a 2 L four-necked flask provided with a reflux condenser, thermometer, stirring device, and dropping funnel, 58 g (0.5 unit mol where NPC 12 is one unit) of hexachlorocyclotriphosphazene of 99.9% purity and 100 ml of THF were introduced, thereby to obtain a THF solution.

A THF solution of Na salt of 4-methoxyphenol was separately prepared by adding 37.2 g (0.3 mol) of 4-methoxyphenol, 6.0 g (0.26g-atom) of sodium, and 200 ml of THF). The THF solution of Na salt of 4-methoxyphenol was dropped into the THF solution of hexachlorocyclotriphosphazene with stirring. The dropping was carried out taking one hour to complete. Reaction was carried out with appropriate cooling not to allow reaction temperature to exceed 30° C. because the reaction was highly exothermic. After dropping, the reaction was continued for 6 hours at 60° C. with stirring. A partially substituted product obtained through this reaction had residual chloride content of 35.58% and its structure was deduced as $N_3P_3Cl_{4.45}(OC_6H_4OCH_3)_{1.55}$.

A THF solution of sodium phenolate was separately prepared by adding 79.1 g (0.85 mol) of phenol, 18.4 g (0.8 g-atom) of sodium, and 200 ml of THF. The THF solution of sodium phenolate was dropped the above solution with cooling not to allow reaction temperature to be more than 30° C. The dropping was carried out to take one hour to complete. Then, the reaction was continued at a room temperature for 5 hours and then at a reflux temperature for 3 hours. After that, the reaction was completed. After the reaction, the THF serving as the solvent was distilled off under reduced pressure. Next, 500 ml of toluene was added to redissolve a product from the reaction. Then, 300 ml of water was further added, and water-wash separation was performed. Thus obtained organic layer was washed once with an aqueous solution of sodium hydroxide of 5 wt %, once with an aqueous solution of sodium hydroxide of 2 wt %, once with an aqueous solution of (1+9) chloride acid twice with water, once with sodium hydrogen carbonate of 5 wt %, and twice with water. Thereby, a water layer became neutral. Next, the organic layer was separated, and dehydrated with magnesium sulfuric anhydride. Then, toluene was distilled off. This produced 110.0 g (yield 90%) of product, which was light yellow and oily and had residual chloride content not more than 0.01%.

Into a 2 L four-necked flask, 98.7 g (0.40 unit mol) of cyclotriphosphazene in which 4-methoxyphenoxy group and phenoxy group were mixedly substituted, and 583.6 g (5.05 mol) of pyridine chlorate were introduced. They were gradually heated and reacted with each other at 205-210° C. for one hour. Later process was carried out in the same manner as in Synthesis Example 2, thereby obtaining 75.0 g of yellow solid (yield 78.3%). The product had residual chloride content not more than 0.01% and hydroxide content of 4.0% (theoretical value 4.0%, composition formula $N_3P_3(OPh)_{4.45}(OC_6H_4OH)_{1.55}$, and hydroxide group equivalent 430).

Synthesis Example 6

Synthesis of Cross-linked Phenoxyphosphazene Compound (A-2)

Into a 2 L four-necked flask provided with a reflux condenser, thermometer, stirring device, and dropping funnel, 58 g (0.5 unit mol where NPC 12 is one unit) of hexachlorocyclotriphosphazene of 99.9% purity and 100 ml of THF were introduced, thereby to obtain a THF solution.

A THF solution of Na salt of a phenol was separately prepared by adding 37.2 g (0.3 mol) of 4-methoxyphenol, 11.0 g (0.10 mol) of resorcinol, 12.6 g (0.55 g-atom) of sodium, and 400 ml of THF). The THF solution of Na salt of the phenol was dropped into the THF solution of hexachlorocyclotriphosphazene with stirring. The dropping was carried out taking one hour to complete. Reaction was carried out with appropriate cooling not to allow reaction temperature to exceed 30° C. because the reaction was exothermic. After dropping, the reaction was continued for 6 hours at 60° C. with stirring. A partially substituted product obtained through this reaction had residual chloride content of 21.17% and its structure was deduced as $N_3P_3Cl_{3.15}(OC_6H_4OCH_3)_{1.78}(OC_6H_4O)_{0.50}(OC_6H_4OH)_{0.07})$.

A THF solution of sodium phenolate was separately prepared by adding 79.1 g (0.85 mol) of phenol, 18.4 g (0.8 mol) of sodium, and 200 ml of THF. The THF solution of sodium phenolate was dropped the above solution with cooling not to allow reaction temperature to be more than 30° C. The dropping was carried out to take one hour to complete. Then, the reaction was continued at a room temperature for 5 hours and then at a reflux temperature for 3 hours. Then, the reaction was completed. After the reaction, the THF serving as the solvent was distilled off under reduced pressure. Next, 500 ml of toluene was added to redissolve a product from the reaction. Then, 300 ml of water was further added, and waterwash separation was performed. Thus obtained organic layer was washed once with an aqueous solution of sodium hydroxide of 5 wt %, once with an aqueous solution of sodium hydroxide of 2 wt %, once with an aqueous solution of (1+9) chloride acid twice with water, once with sodium hydrogen carbonate of 5 wt %, and twice with water. Thereby, a water layer became neutral. Next, the organic layer was separated, and dehydrated with magnesium sulfuric anhydride. Then, toluene was distilled off therefrom. This produced 110.0 g (yield 90%) of product, which was light yellow and oily and had residual chloride content not more than 0.01%.

Into a 2 L four-necked flask, cyclotriphosphazene in which 4-methoxyphenoxy group and phenoxy group were mixedly substituted, and 583.6 g (5.05 mol) of pyridine chlorate were introduced. They were gradually heated and reacted at 205-210° C. for one hour. Later process was carried out in the same manner as in Synthesis Example 2, thereby obtaining 104.9 g of yellow solid (yield 92%). The product had residual chloride content not more than 0.01% and hydroxide content of 4.6% (theoretical value 4.5%; composition $(N_3P_3(OC_6H_5)_{3.15}(OC_6H_4OH)_{1.85}(OC_6H_4O)_{0.50})$; hydroxide group equivalent 370; a content ratio of phenyl group and hydroxyphenyl group was $[\{(OC_6H_5)_{3.15}+(OC_6H_4OH)_{1.85}\}\times100]/\{(OC_6H_5)_{4.15}+(OC_6H_4OH)_{1.85}\}=(5\times100)/6=83.3\%))$, where the structure of the phenoxyphosphazene compound before crosslinking is put as $\{(OC_6H_5)_{4.15}+(OC_6H_4OH)_{1.85}\}$, for example.) TG/DTA analysis (thermogravimetric analysis) of the cross-linked phenoxyphosphazene compound showed that its decomposition point was 322° C. and 5% weight reduction temperature was 332° C.

Example 1

An Example of Synthesis of Double-bond Phosphazene Compound

Into a three-necked flask provided with a reflux tube, 23.4 g (including 84.0 mmol of hydroxide group) of the phenoxyphosphazene compound synthesized in Synthesis Example 4, and 40.0 g of tetrahydrofuran were introduced, the phenoxyphosphazene compound having hydroxide group with hydroxide group equivalent 279. Then, they were completely dissolved. 13.1 g (92.4 mmol) of glycidyl methacrylate, 0.4 g (4.2 mmol) of triethylamine were further added therein under nitrogen atmosphere with stirring. Thus prepared reaction solution was heated to 70° C. and stirred for 8 hours. After being concentrated, the reaction solution was introduced into hexane and then decanted, thereby to separate a product therefrom (in this way, unreacted glycidyl methacrylate was removed). The product was dried under vacuum for one night. This produced 27.9 g of a phosphazene compound having an unsaturated double bond (methacryloyl group). The phosphazene compound was light brown and highly viscous material. The product was measured as to 1 H-NMR spectrum, and integration values of two signals (5.7 and 6.0 ppm) of alkene derived from methacryloyl group and of a signal (6.6-7.2 ppm) of an aromatic compound derived from the phosphazene compound were compared. From this, it was confirmed that reaction ratio (addition of methacryloyl group to hydroxide group of the phenoxyphosphazene compound) was approximately 50%.

Example 2

An Example of Synthesis of Double-bond Phosphazene Compound

Into a three-necked flask provided with a reflux tube, 23.4 g (including 84.0 mmol of hydroxide group) of the phenoxyphosphazene compound synthesized in Synthesis Example 4, and 40.0 g of tetrahydrofuran were introduced, the phenoxyphosphazene compound having hydroxide group with hydroxide group equivalent 279. Then, they were completely dissolved. 35.8 g (252.0 mmol) of glycidyl methacrylate, 0.4 g (4.2 mmol) of triethylamine were further added therein under nitrogen atmosphere with stirring. Thus prepared reaction solution was heated to 70° C. and stirred for 8 hours. After being concentrated, the reaction solution was introduced into hexane and then decanted, thereby to separate a product therefrom. The product was dried under vacuum for one night. This produced 33.9 g of a phosphazene compound having an unsaturated double bond (methacryloyl group). The phosphazene compound was light brown and highly viscous material.

Reaction ratio was measured in the same manner as in Example 1. The reaction ratio was approximately 100%.

Example 3

An Example of Synthesis of Double-bond Phosphazene Compound

Into a three-necked flask provided with a reflux tube, 36.12 g (including 84.0 mmol of hydroxide group) of the phenoxyphosphazene compound synthesized in Synthesis Example 5, and 75.0 g of tetrahydrofuran were introduced, the phenoxyphosphazene compound having hydroxide group with hydroxide group equivalent 430. Then, they were completely dissolved. 35.8 g (252.0 mmol) of glycidyl methacrylate, 0.4 g (4.2 mmol) of triethylamine were further added therein under nitrogen atmosphere with stirring. Thus prepared reaction solution was heated to 70° C. and stirred for 8 hours. After being concentrated, the reaction solution was introduced into hexane and then decanted, thereby to separate a product therefrom. The product was dried under vacuum for one night. This produced 44.1 g of a phosphazene compound having an unsaturated double bond (methacryloyl group). The phosphazene compound was light brown and highly viscous material.

Reaction ratio was measured in the same manner as in Example 1. The reaction ratio was approximately 80%.

Example 4

An Example of Synthesis of Double-bond Phosphazene Compound

Into a three-necked flask provided with a reflux tube, 23.4 g (including 84.0 mmol of hydroxide group) of the phenoxyphosphazene compound synthesized in Synthesis Example 4, and 40.0 g of tetrahydrofuran were introduced, the phenoxyphosphazene compound having hydroxide group with hydroxide group equivalent 297. Then, they were completely dissolved. 18.8 g (42.0 mmol) of EA-1010, 0.4 g (4.2 mmol) of triethylamine were further added therein under nitrogen atmosphere with stirring. Thus prepared reaction solution was heated to 70° C. and stirred for 8 hours. After being concentrated, the reaction solution was introduced into hexane and then decanted, thereby to separate a product therefrom. The product was dried under vacuum for one night. This produced 40.1 g of a phosphazene compound having an unsaturated double bond (acryloyl group). The phosphazene compound was light brown and highly viscous material. The product was measured as to 1 H-NMR spectrum, and integration values of signals (6.0, 6.3, and 6.6 ppm) derived from methacryloyl group and of a signal (7.3 ppm) of derived from phenoxy of the phosphazene compound were compared. From this, it was confirmed that reaction ratio (addition of methacryloyl group to hydroxide group of the phenoxyphosphazene compound) was approximately 50%.

Example 5

An Example of Synthesis of Double-bond Phosphazene Compound

Into a three-necked flask provided with a reflux tube, 23.4 g (including 84.0 mmol of hydroxide group) of the phenoxyphosphazene compound synthesized in Synthesis Example 4, and 40.0 g of tetrahydrofuran were introduced, the phenoxyphosphazene compound having hydroxide group with hydroxide group equivalent 297. Then, they were completely dissolved. 37.6 g (84.0 mmol) of EA-1010, 0.4 g (4.2 mmol) of triethylamine were further added therein under nitrogen atmosphere with stirring. Thus prepared reaction solution was heated to 70° C. and stirred for 8 hours. After being concentrated, the reaction solution was introduced into hexane and then decanted, thereby to separate a product therefrom. The product was dried under vacuum for one night. This produced 58.2 g of a phosphazene compound having an unsaturated double bond (acryloyl group). The phosphazene compound was light brown and highly viscous material.

Reaction ratio was measured in the same manner as in Example 4. The reaction ratio was approximately 100%.

Example 6

An Example of Synthesis of Double-bond Phosphazene Compound

Into a three-necked flask provided with a reflux tube, 36.12 g (including 84.0 mmol of hydroxide group) of the phenoxyphosphazene compound synthesized in Synthesis Example 5, and 75.0 g of tetrahydrofuran were introduced, the phenoxyphosphazene compound having hydroxide group with hydroxide group equivalent 430. Then, they were completely dissolved. 37.6 g (84.0 mmol) of EA-1010, 0.4 g (4.2 mmol) of triethylamine were further added therein under nitrogen atmosphere with stirring. Thus prepared reaction solution was heated to 70° C. and stirred for 8 hours. After being concentrated, the reaction solution was introduced into hexane and then decanted, thereby to separate a product therefrom. The product was dried under vacuum for one night. This produced 67.7 g of a phosphazene compound having an unsaturated double bond (acryloyl group). The phosphazene compound was light brown and highly viscous material.

Reaction ratio was measured in the same manner as in Example 4. The reaction ratio was approximately 100%.

Example 7

An Example of Synthesis of Double-bond Phosphazene Compound

Into a three-necked flask provided with a reflux tube, 19.77 g (including 150 mmol of hydroxide group) of the phenoxyphosphazene compound synthesized in Synthesis Example 2, 14.2 g (100 mmol) of glycidyl methacrylate, and 0.4 g (4.2 mmol) of triethylamine were added under nitrogen atmosphere with stirring, the phenoxyphosphazene compound having hydroxide group with 131.8 hydroxide equivalent. Thus prepared reaction solution was heated to 70° C. and stirred for 8 hours. The reaction solution was introduced into hexane and then decanted, thereby to separate a product therefrom. The product was dried under vacuum for one night. This produced 27.0 g of a phosphazene compound having an unsaturated double bond (methacryloyl group). The phosphazene compound was light brown and highly viscous material.

Reaction ratio was measured in the same manner as in Example 1. The reaction ratio was approximately 60%.

Example 8

An Example of Synthesis of Double-bond Phosphazene Compound

Into a three-necked flask provided with a reflux tube, 20.1 g (including 150 mmol of hydroxide group) of the phenoxyphosphazene compound synthesized in Synthesis Example 3, 14.2 g (100 ml) of glycidyl methacrylate, and 0.4 g (4.2 mmol) of triethylamine were added under nitrogen atmosphere with stirring, the phenoxyphosphazene compound having hydroxide group with 133.9 hydroxide equivalent. Thus prepared reaction solution was heated to 70° C. and stirred for 8 hours. The reaction solution was introduced into hexane and then decanted, thereby to separate a product therefrom. The product was dried under vacuum for one night. This produced 27 g of a phosphazene compound having an unsaturated double bond (methacryloyl group). The phosphazene compound was light brown and highly viscous material.

Reaction ratio was measured in the same manner as in Example 1. The reaction ratio was approximately 55%.

Example 9

An Example of Synthesis of Double-bond Phosphazene Compound

Into a three-necked flask provided with a reflux tube, 37 g (including 100 mmol of hydroxide group) of the phenoxyphosphazene compound synthesized in Synthesis Example 6, 9.94 g (70 mmol) of glycidyl methacrylate, and 0.4 g (4.2 mmol) of triethylamine were added under nitrogen atmosphere with stirring, the phenoxyphosphazene compound having hydroxide group with 370 hydroxide equivalent. Thus prepared reaction solution was heated to 70° C. and stirred for 8 hours. After being concentrated, the reaction solution was introduced into hexane and then decanted, thereby to separate a product therefrom. The product was dried under vacuum for one night. This produced 41.0 g of a phosphazene compound having an unsaturated double bond (methacryloyl group). The phosphazene compound was light brown and highly viscous material.

Reaction ratio was measured in the same manner as in Example 1. The reaction ratio was approximately 60%.

Example 10

The following components (a) to (d) were added together, and thoroughly mixed by using a three-arm roll mil, thereby to obtain a photosensitive resin composition.
(a) the double-bond phosphazene compound synthesized in Example 1: 100 parts by weight
(b) Photoreaction initiator
bis(2,4,6-trimethylbenzoyl)phenylphosphinoxide (Ciba Specialty Chemicals): 2 parts by weight
(c) Other
Epoxyacrylate resin (novolaks: commercial name K-48C, acid value 63, solid content 60 wt %): 10 parts by weight
bisphenol A EO denatured (recurring unit of ethylene oxide denatured portion; m+n≈4) diacrylate (TOAGOSEI CO., LTD. ): 10 parts by weight
bisphenol A diglycidylether acrylate additive (KYOEISHA CHEMICAL Co., LTD): 10 parts by weight
4.4' diaminodiphenylmethane: 1 part by weight
barium sulfate: 10 parts by weight
aluminum hydroxide: 10 parts by weight The thus obtained photosensitive resin composition was evaluated in various properties. The photosensitive resin composition was regarded as being proper in the flame retardancy test. In the soldering heat resistance test, the photosensitive resin component was regarded as being proper until 300° C. when treated with the normal condition and until 290° C when treated with the humid condition. Further, in the development test, the photosensitive resin composition was regarded as being proper because a square hole of 100 μm×100 μm was developed. As to anti-migration property, $5 \times 10^8 \Omega$ was observed after 1000 hours, and no abnormality such as color change or the like was observed in the copper foil. Thus, the photosensitive resin composition was regarded as being proper in view of anti-migration property. Moreover, the photosensitive resin composition was regarded as being proper in view of adhesiveness. Insulation resistance of the photosensitive resin composition was $2 \times 10^{13} \Omega$.

Example 11

A photosensitive resin composition was prepared in the same manner as in Example 10, except that the double-bond phosphazene compound of Example 10 was replaced with the double-bond phosphazene compound synthesized in Example 2.

The thus obtained photosensitive resin composition was evaluated in view of various properties. The photosensitive resin composition was regarded as being proper in the flame retardancy test. In the soldering heat resistance test, the photosensitive resin component was regarded as being proper until 305° C. when treated with the normal condition and until 295° C. when treated with the humid condition. Further, in the development test, the photosensitive resin composition was regarded as being proper because a square hole of 100 μm×100 μm was developed. As to anti-migration property, $7 \times 10^8 \Omega$ was observed after 1000 hours, and no abnormality such as color change or the like was observed in the copper foil. Thus, the photosensitive resin composition was regarded as being proper in view of anti-migration property. Moreover, the photosensitive resin composition was regarded as being proper in view of adhesiveness. Insulation resistance of the photosensitive resin composition was $3 \times 10^{13} \Omega$.

Example 12

A photosensitive resin composition was prepared in the same manner as in Example 10, except that the double-bond phosphazene compound of Example 10 was replaced with the double-bond phosphazene compound synthesized in Example 3.

The thus obtained photosensitive resin composition was evaluated in various properties. The photosensitive resin composition was regarded as being proper in the flame retardancy test. In the soldering heat resistance test, the photosensitive resin component was regarded as being proper until 290° C. when treated with the normal condition and until 285° C. when treated with the humid condition. Further, in the development test, the photosensitive resin composition was regarded as being proper because a square hole of 100

μm×100 μm was developed. As to anti-migration property, $4\times10^8\Omega$ was observed after 1000 hours, and no abnormality such as color change or the like was observed in the copper foil. Thus, the photosensitive resin composition was regarded as being proper in view of anti-migration property. Moreover, the photosensitive resin composition was regarded as being proper in view of adhesiveness. Insulation resistance of the photosensitive resin composition was $5\times10^{13}\Omega$.

Example 13

A photosensitive resin composition was prepared in the same manner as in Example 10, except that the double-bond phosphazene compound of Example 10 was replaced with the double-bond phosphazene compound synthesized in Example 4.

The thus obtained photosensitive resin composition was evaluated in various properties. The photosensitive resin composition was regarded as being proper in the flame retardancy test. In the soldering heat resistance test, the photosensitive resin component was regarded as being proper until 305° C. when treated with the normal condition and until 300° C. when treated with the humid condition. Further, in the development test, the photosensitive resin composition was regarded as being proper because a square hole of 100 μm×100 μm was developed. As to anti-migration property, $8\times10^8\Omega$ was observed after 1000 hours, and no abnormality such as color change or the like was observed in the copper foil. Thus, the photosensitive resin composition was regarded as being proper in view of anti-migration property. Moreover, the photosensitive resin composition was regarded as being proper in view of adhesiveness. Insulation resistance of the photosensitive resin composition was $2\times10^{13}\Omega$.

Example 14

A photosensitive resin composition was prepared in the same manner as in Example 10, except that the double-bond phosphazene compound of Example 10 was replaced with the double-bond phosphazene compound synthesized in Example 5.

The thus obtained photosensitive resin composition was evaluated in various properties. The photosensitive resin composition was regarded as being proper in the flame retardancy test. In the soldering heat resistance test, the photosensitive resin component was regarded as being proper until 310° C. when treated with the normal condition and until 300° C when treated with the humid condition. Further, in the development test, the photosensitive resin composition was regarded as being proper because a square hole of 100 μm×100 μm was developed. As to anti-migration property, $7\times10^8\Omega$ was observed after 1000 hours, and no abnormality such as color change or the like was observed in the copper foil. Thus, the photosensitive resin composition was regarded as being proper in view of anti-migration property. Moreover, the photosensitive resin composition was regarded as being proper in view of adhesiveness. Insulation resistance of the photosensitive resin composition was $4\times10^{13}\Omega$.

Example 15

A photosensitive resin composition was prepared in the same manner as in Example 10, except that the double-bond phosphazene compound of Example 10 was replaced with the double-bond phosphazene compound synthesized in Example 6.

The thus obtained photosensitive resin composition was evaluated in various properties. The photosensitive resin composition was regarded as being proper in the flame retardancy test. In the soldering heat resistance test, the photosensitive resin component was regarded as being proper until 315° C. when treated with the normal condition and until 300° C. when treated with the humid condition. Further, in the development test, the photosensitive resin composition was regarded as being proper because a square hole of 100 μm×100 μm was developed. As to anti-migration property, $7\times10^8\Omega$ was observed after 1000 hours, and no abnormality such as color change or the like was observed in the copper foil. Thus, the photosensitive resin composition was regarded as being proper in view of anti-migration property. Moreover, the photosensitive resin composition was regarded as being proper in view of adhesiveness. Insulation resistance of the photosensitive resin composition was $6\times10^{13}\Omega$.

Example 16

A photosensitive resin composition was prepared in the same manner as in Example 10, except that the double-bond phosphazene compound of Example 10 was replaced with the double-bond phosphazene compound synthesized in Example 7.

The thus obtained photosensitive resin composition was evaluated in various properties. The photosensitive resin composition was regarded as being proper in the flame retardancy test. In the soldering heat resistance test, the photosensitive resin component was regarded as being proper until 305° C. when treated with the normal condition and until 295° C. when treated with the humid condition. Further, in the development test, the photosensitive resin composition was regarded as being proper because a square hole of 100 μm×100 μm was developed. As to anti-migration property, $4\times10^8\Omega$ was observed after 1000 hours, and no abnormality such as color change or the like was observed in the copper foil. Thus, the photosensitive resin composition was regarded as being proper in view of anti-migration property. Moreover, the photosensitive resin composition was regarded as being proper in view of adhesiveness. Insulation resistance of the photosensitive resin composition was $5\times10^{13}\Omega$.

Example 17

A photosensitive resin composition was prepared in the same manner as in Example 10, except that the double-bond phosphazene compound of Example 10 was replaced with the double-bond phosphazene compound synthesized in Example 8.

The thus obtained photosensitive resin composition was evaluated in various properties. The photosensitive resin composition was regarded as being proper in the flame retardancy test. In the soldering heat resistance test, the photosensitive resin component was regarded as being proper until 325° C. when treated with the normal condition and until 310° C. when treated with the humid condition. Further, in the development test, the photosensitive resin composition was regarded as being proper because a square hole of 100 μm×100 μm was developed. As to anti-migration property, $1\times10^9\Omega$ was observed after 1000 hours, and no abnormality such as color change or the like was observed in the copper foil. Thus, the photosensitive resin composition got was regarded as being proper in view of anti-migration property. Moreover, the photosensitive resin composition was regarded as being proper in view of adhesiveness. Insulation resistance of the photosensitive resin composition was $6\times10^{13}\Omega$.

Example 18

A photosensitive resin composition was prepared in the same manner as in Example 10, except that the double-bond phosphazene compound of Example 10 was replaced with the double-bond phosphazene compound synthesized in Example 9.

The thus obtained photosensitive resin composition was evaluated in various properties. The photosensitive resin composition was regarded as being proper in the flame retardancy test. In the soldering heat resistance test, the photosensitive resin component was regarded as being proper until 305° C. when treated with the normal condition and until 290° C. when treated with the humid condition. Further, in the development test, the photosensitive resin composition was regarded as being proper because a square hole of 100 μm×100 μm was developed. As to anti-migration property, $6\times10^{8}\Omega$ was observed after 1000 hours, and no abnormality such as color change or the like was observed in the copper foil. Thus, the photosensitive resin composition was regarded as being proper in view of anti-migration property. Moreover, the photosensitive resin composition was regarded as being proper in view of adhesiveness. Insulation resistance of the photosensitive resin composition was $5\times10^{13}\Omega$.

Comparative Example 1

A photosensitive resin composition was prepared in the same manner as in Example 10 except that the double-bond phosphazene compound of Example 10 was omitted. The thus obtained photosensitive resin composition was evaluated in various properties. The photosensitive resin composition was regarded as being improper in the flame retardancy test. In the soldering heat resistance test, the photosensitive resin component was regarded as being improper at 270° C. when treated either with the normal condition or with the humid condition. Further, in the development test, the photosensitive resin composition was regarded as being proper because a square hole of 100 μm×100 μm was developed. As to anti-migration property, short-circuit occurred at 100 hours. Moreover, the photosensitive resin composition was regarded as being proper in view of adhesiveness. Insulation resistance of the photosensitive resin composition was $2\times10^{11}\Omega$.

Synthesis Example 7

Synthesis Example of Soluble Polyimide Resin (E)

Into a 500 ml separable flask provided with a stirring device, 17.3 g (0.030 mol) of 2,2-bis(4-hydroxyphenyl)propanedibenzoate-3,3',4,4'-tetracarboxylic dianhydride (ESDA) and 30 g of DMF were introduced, and stirred to dissolve by using the stirring device. Next, 5.15 g (0.018 mol) of [bis(4-amino-3-carboxy)phenyl]methane (MBAA) made by Wakayama Seika Co., Ltd. was dissolved in 9 g of dimethylformamide (DMF) and added in the content. Then, the content was stirred vigorously for one hour.

Further, 7.47 g (0.009 mol) of silicon diamine KF-8010 (commercial name: product of Shin-Etsu Silicone Co., Ltd.) was added therein. Then, the resultant was stirred for about one hour. Finally, 1.29 g (0.003 mol) of diamine made by Wakayama Seika Co., Ltd. (whose commercial name is BAPS-M, bis[4-(3-aminophenoxy)phenyl]sulfone). Then, the content was vigorously stirred for one hour. In this way a polyamide solution was obtained. The polyamide solution was transferred into a vat coated with Teflon (registered trademark) and dried in a vacuum oven under reduced pressure for 2 hours applying a temperature of 200° C and pressure of 5000 Pa, thereby obtaining 26.40 g of a soluble polyimide resin.

Then, 15 g of the soluble polyimide resin thus synthesized was dissolved in 50 g of dioxolane thereby to prepare a varnish, which had Sc (solid content) of 30%.

Synthesis Example 8

Synthesis Example of Soluble Polyimide Resin (E)

20.8 g (0.020 mol) of the soluble polyimide resin thus synthesized in Synthesis Example 7 was dissolved in 55 g of dioxolane. Then, 0.030 g of Q1301 produced by Wako Pure Chemical Industries, Ltd. was added and dissolved therein warming the content by using an oil bath of 60° C. Then, 3.75 g (0.0264 mol) of glycidilymethacrylate was dissolved in 5 g of dioxolane and added into the solution thus prepared. Further, 0.01 g of triethylamine was added therein as a catalyst. Then, the solution was stirred at 60° C. for 6 hours. Then, 22.4 g (0.05 mol) of NK-oligo EA-1010 (produced by SHIN-NAKAMURA CHEMICAL CO., LTD.) was added therein. Then, the solution was stirred at 60° C. for 6 hours. The solution was introduced and crushed in a beach blader in which 1 L of methanol had been purred and whose blade rotating at 11700 rpm. Resin content precipitated was filtered out. The filtrate was extracted with a Soxhlet extractor using methanol as a solvent, and then dried, thereby obtaining 21 g of the soluble polyimide resin. The soluble polyimide resin was dissolved in dioxolane. In this way, a soluble polyimide resin adjusted to Sc (solid content) of 30%.

Synthesis Example 9

Synthesis Example of Soluble Polyimide Resin (E)

Into a 500 ml separable flask provided with a stirring device, 15.6 g (0.030 mol) of 4,4'-(4,4'-isopropyridinediphenoxy)bisphthalic anhydride and 30 g of DMF were added and stirred to dissolve by using the stirring device. 6.58 g (0.023 mol) of diamine MBAA produced by Wakayama Seika Co., Ltd. was dissolved in 9 g of DMF and added therein. Then, the solution thus obtained was stirred for one hour. Further, 5.81 g (0.007 mol) of silicondiamine KF-8010 (Shin-Etsu Silicone Co., Ltd.) was added. Then, the solution was stirred for about one hour. In this way, a polyamide solution was obtained. The polyamide solution was transferred into a vat coated with Teflon (registered trademark) and dried in a vacuum oven under reduced pressure for 2 hours applying a temperature of 200° C. and pressure of 5000 Pa, thereby obtaining 26.0 g of a soluble polyimide resin.

17.94 g (0.020 mol) of the thus prepared soluble polyimide resin was dissolved in 68.5 g of dioxolane. Then, 0.030 g of Q1301 produced by Wako Pure Chemical Industries, Ltd. was added and dissolved therein warming the content by using an oil bath of 60° C. 11.4 g (0.030 mol) of the above-mentioned compound (Chemical 24) was dissolved in 5 g of dioxolane and added into the prepared solution. Further, 0.01 g of triethylamine was added therein as a catalyst. Then, the solution was stirred at 60° C. for 6 hours. In this way, a soluble polyimide resin adjusted to Sc (solid content) of 30% was synthesized.

Synthesis Example 10

Synthesis Example of Soluble Polyimide Resin (E)

Into a 500 ml separable flask provided with a stirring device, 17.64 g (0.060 mol) of 2,3,3',4'-biphenyltetracarboxylic anhydride and 50 g of DMF were introduced, and stirred to dissolve by using the stirring device. Next, 12.87 g (0.045 mol) of diamine MBAA produced by Wakayama Seika Co., Ltd. was added therein. Then, the content was stirred for one hour vigorously. Further, 12.45 g (0.015 mol) of silicondiamine KF-8010 (commercial name: produced by Shin-Etsu Silicone Co., Ltd.) was added therein. Then, the content was stirred about for one hour. In this way a polyamide solution was obtained. The polyamide solution was transferred into a vat coated with Teflon (registered trademark) and dried in a vacuum oven under reduced pressure for 2 hours applying a temperature of 200° C. and pressure of 5000 Pa, thereby obtaining 39.0 g of a soluble polyimide resin.

27.2 g (0.040 mol) of the thus synthesized soluble polyimide resin was dissolved in 83.3 g of dioxolane. Then, 0.030 g of Q1301 produced by Wako Pure Chemical Industries, Ltd. was added therein and dissolved warming the content by using an oil bath of 60° C. Then, 8.95 g (0.0 63mol) of glycidilmethacrylate was dissolved in 5 g of dioxolane and added in the solution. Further, 0.01 g of triethylamine was added therein as a catalyst. Then, the solution was stirred at 60° C. for 6 hours. In this way, a soluble polyimide resin, which was denatured to Sc (solid content) of 30%, was synthesized.

Example 19

A photosensitive resin composition was prepared by mixing the following components (a) to (d) together. The photosensitive resin composition was applied on a PET film thereby to produce a photosensitive dry film resist. The photosensitive dry film resist had a thickness of approximately 25 μm on the PET film and was in a half-cured state (B stage state). On the photosensitive dry film resist with the PET film, a protection film was laminated thereby to obtain a three-layer sheet.

(a) double-bond phosphazene compound synthesized in Example 1: 35 parts by weight (based on solid content by weight)

(b) soluble polyimide resin synthesized in Synthesis Example 7: 50 parts by weight (c) A compound having a carbon-carbon double bond (monomer for copolymerization)

bisphenol A to which diglycidylether acrylate was added (KYOEISHA CHEMICAL Co., LTD: commercial name): 5 parts by weight bisphenol A EO denatured (m+n≈2) diacrylate (TOAGOSEI CO., LTD.): 10 parts by weight (d) photoreaction initiator 3,3',4'4-tetra(t-butylperoxycarbonyl)benzophenon: 1 part by weight 4,4'-diethylaminobenzophenone: 1 part by weight Development property test of the photosensitive dry film resist showed that a fine hole of 100 μm in diameter and a line of 100 μm/100 μm were developed. Thus, the photosensitive dry film resist was regarded as being proper in the development property test. As to adhesive property, the photosensitive dry film resist was regarded as being proper because no exfoliation was observed. Further, the photosensitive dry film resist was regarded as being proper in the flame retardancy test.

Soldering heat resistance: no abnormality such as swelling, exfoliation, or the like was observed after one-minute dipping at 270° C. either when treaded with the normal condition or when treated with the humid condition. Moreover, no abnormality was observed after 30-second dip at 340° C. either when treated with the normal condition or when treated with the humid condition.

Anti-migration test: a resistance of $10^8 \Omega$ or more was observed and no abnormality such as dendrite was observed after 1000 hours.

The insulation resistance was $2 \times 10^{14} \Omega$ when treated with the normal condition and $7 \times 10^{13} \Omega$ when treated with the humid condition.

Example 20

A photosensitive resin composition was prepared by mixing the following components (a) to (d) together. The photosensitive resin composition was applied on a PET film thereby to produce a photosensitive dry film resist. The photosensitive dry film resist had a thickness of approximately 25 μm on the PET film and was in a half-cured state (B stage state). On the photosensitive dry film resist with the PET film, a protection film was laminated thereby to obtain a three-layer sheet.

(a) double-bond phosphazene compound synthesized in Example 2: 35 parts by weight (based on solid content by weight)

(b) soluble polyimide resin synthesized in Synthesis Example 8: 50 parts by weight (c) A compound having a carbon-carbon double bond (monomer for copolymerization)

bisphenol A to which diglycidylether acrylate was added (KYOEISHA CHEMICAL Co., LTD: commercial name): 5 parts by weight bisphenol A EO denatured (m+n≈2) diacrylate (TOAGOSEI CO., LTD. ): 10 parts by weight (d) photoreaction initiator 3,3',4'4-tetra(t-butylperoxycarbonyl)benzophenon: 1 part by weight 4,4'-diethylaminobenzophenone: 1 part by weight Development property test of the photosensitive dry film resist showed that a fine hole of 100 μm in diameter and a line of 100 μm/100 μm were developed. Thus, the photosensitive dry film resist was regarded as being proper in the development property test. As to adhesive property, the photosensitive dry film resist was regarded as being proper because no exfoliation was observed. Further, the photosensitive dry film resist was regarded as being proper in the flame retardancy test.

Soldering heat resistance: no abnormality such as swelling, exfoliation, or the like was observed after one-minute dipping at 270° C. either when treated with the normal condition or when treated with the humid condition. Moreover, no abnormality was observed after 30-second dip at 350° C. either when treated with the normal condition or when treated with the humid condition.

Anti-migration test: a resistance of $10^8 \Omega$ or more was observed and no abnormality such as dendrite was observed after 1000 hours.

The insulation resistance was $5 \times 10^{14} \Omega$ when treated with the normal condition and $8 \times 10^{13} \Omega$ when treated with the humid condition.

Example 21

A photosensitive resin composition was prepared by mixing the following components (a) to (d) together. The photosensitive resin composition was applied on a PET film thereby to produce a photosensitive dry film resist. The photosensitive dry film resist had a thickness of approximately 25 µm on the PET film and was in a half-cured state (B stage state). On the photosensitive dry film resist with the PET film, a protection film was laminated thereby to obtain a three-layer sheet.

(a) double-bond phosphazene compound synthesized in Example 3: 35 parts by weight (based on solid content by weight)

(b) soluble polyimide resin synthesized in Synthesis Example 9: 50 parts by weight (c) A compound having a carbon-carbon double bond (monomer for copolymerization)

bisphenol A EO denatured (m+n≈30) diacrylate (SHIN-NAKAMURA CHEMICAL CO., LTD.: commercial name NK ester A-BPE-30): 5 parts by weight bisphenol A EO denatured (m+n≈2) diacrylate (TOAGOSEI CO., LTD.): 10 parts by weight (d) photoreaction initiator bis(2,4,6-trimethylbenzoil)-phenylphosphineoxide: 1 part by weight Development property test of the photosensitive dry film resist showed that a fine hole of 100 µm in diameter and a line of 100 µm/100 µm were developed. Thus, the photosensitive dry film resist was regarded as being proper in the development property test. As to adhesive property, the photosensitive dry film resist was regarded as being proper because no exfoliation was observed. Further, the photosensitive dry film resist was regarded as being proper in the flame retardancy test.

Soldering heat resistance: no abnormality such as swelling, exfoliation, or the like was observed after one-minute dipping at 270° C. either when treated with the normal condition or when treated with the humid condition. Moreover, no abnormality was observed after 30-second dip at 360° C. either when treated with the normal condition or when treated with the humid condition.

Anti-migration test: a resistance of $10^8 \Omega$ or more was observed and no abnormality such as dendrite was observed after 1000 hours.

The insulation resistance was $3 \times 10^{14} \Omega$ when treated with the normal condition and $6 \times 10^{13} \Omega$ when treated with the humid condition.

Examples 22 to 25

Examples 22 to 25 were carried out in the same manner as Example 21 except that the double-bond phosphazene compound (a) of Example 3 was replaced with the double-bond phosphazene compounds of Examples 4 to 7 respectively.

In each of Examples 22 to 25, Development property test of the photosensitive dry film resist showed that a fine hole of 100 µm in diameter and a line of 100 µm/100 µm were developed. Thus, the photosensitive dry film resist was regarded as being proper in the development property test. As to adhesive property, the photosensitive dry film resist was regarded as being proper because no exfoliation was observed. Further, the photosensitive dry film resist was regarded as being proper in the flame retardancy test.

Soldering heat resistance: In each of Examples 22 to 25, no abnormality such as swelling, exfoliation, or the like was observed after one-minute dipping at 270° C. either when treated with the normal condition or when treated with the humid condition. Moreover, no abnormality was observed after 30-second dip at 340° C. either when treated with the normal condition or when treated with the humid condition.

Anti-migration test: a resistance of $10^8 \Omega$ or more was observed and no abnormality such as dendrite was observed after 1000 hours.

The insulation resistance of Examples 22 to 25 were as follows: the insulation resistance in Examples 22 was $1 \times 10^{14} \Omega$ when treated with the normal condition and $5 \times 10^{13} \Omega$ when treated with the humid condition; the insulation resistance in Examples 23 was $2 \times 10^{14} \Omega$ when treated with the normal condition and $6 \times 10^{13} \Omega$ when treated with the humid condition; the insulation resistance in Examples 24 was $4 \times 10^{14} \Omega$ when treated with the normal condition and $8 \times 10^{13} \Omega$ when treated with the humid condition; and the insulation resistance in Examples 25 was $3 \times 10^{14} \Omega$ when treated with the normal condition and $4 \times 10^{13} \Omega$ when treated with the humid condition.

Example 26

A photosensitive resin composition was prepared by mixing the following components (a) to (d) together. The photosensitive resin composition was applied on a PET film thereby to produce a photosensitive dry film resist. The photosensitive dry film resist had a thickness of approximately 25 µm on the PET film and was in a half-cured state (B stage state). On the photosensitive dry film resist with the PET film, a protection film was laminated thereby to obtain a three-layer sheet.

(a) double-bond phosphazene compound synthesized in Example 8: 20 parts by weight (based on solid content by weight)

double-bond phosphazene compound synthesized in Example 9: 15 parts by weight (b) soluble polyimide resin synthesized in Synthesis Example 10: 50 parts by weight bisphenol A to which diglycidyl ether acrylate was added (KYOEISHA CHEMICAL Co., LTD: commercial name): 15 parts by weight (d) photoreaction initiator bis(2,4,6-trimethylbenzoil)-phenylphosphineoxide: 1 part by weight Development property test of the photosensitive dry film resist showed that a fine hole of 100 µm in diameter and a line of 100 µm/100 µm were developed. Thus, the photosensitive dry film resist was regarded as being proper in the development property test. As to adhesive property, the photosensitive dry film resist was regarded as being proper because no exfoliation was observed. Further, the photosensitive dry film resist was regarded as being proper in the flame retardancy test.

Soldering heat resistance: no abnormality such as swelling, exfoliation, or the like was observed after one-minute dipping at 270° C. either when treated with the normal condition or when treated with the humid condition. Moreover, no abnormality was observed after 30-second dip at 360° C. either when treated with the normal condition or when treated with the humid condition.

Anti-migration test: a resistance of $10^8 \Omega$ or more was observed and no abnormality such as dendrite was observed after 1000 hours.

The insulation resistance was $5 \times 10^{14} \Omega$ when treated with the normal condition and $7 \times 10^{13} \Omega$ when treated with the humid condition.

Comparative Example 2

A photosensitive resin composition was prepared by mixing the following components (a) to (d) together. The photosensitive resin composition was applied on a PET film thereby to produce a photosensitive dry film resist. The photosensitive dry film resist had a thickness of approximately 25 μm on the PET film and was in a semi-cured state (B stage state). On the photosensitive dry film resist with the PET film, a protection film was laminated thereby to obtain a three-layer sheet.

(a) double-bond phosphazene compound: 0 part by weight (based on solid content by weight)

(b) soluble polyimide resin synthesized in Synthesis Example 7: 50 parts by weight bisphenol A EO denatured (m+n≈30) diacrylate (SHIN-NAKAMURA CHEMICAL CO., LTD.: commercial name NK ester A-BPE-30): 50 parts by weight (d) photoreaction initiator
bis(2,4,6-trimethylbenzoil)-phenylphosphineoxide: 1 part by weight Development property test of the photosensitive dry film resist showed that a fine hole of 100 μm in diameter and a line of 100 μm/100 μm were developed. Thus, the photosensitive dry film resist was regarded as being proper in the development property test. As to adhesive property, the photosensitive dry film resist was regarded as being proper because no exfoliation was observed. Further, the photosensitive dry film resist was burned in the flame retardancy test, so it was regarded as being improper in the flame retardancy test.

Soldering heat resistance: no abnormality such as swelling, exfoliation, or the like was observed after one-minute dipping at 270° C. when treated with the normal condition but swelling was observed after one-minute dipping at 270° C. when treated with the humid condition. Moreover, no abnormality was observed after 30-second dip until 300° C. when treated with the normal condition but no abnormality was observed after 30-second dip until 270° C. when treated with the humid condition.

Anti-migration test: short-circuit was observed at 300 hours. Dendrite was also observed at that point of time.

Insulation resistance was $2\times10^{12}\Omega$ when treated with the normal condition and $7\times10^{10}\Omega$ when treated with the humid condition.

Further, as an example where the photosensitive resin composition is prepared in a manner different from the foregoing manner and an example of the photosensitive resin film obtained in this manner, the following photosensitive dry film resist was produced. A specific example of the production thereof is as follows. Further, the following shows a method for evaluating properties of organic solvent solutions and photosensitive film resists of the photosensitive resin compositions obtained in Examples 27 to 35 and Comparative Examples 3 to 8.

[Preparation 1 of Photosensitive Resin Composition]

The soluble polyimide resin (G-1) was dissolved in dioxolane, and its solid content weight ratio %(Sc) was adjusted to 30%, thereby preparing a soluble polyimide resin (g-1) solution. With respect to the solution, the phenoxyphosphazene compound (H-1), the (meth)acrylic compounds (I), and if necessary other component (J) were mixed/stirred, thereby preparing an organic solvent solution of the photosensitive resin composition so that its final solid content weight ratio %(Sc) was 30%. Here, the solid content weight ratio means a total weight of materials other than the organic solvent, that is, a total weight of the components (G-1), (H-1), (I), and (J). Even a liquid material was regarded as the solid component.

[Production of Photosensitive Dry Film Resist]

The organic solvent solution of the photosensitive resin composition obtained in [Preparation 1 of photosensitive resin composition] was applied to the support film so that thickness after being dried (thickness of the photosensitive dry film resist) ranged from 20 to 25 μm. As the support film, a PET film (Lumirror (commercial name) produced by TORAY ADVANCED FILM Co., Ltd: its thickness was 25 μm) was used. Thereafter, the applied layer on the support film was dried at 100° C. for two minutes, thereby removing dioxolane. In this manner, a two-layer sheet constituted of the photosensitive dry film resist/PET film (support film) was obtained. Note that, the photosensitive dry film resist layer was in a half-cured state (B stage state).

Subsequently, a polyethylene film (GF-1 (commercial name) produced by TAMAPOLY Co., Ltd: its thickness was 40 μm) was roll-laminated on the photosensitive dry film resist of the two-layer sheet at 20° C. and at a nip pressure of 75000 Pa·m, thereby obtaining a three-layer sheet (laminate sample) having three layers (the protective film, the photosensitive dry film resist, and the PET film).

[Flame Retardancy]

After exfoliating the protection film of the three-layer sheet of the photosensitive dry film resist produced in the foregoing manner, the photosensitive dry film resist was laminated on a polyimide film (25AH film produced by Kaneka Corp.) at 100° C. and at 75000 Pa·m. Next, the resultant was exposed to 600 mJ/cm² of light whose wavelength was 400 nm, and the resultant was thermally cured in an oven of 180° C. for two hours.

Thus obtained sample was cut into a size of 1.27 cm (width)×12.7 cm (length)×50 μm (thickness) (including the thickness of the polyimide film). In this way, 20 samples were prepared. Among 20 samples, 10 samples were processed (i) at 23° C. with 50% of relative humidity for 48 hours, and other 10 samples were processed (ii) at 70° C. for 168 hours, and then was cooled in a desiccator containing anhydrous calcium chloride for 4 or more hours.

An upper portion of each sample was clamped so as to be vertically fixed, and a flame of a burner was positioned near to a lower portion of the sample for 10 seconds so that the lower portion caught fire. After 10 seconds, the flame of the burner was separated away from the sample, and time (seconds) taken for the sample to be free from any flame or burning was measured. Under the foregoing condition (i) or (ii), when the sample became free from any frame or burning and realized self extinction within 5 seconds (not more than 10 seconds) after separating the flame of the burner away from the sample, the photosensitive resin composition or the photosensitive dry film resist was regarded as being proper. When even a single sample failed in self extinction within 10 seconds or when the flame rose to the clamp in the upper portion of the sample and the burning continued, the photosensitive resin composition or the photosensitive dry film resist was regarded as being improper.

[Bleed]

The polyimide film/photosensitive dry film resist laminate produced in the flame retardancy test was reserved in an environment whose temperature was 85° C. and relative humidity was 85% for 100 hours. The reserved sample was observed through an optical microscope at a scaling ratio of 10000% so as to confirm whether there is any bleeding or not.

[Developing Property]

First, an electrolysis copper foil (NDP-3 ½ oz (commercial name) produced by MITSUI MINING & SMELTING Co., LTD.) whose thickness was 18 μm was soft-etched with 10 wt % of a sulfuric aqueous solution for one minute, and was rinsed with water. Thereafter, a surface of the resultant was rinsed with ethanol and acetone and was dried. After exfoliating the protective film of the photosensitive dry film resist, the resultant was laminated on a lustrous surface of the electrolysis copper foil (having been soft-etched) at 100° C. and at 75000 Pa·m. A mask pattern having a minute square of 100× 100 μm and a square of 200×200 μm was placed on the PET film of the laminate, and the laminate was exposed to 600 mJ/cm$^2$ of light whose wavelength was 400 nm. Thereafter, a spray developing device (ES-655D (commercial name) which was an etching machine produced by Sunhayato Corporation) was used to develop the laminate in 1 wt % of potassium hydroxide aqueous solution (its temperature was 40° C.) at a spray pressure of 0.85 MPa with its developing time of 30 to 180 seconds. After being developed, the laminate was rinsed with distilled water so as to remove the developer, and was dried. When at least a hole of 200×200 μm was found through the optical microscope, the laminate was regarded as being proper.

[Heat Resistance (Soldering Heat Resistance)]

A copper foil (electrolysis copper foil produced by MITSUI MINING & SMELTING Co., LTD.) whose thickness was 35 μm was cut into 5×5 cm and was subjected to soft etching with 10 wt % of sulfuric acid aqueous solution for one minute, and was rinsed with water, and then the surface was rinsed with ethanol and acetone, and thus rinsed surface was dried. Subsequently, after exfoliating the protective film of the photosensitive dry film resist cut into 4×4 cm, the resultant was laminated on a lustrous surface of the electrolysis copper foil (having been soft-etched) at 100° C. and at 75000 Pa·m. The photosensitive dry film resist of the combined sample was exposed to 300 mJ/cm$^2$ of light whose wavelength was 400 nm. Thereafter, the resultant was cured at 180° C. for two hours. The thus obtained sample was subjected to humidity conditioning under (i) a normal condition (at 20° C., with relative humidity of 40%, for 24 hours) and (ii) a moisture absorption condition (at 40° C., with relative humidity of 85%, for 48 hours). Thereafter, the sample was dipped in melted solder, whose temperature was 270° C. or higher, for 30 seconds. Then, whether or not swollenness occurred and whether or not exfoliation occurred in an interface between the copper foil and the photosensitive dry film resist were observed. Further, a temperature of the melted solder was gradually raised so as to check a temperature at which the sample was under an abnormal condition while dipping the sample for 30 seconds per 10° C. A maximum temperature which resulted no abnormal condition was defined as a 30-second-dipable temperature. When the 30-second-dipable temperature was 300° C. or higher, this sample was regarded as being proper.

[Materials Used]

As materials of the soluble polyimide resin (G-1), the following commercial products were used. The materials were (2,2'-bis(hydroxyphenyl)propanedibenzoate)-3,3',4,4'-tetra carboxylate dianhydride (product of Wakayama Seika Co., Ltd.: hereinafter, referred to as ESDA), silicondiamine (KF-8010 (commercial name) produced by Shin-Etsu Silicone Co., Ltd.), 2,2'-diaminobisphenol A (DAM-1 (commercial name) produced by Gun Ei Chemical Industry Co., Ltd.), and bis [4-(3-aminophenoxy)phenyl]sulfone (hereinafter, referred to as BAPS-M).

Further, a weight-average molecular weight of the soluble polyimide resin (G-1) was measured with a high speed GPC (HLC-8220GPC (commercial name) produced by Tosoh Corporation), and was calculated with a size exclusion chromatography in accordance with conversion based on polyethyleneoxide. Further, synthesis of the material phosphazene compound, the phenoxyphosphagen compound, and the cross-linked phenoxyphosphazene compound was carried out in the same manner as in the Synthesis Examples 1 to 6.

Synthesis Example 11

Synthesis Example of Soluble Polyimide Resin (G-1)

17.3 g (0.030 mol) of 2,2'-bis(hydroxyphenyl)propanedibenzoate-3,3',4,4'-tetracarboxylate dianhydride (ESDA) and 30 g of dimethylformamide (DMF) were placed in a 500 ml separable flask provided with a stirrer, and the mixture was stirred, thereby dissolving the mixture. Next, 5.15 g (0.018 mol) of [bis(4-amino-3-carboxy)phenyl]methane produced by Wakayama Seika Co., Ltd. (MBAA) was. dissolved in 9 g of DMF, and the mixture was stirred for one hour. After the solution became even, 7.47 g (0.009 mol) of silicondiamine (KF-8010 (commercial name) produced by Shin-Etsu Silicone Co., Ltd.) was added thereto, and the mixture was stirred for about one hour. Lastly, 1.29 g (0.003 mol) of diamine (bis[4-(3-aminophenoxy)phenyl]sulfone whose commercial name was BAPS-M produced by Wakayama Seika Co., Ltd.) was added thereto, and the mixture was intensely stirred. The polyamide solution obtained in this manner was placed in a tray coated with fluorocarbon resin and was dried in a vacuum oven at 200° C. under reduced pressure of 660 Pa for two hours, thereby obtaining 26.40 g of soluble polyimide resin having a carboxyl group. In the soluble polyimide resin, an acid equivalent was 835 and a weight-average molecular weight was 37000.

Synthesis Example 12

Synthesis of Double-bond Polyimide Resin 20.0 g of (0.020 mol) of the soluble polyimide resin synthesized in Synthesis Example 11 was dissolved in 40 g of DMF. Further, 1.71 g (0.120 mol) of methacrylate glycidyl, 0.1 g (0.001 mol) of triethylamine, and 0.02 g of N-nitrosphenylhydroxylaminealuminum salt serving as a polymerization inhibitor were added thereto, and the mixture was stirred at 80° C. for 5 hours. The thus obtained solution was poured into 500 ml of methanole, and a deposited resin component was crushed by a mixer, and the crushed resins were rinsed with methanol and was dried, thereby obtaining 113.4 g of a double-bond polyimide resin having an unsaturated double bond (methacryloyl group). In the double-bond polyimide resin, an acid equivalent was 1811 and a weight-average molecular weight was 38000.

Synthesis Example 13

Synthesis of Soluble Polyimide Resin (A-1)

69.7 g (0.27 mol) of diamine DAM-1 (commercial name) produced by Gun Ei Chemical Industry Co., Ltd. and 100 g of DMF-1 (commercial name) were placed in a 500 ml separable flask provided with a stirrer, thereby preparing a DMF solution of DAM-1. Next, 24.9 g (0.03 mol) of silicondiamine (KF-8010 (commercial name) produced by Shin-Etsu Silicone Co., Ltd.) was added thereto, and the mixture was intensely stirred. After the solution became even, a solution obtained by dissolving 173 g (0.30 mol) of ESDA in 300 g of DMF was added thereto, and the mixture was intensely stirred for about one hour. The polyamide acid solution obtained in this manner was placed in a tray coated with fluorocarbon resin and was dried in a vacuum oven at 200° C. under reduced pressure of 660 Pa for two hours, thereby obtaining 241.0 g of soluble polyimide resin having a hydroxyl group. In the soluble polyimide resin, an acid equivalent was 475 and a weight-average molecular weight was 26000.

Synthesis Example 12

Synthesis of Double-bond Polyimide Resin 100 g of the soluble polyimide resin synthesized in Synthesis Example 13 was dissolved in 200 g of DMF. Further, 15.1 g (0.11 mol) of methacrylate glycidyl, 1.0 g (0.01 mol) of triethylamine, and 0.1 g of N-nitrosphenylhydroxylaminealuminum salt serving as a polymerization inhibitor were added thereto, and the mixture was stirred at 80° C. for 5 hours. The thus obtained solution was poured into 500 ml of methanole, and a deposited resin component was crushed by a mixer, and the crushed resins were rinsed with methanol and was dried, thereby obtaining 113.4 g of a double-bond polyimide resin having an unsaturated double bond (methacryloyl group). In the double-bond polyimide resin, an acid equivalent was 1132 and a weight-average molecular weight was 30000.

Example 27

15 g of the soluble polyimide resin synthesized in Synthesis Example 11 was dissolved in 35 g of dioxolane, thereby preparing an organic solvent solution so that its solid content weight ratio (Sc) was 30%.

An organic solvent solution of the photosensitive resin composition was prepared by mixing the following components so as to produce a photosensitive dry film resist in a B stage state.
(a) Soluble Polyimide Resin
Soluble polyimide resin synthesized in Synthesis Example 11 (in accordance with conversion based on a solid content): 40 parts by weight
(b) Phenoxyphosphazene Compound
Circular phenoxyphosphazene compound synthesized in Synthesis Example 2: 25 parts by weight
(c) (Meth)acrylic Compound
Bisphenol A EO denaturalized (recurring unit of an ethyleneoxide denaturalized portion: m+n≈4) diacrylate (ARONIX M-211B (commercial name) produced by TOAGOSEI CO., LTD.): 5 parts by weight
Bisphenol A EO denaturalized (recurring unit of an ethyleneoxide denaturalized portion: m+n≈30) diacrylate (NK ester A-BPE-30 (commercial name) produced by SHIN-NAKAMURA CHEMICAL CO., LTD.): 20 parts by weight
(d) Other Component
Photoreaction initiator
Bis (2,4,6-trimethylbenzoyl)phenylphosphinoxide (IRGACURE 819 (commercial name) produced by Ciba Specialty Chemicals): 1 part by weight
Epoxy Resin
Bisphenol A type epoxy resin (Epikote 828 (commercial name) produced by Japan Epoxy Resins Co., Ltd.): 10 parts by weight
Curing Agent
4,4'-diaminodiphenylmethane (DDM): 1 part by weight
Properties of the thus obtained photosensitive dry film resist were evaluated as follows.
Flame retardancy test: The flame disappeared in 3.5 seconds on the average, so that this was regarded as being proper.
Bleed: There was no bleed.
Developing property: Both a hole of 100×100 µm and a hole of 200×200 µm were developed, so that the photosensitive dry film resist was regarded as being proper in this view point.
Heat resistance: Under both the normal condition and the moisture absorption condition, the 30-second-dipable temperature was 320° C., so that the photosensitive dry film resist was regarded as being proper in this view point.

Example 28

15 g of the double-bond polyimide resin synthesized in Synthesis Example 12 was dissolved in 35 g of dioxolane, thereby preparing an organic solvent solution so that its solid content weight ratio (Sc) was 30%.
An organic solvent solution of the photosensitive resin composition was prepared by mixing the following components so as to produce a photosensitive dry film resist in a B stage state.
(a) Soluble Polyimide Resin
Double-bond polyimide resin synthesized in Synthesis Example 12 (in accordance with conversion based on a solid content): 50 parts by weight
(b) Phenoxyphosphazene Compound
Circular phenoxyphosphazene compound and the chain phenoxyphosphazene compound synthesized in Synthesis Example 3: 25 parts by weight
(c) (Meth)acrylic Compound
Bisphenol A EO denaturalized (recurring unit of an ethyleneoxide denaturalized portion: m+n≈10) diacrylate (NK ester A-BPE-10 (commercial name) produced by SHIN-NAKAMURA CHEMICAL CO., LTD.)): 10 parts by weight
Bisphenol A EO denaturalized (recurring unit of an ethyleneoxide denaturalized portion: m+n≈30) diacrylate (NK ester A-BPE-30 (commercial name) produced by SHIN-NAKAMURA CHEMICAL CO., LTD.): 15 parts by weight
(d) Other Component
Photoreaction initiator
Bis(2,4,6-trimethylbenzoyl)phenylphosphinoxide (IRGACURE 819 (commercial name) produced by Ciba Specialty Chemicals): 1 part by weight
Properties of the thus obtained photosensitive dry film resist were evaluated as follows.
Flame retardancy test: The flame disappeared in 3.0 seconds on the average, so that this was regarded as being proper.
Bleed: There was no bleed.
Developing property: Both a hole of 100×100 µm and a hole of 200×200 µm were developed, so that the photosensitive dry film resist was regarded as being proper in this view point.
Heat resistance: Under both the normal condition and the moisture absorption condition, the 30-second-dipable temperature was 330° C., so that the photosensitive dry film resist was regarded as being proper in this view point.

Example 29

15 g of the double-bond polyimide resin synthesized in Synthesis Example 12 was dissolved in 35 g of dioxolane, thereby preparing an organic solvent solution so that its solid content weight ratio (Sc) was 30%.
An organic solvent solution of the photosensitive resin composition was prepared by mixing the following components so as to produce a photosensitive dry film resist in a B stage state.

(a) Soluble Polyimide Resin
Double-bond polyimide resin synthesized in Synthesis Example 12 (in accordance with conversion based on a solid content): 50 parts by weight
(b) Phenoxyphosphazene Compound
Circular phenoxyphosphazene compound synthesized in Synthesis Example 4: 20 parts by weight
(c) (Meth)acrylic Compound
Bisphenol A EO denaturalized (recurring unit of an ethyleneoxide denaturalized portion: m+n=4) diacrylate (ARONIX M-211B (commercial name) produced by TOAGOSEI CO., LTD.): 5 parts by weight
Bisphenol A EO denaturalized (recurring unit of an ethyleneoxide denaturalized portion: m+n≈30) diacrylate (NK ester A-BPE-30 (commercial name) produced by SHIN-NAKAMURA CHEMICAL CO., LTD.): 15 parts by weight
Epoxyacrylate (NK oligo EA-1010 (commercial name) produced by SHIN-NAKAMURA CHEMICAL CO., LTD.): 10 parts by weight
(d) Other Component
Photoreaction Initiator
Bis (2,4,6-trimethylbenzoyl)phenylphosphinoxide (IRGACURE 819 (commercial name) produced by Ciba Specialty Chemicals): 1 part by weight Properties of the thus obtained photosensitive dry film resist were evaluated as follows.

Flame retardancy test: The flame disappeared in 3.0 seconds on the average, so that this was regarded as being proper.

Bleed: There was no bleed.

Developing property: Both a hole of 100×100 μm and a hole of 200×200 μm were developed, so that the photosensitive dry film resist was regarded as being proper in this view point.

Heat resistance: Under both the normal condition and the moisture absorption condition, the 30-second-dipable temperature was 330° C., so that the photosensitive dry film resist was regarded as being proper in this view point.

Example 30

15 g of the soluble polyimide resin synthesized in Synthesis Example 13 was dissolved in 35 g of dioxolane, thereby preparing an organic solvent solution so that its solid content weight ratio (Sc) was 30%.

An organic solvent solution of the photosensitive resin composition was prepared by mixing the following components so as to produce a photosensitive dry film resist in a B stage state.

(a) Soluble Polyimide Resin
Soluble polyimide resin synthesized in Synthesis Example 13 (in accordance with conversion based on a solid content): 40 parts by weight
(b) Phenoxyphosphazene Compound
Circular phenoxyphosphazene compound synthesized in Synthesis Example 5: 25 parts by weight
(c) (Meth)acrylic Compound
Bisphenol A EO denaturalized (recurring unit of an ethyleneoxide denaturalized portion: m+n≈10) diacrylate (NK ester A-BPE-10 (commercial name) produced by SHIN-NAKAMURA CHEMICAL CO., LTD.): 10 parts by weight
Bisphenol A EO denaturalized (recurring unit of an ethyleneoxide denaturalized portion: m+n≈30) diacrylate (NK ester A-BPE-30 (commercial name) produced by SHIN-NAKAMURA CHEMICAL CO., LTD.): 15 parts by weight
(d) Other Component
Photoreaction initiator
Bis (2,4-cyclopentadiene-1-yl)-bis (2,6'-difluoro-3-(1 H-pyrrole-1-yl)-phenyl) titanium (IRGACURE 784 (commercial name) produced by Ciba Specialty Chemicals): 1 part by weight
Epoxy Resin
Bisphenol A type epoxy resin (Epikote 828 (commercial name) produced by Japan Epoxy Resins Co., Ltd.): 10 parts by weight
Curing Agent
4,4'-diaminodiphenylmethane (DDM): 1 part by weight Properties of the thus obtained photosensitive dry film resist were evaluated as follows. Flame retardancy test: The flame disappeared in 4.0 seconds on the average, so that this was regarded as being proper.

Bleed: There was no bleed.

Developing property: Both a hole of 100×100 μm and a hole of 200×200 μm were developed, so that the photosensitive dry film resist was regarded as being proper in this view point.

Heat resistance: Under both the normal condition and the moisture absorption condition, the 30-second-dipable temperature was 310° C., so that the photosensitive dry film resist was regarded as being proper in this view.

Example 31

15 g of the double-bond polyimide resin synthesized in Synthesis Example 14 was dissolved in 35 g of dioxolane, thereby preparing an organic solvent solution so that its solid content weight ratio (Sc) was 30%.

An organic solvent solution of the photosensitive resin composition was prepared by mixing the following components so as to produce a photosensitive dry film resist in a B stage state.

(a) Soluble Polyimide Resin
Double-bond polyimide resin synthesized in Synthesis Example 14 (in accordance with conversion based on a solid content): 50 parts by weight
(b) Phenoxyphosphazene Compound
Circular phenoxyphosphazene compound synthesized in Synthesis Example 6: 25 parts by weight
(c) (Meth)acrylic Compound
Bisphenol A EO denaturalized (recurring unit of an ethyleneoxide denaturalized portion: m+n≈10) diacrylate (NK ester A-BPE-10 (commercial name) produced by SHIN-NAKAMURA CHEMICAL CO., LTD.): 10 parts by weight
Bisphenol A type epoxyacrylate (Ebecryl 3700 (commercial name) produced by DAICEL-UCB Company LTD.): 15 parts by weight
(d) Other Component
Photoreaction Initiator
Bis (2,4-cyclopentadiene-1-yl)-bis (2,6'-difluoro-3-(1 H-pyrrole-1-yl)-phenyl) titanium (IRGACURE 784 (commercial name) produced by Ciba Specialty Chemicals): 1 part by weight Properties of the thus obtained photosensitive dry film resist were evaluated as follows.

Flame retardancy test: The flame disappeared in 3.0 seconds on the average, so that this was regarded as being proper.

Bleed: There was no bleed.

Developing property: Both a hole of 100×100 μm and a hole of 200×200 μm were developed, so that the photosensitive dry film resist was regarded as being proper in this view point.

Heat resistance: Under both the normal condition and the moisture absorption condition, the 30-second-dipable temperature was 320° C., so that the photosensitive dry film resist was regarded as being proper in this view point.

Comparative Example 3

Among polymers used instead of the soluble polyimide resin serving as the component (a) in Examples 27 to 31, a polymer component having a largest weight in the photosensitive resin composition is referred to as a base polymer.
(Synthesis of Base Polymer)

173 g (0.30 mol) of ESDA and 300 g of DMF were placed in a 500 ml separable flask provided with a stirrer, thereby preparing a DMF varnish of ESDA. Next, a solution obtained by dissolving 86.5 g (0.20 mol) of BAPS-M in 100 g of DMF was added to the DMF varnish, and the mixture was intensely stirred. After the solution became even, 83.5 g (0.10 mol) of silicondiamine KF-8010 (commercial name: product of Shin-Etsu Silicone Co., Ltd.) was added thereto, and the mixture was intensely stirred.

The thus obtained polyamide acid solution was placed in a tray coated with fluorocarbon resin and was dried in a vacuum oven at 200° C. under reduced pressure of 660 Pa for two hours, thereby obtaining 315 g of polyimide resin.

The polyimide resin had no carboxyl group and/or no hydroxyl group in its imide resin. Further, no photosensitive group was introduced therein.
(Production of Photosensitive Dry Film Resist)

15 g of the polyimide resin synthesized in the foregoing manner was dissolved in 35 g of dioxolane, thereby preparing a varnish whose solid content weight ratio %(Sc) was 30%.

The same operation was carried out as in Example 27 except that the polyimide resin synthesized in the present example was used instead of the component (a) of Example 27, thereby producing a photosensitive dry film resist.
(Evaluation of Properties)

Properties of the obtained photosensitive dry film resist were evaluated as follows.
Flame retardancy test: The flame disappeared in 3.0 seconds on the average, so that this was regarded as being proper.
Bleed: There was no bleed.
Developing property: Neither a hole of 100×100 µm nor a hole of 200×200 µm were developed, so that the photosensitive dry film resist was regarded as being improper in this view point.
Heat resistance: Under both the normal condition and the moisture absorption condition, the 30-second-dipable temperature was 320° C., so that the photosensitive dry film resist was regarded as being proper in this view point.

In this manner, when the polyimide resin having no carboxyl group and/or no hydroxyl group was used as a base polymer, the flame retardancy and the heat resistance of the obtained photosensitive dry film resist were favorable, but its developing property was not favorable.

Comparative Example 4

(Synthesis of Base Polymer)

Monomers of methylmethacrylate, n-butylmethacrylate, 2-ethylhexylacrylate, and methacrylic acid were used as materials for the polyimide resin. These monomer components were copolymerized in accordance with a known method, thereby obtaining a copolymer having a carboxyl group. A polymerization ratio of the monomer components was methyemethacrylate/n-butylmethacrylate/2-ethylhexylacrylate/methacrylic acid=60/10/10/20 (in terms of a weight).
(Production of Photosensitive Dry Film Resist)

The photosensitive dry film resist was produced under the same condition as in Example 28 except that the acrylic copolymer synthesized in the present example was used instead of the component (a) of Example 28.
(Evaluation of Properties)

Properties of the obtained photosensitive dry film resist were evaluated as follows.
Flame retardancy test: The flame did not disappeared within 10 seconds, and the flame rose to the clamp, so that this was regarded as being improper.
Bleed: There was no bleed.
Developing property: Both a hole of 100×100 µm and a hole of 200×200 µm were developed, so that the photosensitive dry film resist was regarded as being proper in this view point.
Heat resistance: Under the normal condition, the 30-second-dipable temperature was 280° C. Under the moisture absorption condition, the 30-second-dipable temperature was 240° C. Thus, the photosensitive dry film resist was regarded as being proper in this view point.

In this manner, when the acrylic copolymer made of a monomer having no aromatic ring was used as a base polymer, the developing property of the obtained photosensitive dry film resist was favorable, but its heat resistance was not favorable. Further, even when the phosphazene compound was used, its flame retardancy was not favorable.

Comparative Example 5

(Production of Photosensitive Dry Film Resist)

The photosensitive dry film resist was produced under the same condition as in Example 28 except that a propoxylated phosphazene compound (SPR-100 (commercial name) produced by Otsuka Chemical Co., Ltd.) was used instead of the component (b) of Example 28.
(Evaluation of Properties)

Properties of the obtained photosensitive dry film resist were evaluated as follows.
Flame retardancy test: The flame did not disappeared within 10 seconds, and the flame rose to the clamp, so that this was regarded as being improper.
Bleed: Bleeding was found.
Developing property: Both a hole of 100×100 µm and a hole of 200×200 µm were developed, so that the photosensitive dry film resist was regarded as being proper in this view point.
Heat resistance: Under both the normal condition and the moisture absorption condition, the 30-second-dipable temperature was 290° C., so that the photosensitive dry film resist was regarded as being improper in this view point.

In this manner, when the phosphazene compound having no phenolic hydroxyl group was used, the flame retardancy of the obtained photosensitive dry film resist was not sufficient, and the photosensitive dry film resist had no reactive group. This resulted in bleeding and drop of the heat resistance.

[Preparation 2 of Photosensitive Resin Composition]

The soluble polyimide resin (K) having a carboxyl group and/or a hydroxyl group was dissolved in dioxolane, and its solid content weight ratio %(Sc) was adjusted to 30%, thereby preparing a soluble polyimide resin solution. With respect to the solution, the phenoxyphosphazene compound (L), the (meth)acrylic compounds (M), and if necessary other component (L) were mixed/stirred, thereby preparing an organic solvent solution of the photosensitive resin composition so that its final solid content weight ratio %(Sc) was 50%. Here, the solid content weight ratio means a total weight of materials other than the organic solvent, that is, a total weight of the components (K), (L), (M), and (N). Even a liquid material was regarded as the solid component.

[Production of Photosensitive Dry Film Resist]

The organic solvent solution of the photosensitive resin composition obtained in [Preparation 2 of photosensitive resin composition] was applied to the support film so that thickness after being dried (thickness of the photosensitive dry film resist) ranged from 20 to 25 μm. As the support film, a PET film (Lumirror (commercial name) produced by TORAY ADVANCED FILM Co., Ltd: its thickness was 25 μm) was used. Thereafter, the applied layer on the support film was dried at 100° C. for two minutes, thereby removing dioxolane. In this manner, a two-layer sheet constituted of the photosensitive dry film resist/PET film (support film) was obtained. Note that, the photosensitive dry film resist layer was in a B stage state.

Subsequently, a polyethylene film (GF-1 (commercial name) produced by TAMAPOLY Co., Ltd: its thickness was 40 μm) was roll-laminated on the photosensitive dry film resist of the two-layer sheet at 20° C. and at a nip pressure of 75000 Pa·m, thereby obtaining a three-layer sheet having three layers (the protective film, the photosensitive dry film resist, and the PET film).

[Evaluation of Properties of Photosensitive Dry Film Resist]

As to the organic solvent solution of the photosensitive resin composition prepared in the foregoing [Preparation 2 of photosensitive resin composition] and the photosensitive dry film resist produced, the following properties thereof were evaluated. Specifically, the evaluation was carried out in terms of the flame retardancy, the developing property, and the heat resistance. These properties were evaluated in the same manner as in the evaluation of the organic solvent solution of the photosensitive resin composition and the photosensitive dry film resist that were obtained in [Preparation 1 of Photosensitive Resin Composition].

Further, as materials of the soluble polyimide resin (K) having a carboxyl group and/or a hydroxyl group, not only the materials used to synthesize the soluble polyimide resin (G-1) but also [bis(4-amino-3-carboxy)phenyl]methane (product of Wakayama Seika Co., Ltd.: hereinafter, referred to as MBAA).

Further, a weight-average molecular weight of the soluble polyimide resin (K) having a carboxyl group and/or a hydroxyl group was measured with a high speed GPC (HLC-8220GPC produced by Tosoh Corporation), and was calculated with a size exclusion chromatography in accordance with conversion based on polyethyleneoxide.

Synthesis Example 15

Synthesis of Soluble Polyimide Resin having a Carboxyl Group 17.3 g (0.030 mol) of ESDA and 30 g of dimethylformamide (hereinafter, referred to also as DMF) were placed in a 500ml separable flask provided with a stirrer, and the mixture was stirred with the stirrer so that the stirred resultant was dissolved. Next, 5.15 g (0.018 mol) of MBAA was dissolved in 9 g of DMF, and the resultant was added to the DMF solution of ESDA, and the mixture was intensely stirred. After the solution became even, 7.47 g (0.009 mol) of silicondiamine KF-8010 was added thereto, and the mixture was stirred. After the solution became even, 1.29 g (0.003 mol) of BAPS-M was added thereto, and the mixture was intensely stirred for one hour. The polyamic acid solution obtained in this manner was placed in a tray coated with fluorocarbon resin and was dried in a vacuum oven at 200° C. under reduced pressure of 660 Pa for two hours, thereby obtaining 26.40 g of soluble polyimide resin having a carboxyl group. In the soluble polyimide resin, an acid equivalent was 835 and a weight-average molecular weight was 37000.

Synthesis Example 16

Introduction of Methacryl Group into Soluble Polyimide Resin having Carboxyl Group 20.0 g (0.020 mol) of the soluble polyimide resin having a carboxyl group which had been synthesized in Synthesis Example 15 was dissolved in 40 g of DNF, and 1.71 g (0.120 mol) of glycidyl methacrylate, 0.1 g (0.001 mol) of triethylamine, and 0.02 g of N-nitrsphenylhydroxyaminealuminum salt serving as a polymerization inhibitor were added, and the mixture was stirred at 80° C. for five fours. The thus obtained solution was poured into 500 ml of methanole, and a deposited resin component was crushed by a mixer, and the crushed resins were rinsed with methanol and was dried, thereby obtaining 21.2 g of a soluble polyimide resin having a methacryl group. In the soluble polyimide resin, an acid equivalent was 1811 and a weight-average molecular weight was 38000.

Synthesis Example 17

Synthesis of Soluble Polyimide Resin having Hydroxyl Group 69.7 g (0.27 mol) of diamine DAM-1 and 100 g of DMF were placed in a 500 ml separable flask provided with a stirrer, thereby preparing a DMF solution of DAM-1. Next, 24.9 g (0.03 mol) of silicondiamine KF-8010 was added thereto, and the mixture was intensely stirred. After the solution became even, a solution obtained by dissolving 173 g (0.30 mol) of ESDA in 300 g of DMF was added thereto, and the mixture was intensely stirred for about one hour. The polyamide acid solution obtained in this manner was placed in a tray coated with fluorocarbon resin and was dried in a vacuum oven at 200° C. under reduced pressure of 660 Pa for two hours, thereby obtaining 241.0 g of soluble polyimide resin having a hydroxyl group. In the soluble polyimide resin, an acid equivalent was 475 and a weight-average molecular weight was 26000.

Synthesis Example 18

Introduction of Methacryl Group into Soluble Polyimide Resin having Hydroxyl Group 100 g of the soluble polyimide resin having a hydroxyl group which had been synthesized in Synthesis Example 17 was dissolved in 200 g of DNF, and 15.1 g (0.11 mol) of glycidyl methacrylate, 1.0 g (0.01 mol) of triethylamine, and 0.02 g of N-nitrsphenylhydroxyaminealuminum salt serving as a polymerization inhibitor were added, and the mixture was stirred at 80° C. for five fours. The thus obtained solution was poured into 500 ml of methanole, and a deposited resin component was crushed by a mixer, and the crushed resins were rinsed with methanol and was dried, thereby obtaining 113.4 g of a soluble polyimide resin having a methacryl group. In the soluble polyimide resin, an acid equivalent was 1132 and a weight-average molecular weight was 30000.

Example 32

(Production of Photosensitive Dry Film Resist)

15 g of the soluble polyimide resin synthesized in Synthesis Example 15 was dissolved in 35 g of dioxolane, thereby preparing an organic solvent solution so that its solid content weight ratio (Sc) was 30%.

An organic solvent solution of the photosensitive resin composition was prepared by mixing the following components so as to produce a photosensitive dry film resist in a B stage state.
(a) Soluble Polyimide Resin
Soluble polyimide resin synthesized in Synthesis Example 15 (in accordance with conversion based on a solid content): 50 parts by weight
(b) Cross-linked Phenoxyphosphazene Compound
A cross-linked phenoxyphosphazene compound obtained by cross-linking a circular phenoxyphosphazene compound, represented by formula (22) where a is an integer ranging from 3 to 20, with a p-phenylene group. SPS-100 (commercial name) produced by Otsuka Chemicals Inc.: 20 parts by weight
(c) (Meth)acrylic Compound
Bisphenol A EO denaturalized (recurring unit of an ethyleneoxide denaturalized portion: m+n4) diacrylate (ARONIX M-211B (commercial name) produced by TOAGOSEI CO., LTD.): 5 parts by weight Bisphenol A EO denaturalized (recurring unit of an ethyleneoxide denaturalized portion: m+n≈30) diacrylate (NK ester A-BPE-30 (commercial name) produced by SHIN-NAKAMURA CHEMICAL CO., LTD.): 15 parts by weight
(d) Other Component
Photoreaction Initiator
Bis (2,4,6-trimethylbenzoyl)phenylphosphinoxide (IRGACURE 819 (commercial name) produced by Ciba Specialty Chemicals): 1 part by weight
Epoxy Resin
Bisphenol A type epoxy resin (Epikote 828 (commercial name) produced by Japan Epoxy Resins Co., Ltd.): 10 parts by weight
Curing Agent
4,4'-diaminodiphenylmethane (DDM): 1 part by weight
(Results of Property Evaluation)

Properties of the thus obtained photosensitive dry film resist were evaluated as follows.
Flame retardancy test: The flame disappeared in 3.5 seconds on the average, so that this was regarded as being proper.
Developing property: Both a hole of 100×100 μm and a hole of 200×200 μm were developed, so that the photosensitive dry film resist was regarded as being proper in this view point.
Heat resistance: Under both the normal condition and the moisture absorption condition, the 30-second-dipable temperature was 330° C., so that the photosensitive dry film resist was regarded as being proper in this view point.

Example 33

(Production of Photosensitive Dry Film Resist)

15 g of the soluble polyimide resin synthesized in Synthesis Example 16 was dissolved in 35 g of dioxolane, thereby preparing an organic solvent solution so that its solid content weight ratio (Sc) was 30%

An organic solvent solution of the photosensitive resin composition was prepared by mixing the following components so as to produce a photosensitive dry film resist in a B stage state.
(a) Soluble Polyimide Resin
Soluble polyimide resin synthesized in Synthesis Example 16 (in accordance with conversion based on a solid content): 50 parts by weight
(b) Cross-linked Phenoxyphosphazene Compound
A cross-linked phenoxyphosphazene compound obtained by cross-linking a circular phenoxyphosphazene compound, represented by formula (22) where a is an integer ranging from 3 to 20, with a p-phenylene group. SPB-100 (commercial name) produced by Otsuka Chemicals Inc.: 20 parts by weight
(c) (Meth)acrylic Compound
Bisphenol A EO denaturalized (recurring unit of an ethyleneoxide denaturalized portion: m+n≈4) diacrylate (ARONIX M-211B (commercial name) produced by TOAGOSEI CO., LTD.): 5 parts by weight
Bisphenol A EO denaturalized (recurring unit of an ethyleneoxide denaturalized portion: m+n≈30) diacrylate (NK ester A-BPE-30 (commercial name) produced by SHIN-NAKAMURA CHEMICAL CO., LTD.): 15 parts by weight
Epoxyacrylate (NK oligo EA-1010 (commercial name) produced by SHIN-NAKAMURA CHEMICAL CO., LTD.): 10 parts by weight
(d) Other Component
Photoreaction Initiator
Bis (2,4,6-trimethylbenzoyl)phenylphosphinoxide (IRGACURE 819 (commercial name) produced by Ciba Specialty Chemicals): 1 part by weight
(Results of Property Evaluation)

Properties of the thus obtained photosensitive dry film resist were evaluated as follows.
Flame retardancy test: The flame disappeared in 3.0 seconds on the average, so that this was regarded as being proper.
Developing property: Both a hole of 100×100 μm and a hole of 200×200 μm were developed, so that the photosensitive dry film resist was regarded as being proper in this view point.
Heat resistance: Under both the normal condition and the moisture absorption condition, the 30-second-dipable temperature was 340° C., so that the photosensitive dry film resist was regarded as being proper in this view point.

Example 34

(Production of Photosensitive Dry Film Resist)

15 g of the soluble polyimide resin synthesized in Synthesis Example 17 was dissolved in 35 g of dioxolane, thereby preparing an organic solvent solution so that its solid content weight ratio (Sc) was 30%.

An organic solvent solution of the photosensitive resin composition was prepared by mixing the following components so as to produce a photosensitive dry film resist in a B stage state.
(a) Soluble Polyimide Resin
Soluble polyimide resin synthesized in Synthesis Example 17 (in accordance with conversion based on a solid content): 50 parts by weight
(b) Cross-linked Phenoxyphosphazene Compound
A cross-linked phenoxyphosphazene compound obtained by cross-linking a circular phenoxyphosphazene compound, represented by formula (22) where a is an integer ranging from 3 to 20, with a p-phenylene group. SPE-100 (commercial name) produced by Otsuka Chemicals Inc.: 20 parts by weight (c) (Meth)acrylic Compound Bisphenol A EO denaturalized (recurring unit of an ethyleneoxide denaturalized portion: m+n≈10) diacrylate (NK ester A-BPE-10 (commercial name) produced by SHIN-NAKAMURA CHEMICAL CO., LTD.)): 10 parts by weight Bisphenol A EO denaturalized (recurring unit of an ethyleneoxide denaturalized portion: m+n≈30) diacrylate (NK ester A-BPE-30 (commercial name) produced by SHIN-NAKAMURA CHEMICAL CO., LTD.): 10 parts by weight (d) Other Component Photoreaction Initiator Bis (2,4-cyclopentadiene-1-yl)-bis (2,6'-difluoro-3-(1H-pyrrole-1-yl)-phenyl)titanium (IRGACURE 784 (commercial name) produced by Ciba Specialty Chemicals): 1 part by weight Epoxy Resin Bisphenol A type epoxy resin (Epikote 828 (commercial name) produced by Japan Epoxy Resins Co., Ltd.): 10 parts by weight Curing Agent 4,4'-diaminodiphenylmethane (DDM): 1 part by weight (Results of Property Evaluation)

Properties of the thus obtained photosensitive dry film resist were evaluated as follows.

Flame retardancy test: The flame disappeared in 3.5 seconds on the average, so that this was regarded as being proper.

Developing property: Both a hole of 100×100 μm and a hole of 200×200 μm were developed, so that the photosensitive dry film resist was regarded as being proper in this view point.

Heat resistance: Under both the normal condition and the moisture absorption condition, the 30-second-dipable temperature was 320° C., so that the photosensitive dry film resist was regarded as being proper in this view point.

Example 35

(Production of Photosensitive Dry Film Resist)

15 g of the soluble polyimide resin synthesized in Synthesis Example 18 was dissolved in 35 g of dioxolane, thereby preparing an organic solvent solution so that its solid content weight ratio (Sc) was 30%.

An organic solvent solution of the photosensitive resin composition was prepared by mixing the following components so as to produce a photosensitive dry film resist in a B stage state.

(a) Soluble Polyimide Resin

Soluble polyimide resin synthesized in Synthesis Example 18 (in accordance with conversion based on a solid content): 55 parts by weight (b) Cross-linked Phenoxyphosphazene Compound Mixture obtained by mixing (i) a cross-linked phenoxyphosphazene compound obtained by cross-linking a circular phenoxyphosphazene compound, represented by formula (22) where a is an integer ranging from 3 to 20, with a p-phenylene group and (ii) a cross-linked phenoxyphosphazene compound obtained by cross-linking a chain phenoxyphosphazene compound, represented by formula (23) where b is an integer ranging from 3 to 1000, with a p-phenylene group. SPB-156 (commercial name) produced by Otsuka Chemicals Inc.: 20 parts by weight (c) (Meth)acrylic Compound Bisphenol A EO denaturalized (recurring unit of an ethyleneoxide denaturalized portion: m+n≈10) diacrylate (NK ester A-BPE-10 (commercial name) produced by SHIN-NAKAMURA CHEMICAL CO., LTD.)): 10 parts by weight Bisphenol A type epoxyacrylate (Ebecryl 3700 (commercial name) produced by DAICEL-UCB Company LTD.): 15 parts by weight (d) Other Component Photoreaction Initiator Bis (2,4-cyclopentadiene-1-yl)-bis (2,6'-difluoro-3-(1 H-pyrrole-1-yl)-phenyl) titanium (IRGACURE 784 (commercial name) produced by Ciba Specialty Chemicals): 1 part by weight (Results of Property Evaluation)

Properties of the thus obtained photosensitive dry film resist were evaluated as follows.

Flame retardancy test: The flame disappeared in 3.0 seconds on the average, so that this was regarded as being proper.

Developing property: Both a hole of 100×100 μm and a hole of 200×200 μm were developed, so that the photosensitive dry film resist was regarded as being proper in this view point.

Heat resistance: Under both the normal condition and the moisture absorption condition, the 30-second-dipable temperature was 320° C., so that the photosensitive dry film resist was regarded as being proper in this view point.

Comparative Example 6

(Synthesis of Base Polymer)

Among polymers used instead of the soluble polyimide resin serving as the component (a) in Examples 32 to 35, a polymer component having a largest weight in the photosensitive resin composition is referred to as a base polymer.

(Synthesis of Polyimide Resin)

173 g (0.30 mol) of ESDA and 300 g of DMF were placed in a 500 ml separable flask provided with a stirrer, thereby preparing a DMF solution of ESDA. Next, a solution obtained by dissolving 86.5 g (0.20 mol) of BAPS-M in 100 g of DMF was added to 100 g of DMF, and the mixture was intensely stirred. After the solution became even, 83.5 g (0.10 mol) of silicondiamine KF-8010 was added thereto, and the mixture was intensely stirred for one hour.

The thus obtained polyamide acid solution was placed in a tray coated with fluorocarbon resin and was dried in a vacuum oven at 200° C. under reduced pressure of 660 Pa for two hours, thereby obtaining 315 g of polyimide resin. The polyimide resin had no carboxyl group and/or no hydroxyl group in its imide resin. Further, no photosensitive group was introduced therein.

(Production of Photosensitive Dry Film Resist)

15 g of the polyimide resin synthesized in the foregoing manner was dissolved in 35 g of dioxolane, thereby preparing a varnish whose solid content weight ratio %(Sc) was 30%.

The same operation was carried out as in Example 32 except that the polyimide resin synthesized in the present example was used instead of the component (a) of Example 32, thereby producing a photosensitive dry film resist.

(Results of Property Evaluation)

Properties of the thus obtained photosensitive dry film resist were evaluated as follows.

Flame retardancy test: The flame disappeared in 3.0 seconds on the average, so that this was regarded as being proper.

Developing property: Neither a hole of 100×100 μm nor a hole of 200×200 μm were developed, so that the photosensitive dry film resist was regarded as being improper in this view point.

Heat resistance: Under both the normal condition and the moisture absorption condition, the 30-second-dipable temperature was 320° C., so that the photosensitive dry film resist was regarded as being proper in this view point.

In this manner, when the polyimide having no carboxyl group and/or a no hydroxyl group is used as a base polymer, the flame retardancy and the heat resistance were favorable, but its developing property was not favorable.

Comparative Example 7

(Synthesis of Base Polymer)

Monomers of methylmethacrylate, n-butylmethacrylate, 2-ethylhexylacrylate, and methacrylic acid were used as materials for the polyimide resin. These monomer components were copolymerized in accordance with a known method, thereby obtaining a copolymer having a carboxyl group. A polymerization ratio of the monomer components was methylmethacrylate/n-butylmethacrylate/2-ethylhexylacr ylate/methacrylic acid=60/10/10/20 (in terms of a weight).

(Production of Photosensitive Dry Film Resist)

The photosensitive dry film resist was produced under the same condition as in Example 33 except that the acrylic copolymer synthesized in the present example was used instead of the component (a) of Example 33.

(Results of Property Evaluation)

Properties of the obtained photosensitive dry film resist were evaluated as follows.

Flame retardancy test: The flame did not disappeared within 10 seconds, and the flame rose to the clamp, so that this was regarded as being improper.

Bleed: There was no bleed.

Developing property: Both a hole of 100×100 μm and a hole of 200×200 μm were developed, so that the photosensitive dry film resist was regarded as being proper in this view point.

Heat resistance: Under the normal condition, the 30-second-dipable temperature was 280° C. Under the moisture absorption condition, the 30-second-dipable temperature was 240° C. Thus, the photosensitive dry film resist was regarded as being proper in this view point.

In this manner, when the acrylic copolymer made of a monomer having no aromatic ring was used as a base polymer, the developing property of the obtained photosensitive dry film resist was favorable, but its heat resistance was not favorable. Further, even when the phosphazene compound was used, its flame retardancy was not favorable.

[Comparative Example 8]

(Production of Photosensitive Dry Film Resist)

The photosensitive dry film resist was produced under the same condition as in Example 33 except that a propoxylated phosphazene compound was used instead of the component (b) of Example 33.

(Results of Property Evaluation)

Properties of the obtained photosensitive dry film resist were evaluated as follows.

Flame retardancy test: The flame did not disappeared within 10 seconds, so that this was regarded as being improper.

Developing property: Both a hole of 100×100 μm and a hole of 200×200 μm were developed, so that the photosensitive dry film resist was regarded as being proper in this view point.

Heat resistance: Under both the normal condition and the moisture absorption condition, the 30-second-dipable temperature was 290° C., so that the photosensitive dry film resist was regarded as being improper in this view point.

In this manner, when the propoxylated phosphazene was used, the flame retardancy of the obtained photosensitive dry film resist was not sufficient. Further, this resulted in drop of the heat resistance.

TABLE 1

| | Examples | | | |
|---|---|---|---|---|
| | 32 | 33 | 34 | 35 |
| Soluble polyimide resin (part by weight) | Synthesis Example 15 50 | Synthesis Example 16 50 | Synthesis Example 17 50 | Synthesis Example 18 55 |
| Cross-linked phenoxyphosphagene (part by weight) | 20 | 20 | 20 | 20 |
| (Meth)acrylic compound (part by weight) | 20 | 30 | 20 | 25 |
| Photoreaction initiator (part by weight) | 1 | 1 | 1 | 1 |
| Epoxy resin (part by weight) | 10 | | 10 | |
| Curing agent (part by weight) | 1 | | 1 | |
| Flame retardancy test | Proper | Proper | Proper | Proper |
| Developing property | Proper | Proper | Proper | Proper |
| Heat resistance | Proper | Proper | Proper | Proper |

TABLE 2

| | Comparative Examples | | |
|---|---|---|---|
| | 6 | 7 | 8 |
| Soluble polyimide resin (part by weight). | | | Synthesis Example 16 50 |
| Polyimide resin having no carboxyl group and/or no hydroxyl group (part by weight) | 50 | | |
| Acrylic copolymer (part by weight) | | 50 | |
| Cross-linked phenoxyphosphagene (part by weight) | 20 | 20 | |
| Propoxylated phosphazene (part by weight) | | | 20 |
| (Meth)acrylic compound (part by weight) | 20 | 30 | 30 |

TABLE 2-continued

|  | Comparative Examples | | |
|---|---|---|---|
|  | 6 | 7 | 8 |
| Photoreaction initiator (part by weight) | 1 | 1 | 1 |
| Epoxy resin (part by weight) | 10 | | |
| Curing agent (part by weight) | 1 | | |
| Flame retardancy test | Proper | Improper | Improper |
| Developing property | Improper | Proper | Proper |
| Heat resistance | Proper | Improper | Improper |

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

As described above, each of the phosphazene compound and the photosensitive resin composition according to the present invention has favorable water system developing property (developing property in basic aqueous solution) and allows both (i) properties such as heat resistance, anti-hydrolysis property, easiness to process (inclusive of solvent solubility), bonding property, and (ii)photosensitivity, flame retardancy, and sufficient mechanical strength, the phosphazene compound and the photosensitive resin composition being favorably applicable to production of a wiring board which can sufficiently cover smaller and lighter electronic parts of electronic devices. Thus, in case where the photosensitive resin composition according to the present invention is formed into a varnish-like solution or the like, it is possible to use the solution as an effective resin chemical product constituting an adhesive, a coating agent, an ink, or the like. Further, in case where the photosensitive resin composition according to the present invention is formed into a resin sheet or a resin film, it is possible to favorably use the photosensitive resin composition as a print wiring board (FPC) adhesive sheet, a pattern circuit resist film, a photosensitive cover lay film, a photosensitive dry film resist, a print wiring board insulative circuit protection film, a print wiring board substrate, or the like.

Thus, the present invention can be used not only in various resin industries and chemical industries for producing photosensitive resin compositions but also in resin processing industries for producing resin chemical products and laminates etc. and electronic part industries and electronic device industries for producing/using circuit substrates and the like.

The invention claimed is:

1. A phosphazene compound, obtained by reacting a phenoxyphosphazene compound (A-1) having a phenolic hydroxyl group and/or a cross-linked phenoxyphosphazene compound (A-2) obtained by cross-linking the phenoxyphosphazene compound (A-1) with an epoxy compound (B) having an unsaturated double bond, wherein the phosphazene compound has an unsaturated double bond and a phenolic hydroxyl group in its molecule; and the epoxy compound (B) is at least one epoxy compound selected from the group consisting of glycidylmethacrylate, glycidylacrylate, allylglycidylether, glycidylvinylether, and a compound represented by the following formula (10)

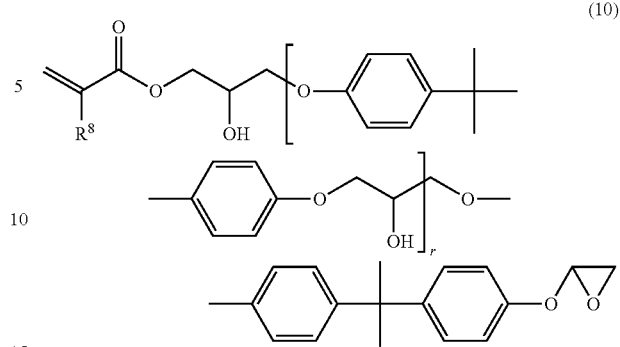

(10)

wherein r represents an integer ranging from 0 to 40, and $R^8$ represents H or a methyl group.

2. The phosphazene compound as set forth in claim 1, wherein the phenoxyphosphazene compound (A-1) is a circular phenoxyphosphazene compound (A-11) represented by formula (1)

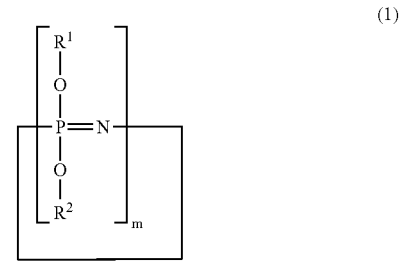

(1)

where m represents an integer ranging from 3 to 25, and each of $R^1$ and $R^2$ represents a phenyl group or a hydroxyphenyl group, and a single molecule has one or more hydroxyphenyl groups.

3. A photosensitive resin composition, comprising at least the phosphazene compound as set forth in claim 1 and a soluble polyimide resin (D) which is soluble in an organic solvent.

4. The photosensitive resin composition as set forth in claim 3, further comprising a photoreaction initiator (E-1).

5. A photosensitive resin composition, comprising at least the phosphazene compound as set forth in claim 1 and a photoreaction initiator (E-1).

6. The photosensitive resin composition as set forth in claim 3, further comprising a compound having a carbon-carbon double bond (E-4).

7. The photosensitive resin composition as set forth in claim 3, wherein 1 wt% or more of the soluble polyimide resin (D) is dissolved in at least one kind of an organic solvent selected from dioxolane, dioxane, tetrahydrofuran, N,N-dimethylformamide, N,N-dimethylacetamide, and N-methyl-2-pyrrolidone at temperature ranging from room temperature to 100° C.

8. A photosensitive resin film, being formed by using the photosensitive resin composition as set forth in claim 3.

9. The photosensitive resin film as set forth in claim 8, being used as a print wiring board adhesive sheet, a photosensitive cover lay film, a print wiring insulative protection film, or a print wiring board substrate.

* * * * *